(12) United States Patent
Bode et al.

(10) Patent No.: US 8,501,767 B2
(45) Date of Patent: Aug. 6, 2013

(54) IMIDAZOPYRIDINES AND IMIDAZOPYRIMIDINES AS HIV-1 REVERSE TRANSCRIPTASE INHIBITORS

(75) Inventors: Moira Leanne Bode, Midrand (ZA); Amanda Louise Rousseau, Dunvegan (ZA); David Gravestock, Ravenswood (ZA); Simon Sana Moleele, Soweto (ZA); Christiaan Wynand Van Der Westhuyzen, Fourways (ZA)

(73) Assignee: CSIR, Pretoria (ZA)

( * ) Notice: Subject to any disclaimer, the term of this patent is extended or adjusted under 35 U.S.C. 154(b) by 3 days.

(21) Appl. No.: 13/119,431

(22) PCT Filed: Sep. 16, 2009

(86) PCT No.: PCT/IB2009/054021
§ 371 (c)(1),
(2), (4) Date: Aug. 30, 2011

(87) PCT Pub. No.: WO2010/032195
PCT Pub. Date: Mar. 25, 2010

(65) Prior Publication Data
US 2011/0312957 A1    Dec. 22, 2011

(30) Foreign Application Priority Data
Sep. 16, 2008  (ZA) .................. 2008/07954

(51) Int. Cl.
  *A01N 43/42* (2006.01)
  *A61K 31/44* (2006.01)
  *C07D 471/02* (2006.01)
  *C07D 491/02* (2006.01)
  *C07D 498/02* (2006.01)
  *C07D 513/02* (2006.01)
  *C07D 515/02* (2006.01)

(52) U.S. Cl.
  USPC .......................................... 514/300; 546/121

(58) Field of Classification Search
  None
  See application file for complete search history.

(56) References Cited

U.S. PATENT DOCUMENTS

| 4,507,294 | A  | 3/1985 | Bristol et al. |
| 6,020,342 | A  | 2/2000 | Tanaka et al. |
| 2003/0144518 | A1 | 7/2003 | Chen |
| 2008/0085896 | A1 | 4/2008 | Lee et al. |

FOREIGN PATENT DOCUMENTS

| DE | 19948437 | 6/2001 |
| DE | 10050663 | 4/2002 |
| DE | 10150172 | 4/2003 |
| DE | 102005019181 | 10/2006 |
| DE | 10206028862 | 12/2007 |
| DE | 102006048728 | 4/2008 |
| EP | 0052016 | 5/1982 |
| EP | 0068378 | 1/1983 |
| EP | 0266890 | 5/1988 |
| WO | WO 01/27109 | 4/2001 |
| WO | WO 01/27110 | 4/2001 |
| WO | WO 01/27111 | 4/2001 |
| WO | WO02/48146 | 6/2002 |
| WO | WO2005/105798 | 11/2005 |
| WO | WO2006/029980 | 3/2006 |
| WO | WO2006/094235 | 9/2006 |
| WO | WO2006/101455 | 9/2006 |
| WO | WO2007/067711 | 6/2007 |
| WO | WO2008/016648 | * 2/2008 |
| WO | WO2008/022396 | 2/2008 |
| WO | WO2008/068392 | 6/2008 |
| WO | WO2008/082490 | 7/2008 |
| WO | WO2008/134553 | 11/2008 |
| WO | WO2008/141239 | 11/2008 |
| WO | WO2009/023179 | 2/2009 |
| WO | WO2009/061856 | 5/2009 |

OTHER PUBLICATIONS

H.Bienayme, A New Heterocyclic Multicomponent Reaction for the Combinatorial Synthesis of Fused 3-Aminomidazoles, Angew. Chem.Int.Ed., vol. 37,No. 16 (1998).
A.S.Kieselyov, A Novel Three-Component Reacxtion of N-Fluoropyridinium Salts: A Facile APprocat to Imidazol[1,2-a]pyridines, Tetrahedron Lett., vol. 46 (2005).

* cited by examiner

*Primary Examiner* — Jeffrey Murray
(74) *Attorney, Agent, or Firm* — Wilson, Sonsini, Goodrich & Rosati

(57) ABSTRACT

The invention provides compounds of formula A or B which are useful in the treatment of a subject infected with HIV.

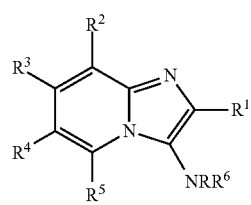

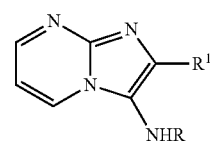

8 Claims, No Drawings

IMIDAZOPYRIDINES AND IMIDAZOPYRIMIDINES AS HIV-1 REVERSE TRANSCRIPTASE INHIBITORS

CROSS-REFERENCE TO RELATED APPLICATIONS

This application is a U.S. national stage entry under 35 U.S.C. §371 of International Patent Application PCT/IB2009/054021 filed 15, Sep. 2009, which claims priority to South African Patent Application No. 2008/07954, entitled COMPOUNDS AND COMPOSITIONS HAVING ACTIVITY AGAINST THE ENZYME HIV-1 REVERSE TRANSCRIPTASE, filed 16, Sep. 2008, all of which are incorporated herein by reference in their entirety.

THIS INVENTION relates to compounds and compositions having activity against the enzyme HIV-1 reverse transcriptase.

Highly active antiretroviral treatment (HAART) is a treatment regimen for HIV-AIDS sufferers which combines a cocktail of antiretroviral drugs chosen from a number of different classes. One of these classes comprises the non-nucleoside reverse transcriptase inhibitors (NNRTIs). These drugs act by inhibiting the enzyme HIV-1 reverse transcriptase. This enzyme is a validated target for the development of anti-HIV drugs. There are a number of NNRTIs that are FDA approved and one of these drugs generally forms part of the first-line treatment regimen against HIV-AIDS. There are a number of advantages associated with this class. One of the advantages is the excellent selectivity index (ratio of 50% cytotoxic concentration to 50% antivirally effective concentration) displayed by these drugs, which is usually of the order of 10,000-100,000. This high selectivity makes the NNRTI class the least toxic of the clinically approved antiretrovirals and makes these drugs suitable for use in the prevention of mother to child transmission. The reason for the high selectivity is the fact that NNRTIs only recognise and bind to HIV-1 reverse transcriptase, not to any other RTs or DNA or RNA polymerases. These drugs act by binding to a lipophilic, non-substrate binding pocket located about 10 Å from the substrate binding site. This binding results in conformational changes within the reverse transcriptase catalytic site that leads to a dramatic slowing down of the catalytic activity. The allosteric inhibitors of reverse transcriptase (RT) possess very different structural characteristics and as many as 50 diverse structural classes have been found to have activity against reverse transcriptase. The first generation of NNRTIs (exemplified by nevirapine and delavirdine) is sensitive to the development of drug resistance and even a single amino acid mutation in the NNRTI binding region of RT confers a high level of drug resistance. There is accordingly a requirement for NNRTIs which can inhibit as many different RT mutants as possible.

The applicant is aware of PCT/US2008/082531 entitled "Non-nucleoside reverse transcriptase inhibitors" (filed on 5 Nov. 2008) which claims the priority of U.S. Ser. No. 60/986,990 (filed on 9 Nov. 2007). The generic structure disclosed in this document covers a very large number of compounds. The document specifically discloses about 11600 compounds. However, inhibition data are provided for only about 30 compounds. The generic disclosure of the present application covers a substantially smaller number of compounds and those compounds of PCT/US2008/082531 which fall within the scope of the generic structure of the present application have been excluded by the introduction of provisos.

According to a first aspect of the invention there is provided a compound selected from compounds of the formula A or B

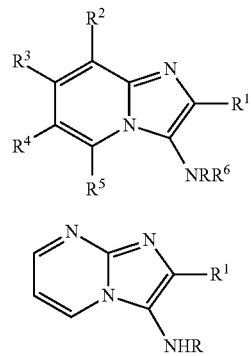

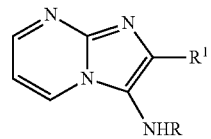

in which, for formula A,

R is selected from alkyl, branched alkyl, cycloalkyl, aryl, substituted aryl, naphthyl, benzyl, adamantyl and polycycloalkyl, $R^1$ is selected from alkyl, cycloalkyl, substituted alkyl, branched alkyl, phenyl, substituted phenyl, substituted benzyl, heteroaryl, substituted heteroaryl, oxacycloalkyl, bicycloalkyl, furyl, substituted furyl, thienyl and substituted thienyl, isoxazolyl, substituted isoxazolyl $R^2$-$R^5$ are independently selected from H, halogen, cyano, alkoxy, aryloxy, substituted aryl, alkyl and substituted alkyl, or $R^2$ and $R^3$ together form a carbocyclic ring or, independently, $R^4$ and $R^5$ together form a carbocyclic ring, $R^6$ is H, alkyl or alkanoyl, provided that (a) if R is cyclohexyl and $R^2$-$R^6$ are H, then $R^1$ is not 2-bromophenyl, 3-bromophenyl, 2-chlorophenyl, 3-chlorophenyl, 2-trifluoromethylphenyl, 2,4-dichlorophenyl, 2,6-dichlorophenyl, 2,6-difluorophenyl, 4-fluorophenyl, isopropyl, 2-furyl, 2-hydroxyphenyl, 4-methoxyphenyl, 3,4-dimethoxyphenyl or 2-fluorophenyl;

(b) if R is cyclopentyl and $R^2$-$R^6$ are H, then $R^1$ is not 2-bromophenyl, 3-bromophenyl, 2-chlorophenyl, 2,4-dichlorophenyl, 2,6-dichlorophenyl, 2,6-difluorophenyl, 2,4-difluorophenyl, 2-trifluoromethylphenyl or 2-fluorophenyl;

(c) if R is cyclohexyl or cyclopentyl and $R^3$, $R^4$, $R^5$ and $R^6$ are H, and $R^2$ is methyl, then $R^1$ is not 2-chlorophenyl;

(d) if R is cyclohexyl or cyclopentyl and $R^2$, $R^4$, $R^5$ and $R^6$ are H, and $R^3$ is methyl then $R^1$ is not 2-chlorophenyl;

(e) if R is cyclohexyl or cyclopentyl and $R^2$, $R^3$, $R^5$ and $R^6$ are H, and $R^4$ is methyl then $R^1$ is not 2-chlorophenyl;

(f) if R is cyclohexyl or cyclopentyl, and $R^2$, $R^3$, $R^4$ and $R^6$ are H, and $R^5$ is methyl, ethyl or trifluoromethyl, then $R^1$ is not 2-chlorophenyl, 2-fluorophenyl, 2,6-difluorophenyl, 2-fluoro-5-methylphenyl, 2-fluoro-6-methoxyphenyl, 2,6-difluoro-4-methoxyphenyl, 2,4-difluorophenyl, 2-chloro-4-fluorophenyl, 2-chloro-4-pyridinyl, 2-fluoro-4-pyridinyl or 2-chloro-6-fluorophenyl;

(g) if R is cyclohexyl, and $R^2$, $R^3$ and $R^5$ are H, and $R^4$ is fluorine, chlorine or bromine, then $R^1$ is not 2-chlorophenyl;

(h) if R is cyclohexyl, and $R^3$ and $R^5$ are methyl and $R^2$, $R^4$ and $R^6$ are H $R^1$ is not 2-chlorophenyl;

and in which, for formula B,

R is cycloalkyl and $R^1$ is substituted aryl.

The alkyl and branched alkyl groups of $R^1$ may be optionally substituted by one or more heteroatoms. The heteroatoms may be oxygen, nitrogen or sulphur. For example the alkyl group may be substituted by a thiomethyl group. The substituted alkyl group may, therefore, be a 2-thiomethylethyl group. The phenyl group may optionally be substituted by one or more substituents selected from halogen, OH, alkyl, alkoxy, cyano, amino, substituted alkyl, halo or nitro. The heteroaryl group may be an O, N or S heteroaryl group and may, for example, be selected from oxazolyl, isoxazolyl, substituted isoxazolyl, furanyl, and thiophenyl groups.

The halogen may be selected from one or more of F, Cl and Br.

The cycloalkyl group may be selected from $C_3$-$C_6$ cycloalkyl groups and adamantane. For example, the cycloalkyl group may be a cyclopropyl, cyclobutyl, cyclopentyl, cyclohexyl or tetrahydrofuranyl group.

The alkyl and branched alkyl groups may be selected from $C_2$ to $C_{12}$ alkyl and branched alkyl groups. Preferred alkyl and branched alkyl groups include 2-pentyl, 1-butyl, 2-propyl, 2-butyl and 1-pentyl and 1-octyl.

Examples of preferred compounds of the invention, of formula A are compounds in which:

(a) R is selected from ethyl, 2-morpholinoethyl, 1-butyl, 2-pentyl, 1-pentyl, 1,1,3,3-tetramethylbutyl, isopropyl, cyclohexyl, cyclopropyl, 4-(3,4-dichlorophenoxy)butyl, 1-adamantyl, 4-methoxyphenyl, 2-naphthyl, benzyl, 4-chlorobenzyl, 2-chloro-6-methylphenyl, 2-chlorophenyl, 3-chlorophenyl, cyclopentyl;

(b) $R^1$ is selected from ethyl, 2-(methylthio)ethyl, 1-propyl, 2-butyl, 2-methyl-1-propyl, 2,2-dimethyl-1-propyl, cyclopropyl, cyclopentyl, cyclohexyl, 1-pentyl, 2-pentyl, 3-pentyl, tert-butyl, isopropyl, isobutyl, 1-octyl, 1-phenylethyl, 2-hydroxyphenyl, 4-hydroxyphenyl, 4-methoxyphenyl, 2-bromophenyl, 3-bromophenyl, 4-bromophenyl, 2-chlorophenyl, 3-chlorophenyl, 4-chlorophenyl, 4-nitrophenyl, 2-fluorophenyl, 4-fluorophenyl, 3-ethoxy-4-hydroxyphenyl, 4-dimethylaminophenyl, 3,4-dimethoxyphenyl, 3,5-dimethoxy-4-hydroxyphenyl, 4-benzyloxyphenyl, 2,4-dimethoxyphenyl, 4-hydroxy-3-methoxy-phenyl, 3-hydroxy-4-methoxy-phenyl, 2,3,6-trichlorophenyl, 2-fluoro-(3-methoxy)phenyl, 3-chloro-2-fluoro-phenyl, 2-trifluoromethylphenyl, 4-trifluoromethylphenyl, 2,4-dichlorophenyl, 2,4-difluorophenyl, 2,5-dichlorophenyl, 2,6-dichlorophenyl, 2,6-difluorophenyl, 4-chloro-3-fluoro-phenyl, 2-chloro-6-fluoro-5-methyl-phenyl, 3-(5-methyl)isoxazolyl, 2-(5-hydroxymethyl)furanyl, 2-furanyl, 2-(5-chloro)furanyl, 2-(5-ethyl)thienyl, 2-(3-methyl)thienyl, 2,4,5-trifluorophenyl, 3-(2,5-dimethoxy)tetrahydrofuranyl, 4-cyanophenyl, 3-cyanophenyl, norpinenyl;

(c) $R^2$ is selected from H, benzyloxy, methyl, chloro;

(d) $R^3$ is selected from H, methyl, chloro;

(e) $R^4$ is selected from H, chloro, fluoro, methyl, bromo, nitrile, 2-methylphenyl, 4-methoxyphenyl, (f) $R^5$ is selected from H, methyl, chloro, bromo, 2-methylphenyl, phenyloxy, 4-methoxyphenyl, ethoxy, cyano;

(g) $R^6$ is selected from H, ethyl, acetyl, (h) $R^4$ and $R^5$ together form an aromatic ring.

(i) $R^2$ and $R^3$ together form an aromatic ring.

According to a second aspect of the invention there is provided a composition for use in treating a subject who has been infected with HIV, the composition including a compound selected from compounds of formula A or B as described above.

According to a third aspect of the invention there is provided a substance or composition for use in a method of treating a subject who has been infected by HIV, the substance or composition including a compound selected from compounds of formula A or B as described above.

According to a fourth aspect of the invention, there is provided the use of a compound selected from compounds of formula A or B as described above in the manufacture of a medicament for the treatment of a subject infected with HIV.

The compounds of the invention have been found to have activity against the enzyme reverse transcriptase in the μ-molar range. In addition these compounds have been found to be active against HIV in the whole cell PBMC or MAGI anti-HIV assay in the μM to nM range.

According to a fifth aspect of the invention there is provided a method of treating a subject who has been infected by HIV, the method including administering to a subject in need of treatment a compound selected from compounds of formula A or B as described above.

The compounds of the invention can readily be prepared in one step by an acid-catalysed three-component coupling reaction as shown in Scheme 1 in which a 2-aminopyridine or a substituted 2-aminopyridine, in which R, $R^1$, $R^2$, $R^3$, $R^4$ and $R^5$ are as hereinbefore described, is reacted with an aldehyde and an isonitrile in the presence of montmorillonite K-10 clay or any other suitable acid catalyst at 95-100° C. for 5-8 hours under conventional heating or 15-30 min under microwave irradiation. The product is generally isolated by column chromatography.

Scheme 1. Preparation of imidazo[1,2-a]pyridines

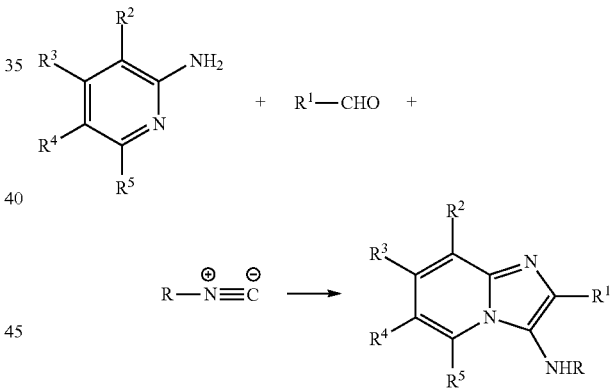

Thus according to a sixth aspect of the invention, there is provided a method of synthesising a compound selected from compounds of formula A or B as described above, which includes the step of condensing a 2-aminopyridine or a substituted 2-aminopyridine of the formula

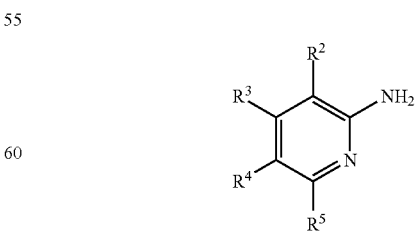

or 2-aminopyrimidine with an aldehyde of the formula $R^1$CHO and an isocyanide of the formula RNC in which R, $R^1$, $R^2$, $R^3$, $R^4$, $R^5$ and $R^6$ are as described above.

Examples of the compounds of the invention are set out in Scheme 2.
Scheme 2
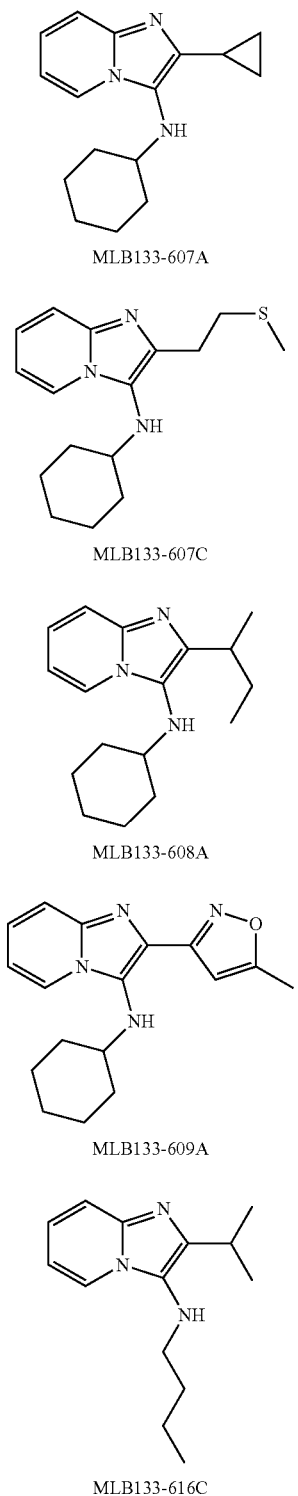
MLB133-607A
MLB133-607C
MLB133-608A
MLB133-609A
MLB133-616C
-continued
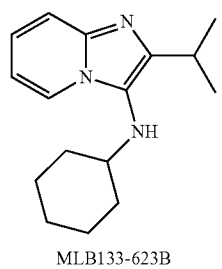
MLB133-623B
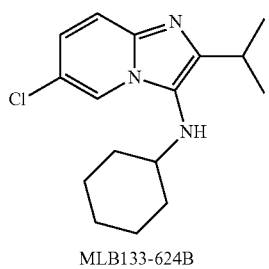
MLB133-624B
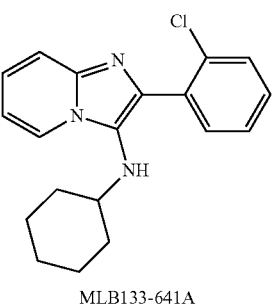
MLB133-641A
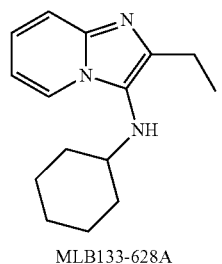
MLB133-628A
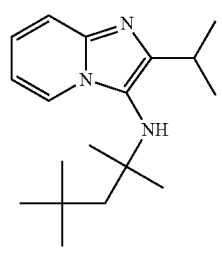
MLB133-616B -continued
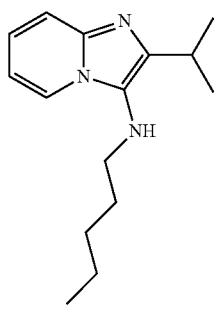
MLB133-616A
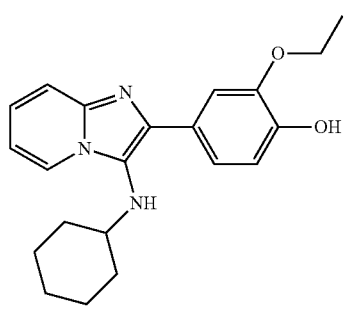
MLB133-640A
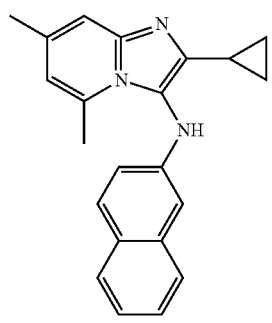
MLB133-635C
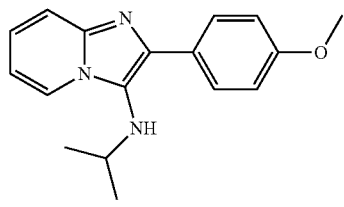
MLB133-627A
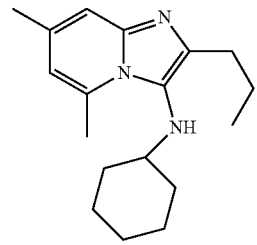
MLB133-640C
-continued
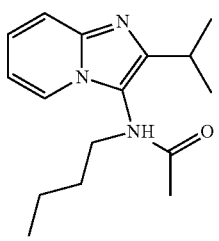
DG120-034
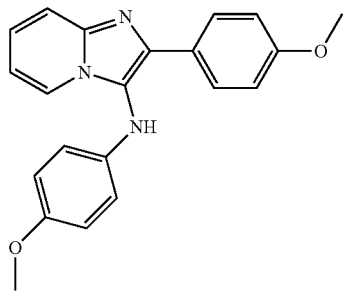
MLB133-628B
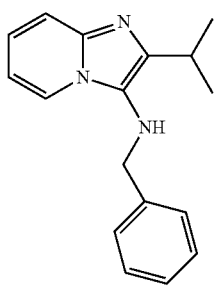
MLB133-615B
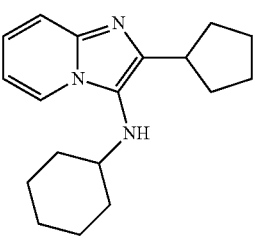
MLB133-607B
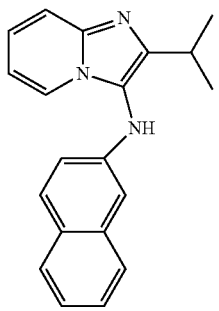
MLB133-615C

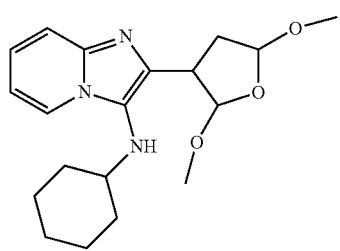
MLB133-608C
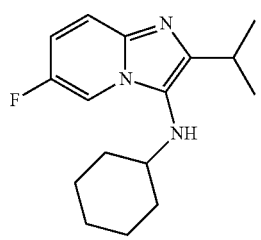
MLB133-623A
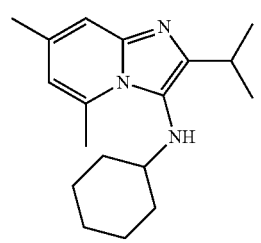
MLB133-623C
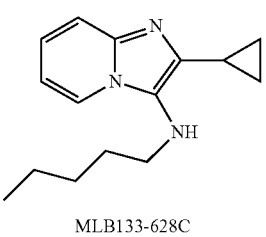
MLB133-628C
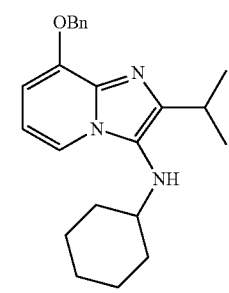
MLB133-624A
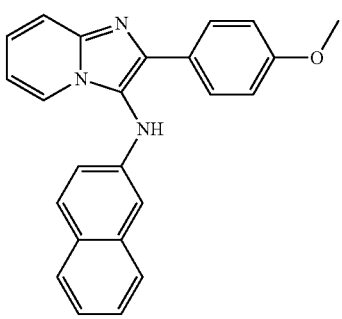
MLB133-627C
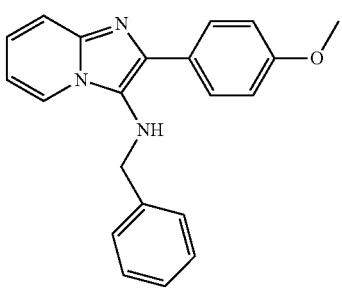
MLB133-629B
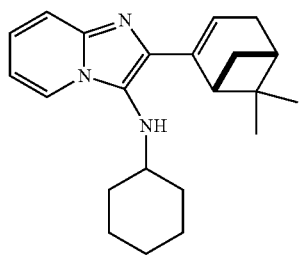
MLB133-634A
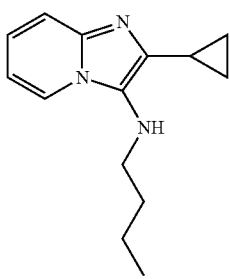
MLB133-627B
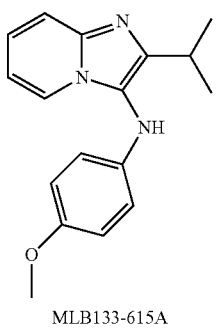
MLB133-615A -continued
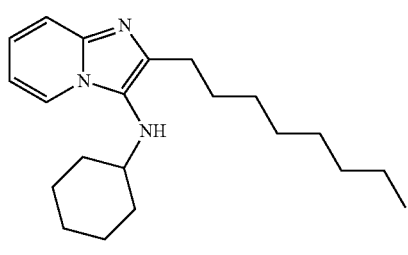
MLB133-640B
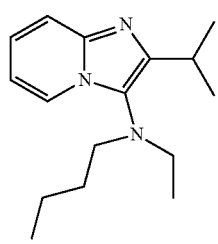
DG120-036
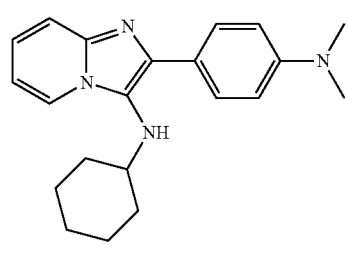
MLB133-608B
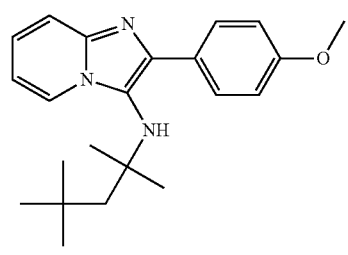
MLB133-629A
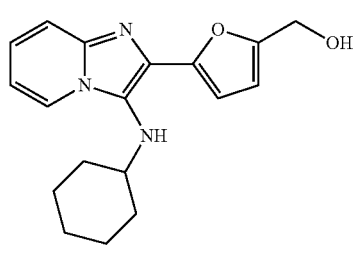
MLB133-634B
-continued
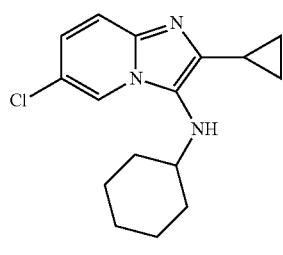
MLB133-636A
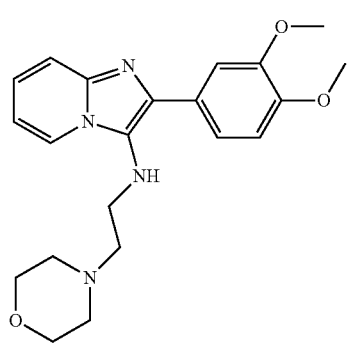
MR762-137.4
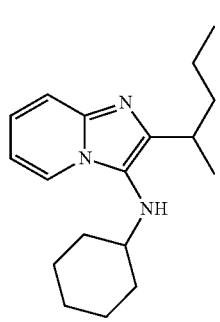
MLB133-649A
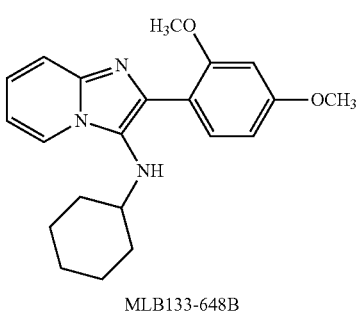
MLB133-648B
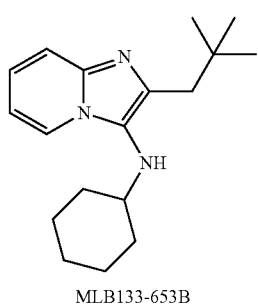
MLB133-653B

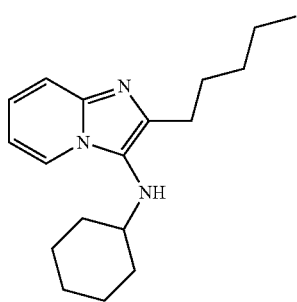
MLB133-655A
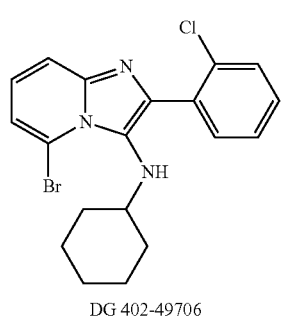
DG 402-49706
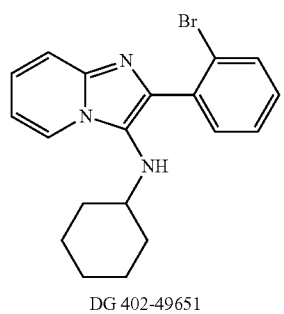
DG 402-49651
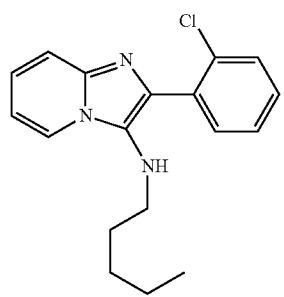
DG 402-49659
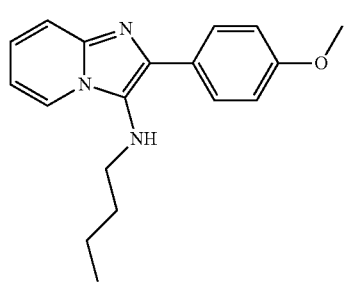
DG789-110
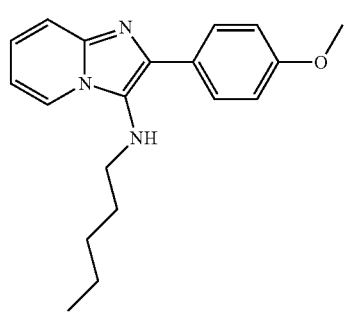
DG789-112
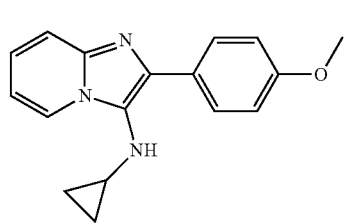
DG 789-116
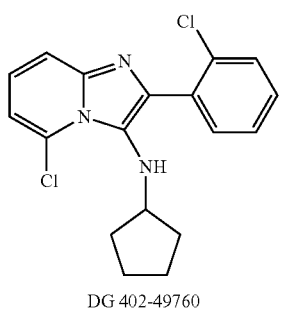
DG 402-49760
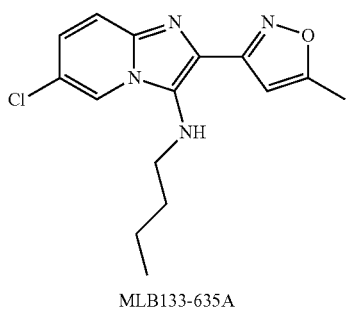
MLB133-635A
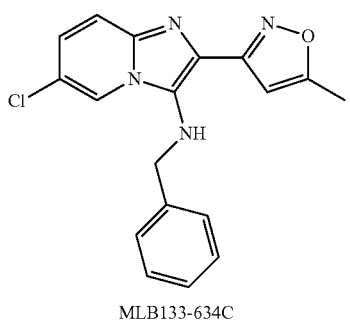
MLB133-634C -continued
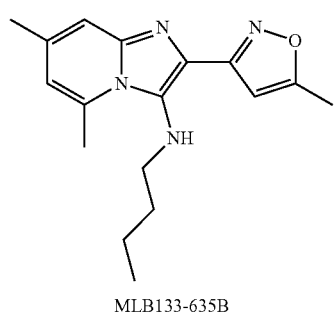
MLB133-635B
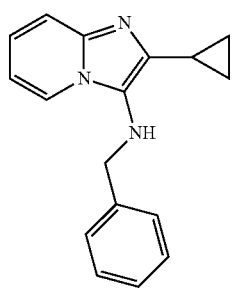
MLB133-636B
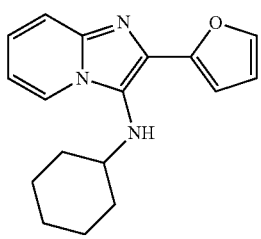
MR762-137.15
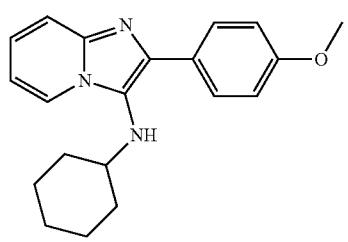
10061
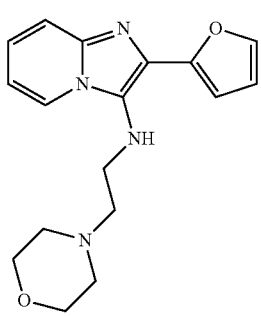
MR762-137.8
-continued
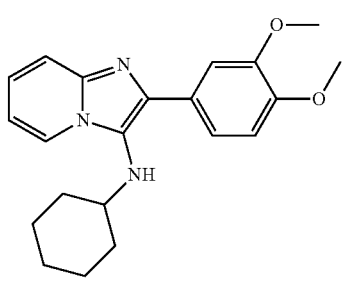
MR762-137.11
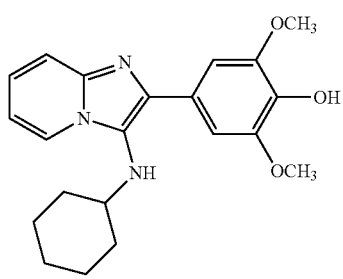
MLB133-639A
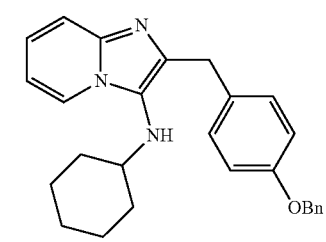
MLB133-639C
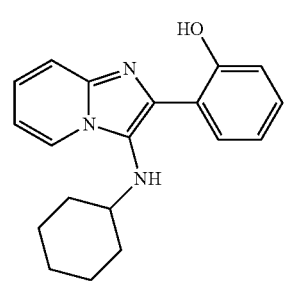
MLB133-639B
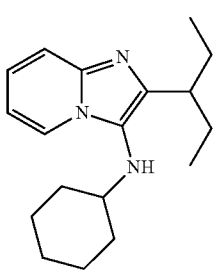
MLB133-649C -continued
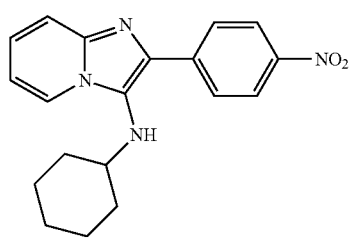
MLB133-648A
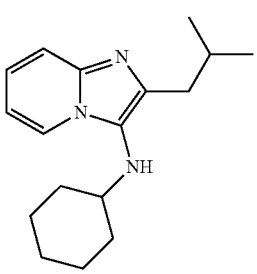
MLB133-648C
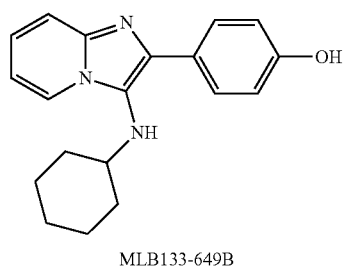
MLB133-649B
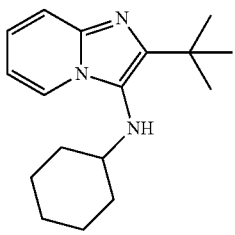
MLB133-650A
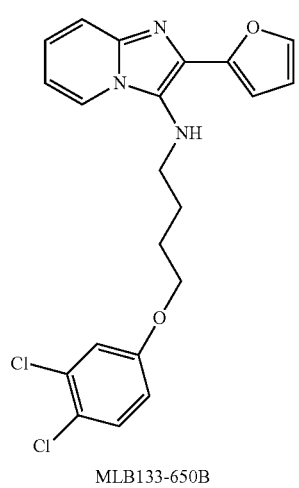
MLB133-650B
-continued
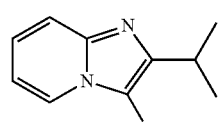
MLB133-650C
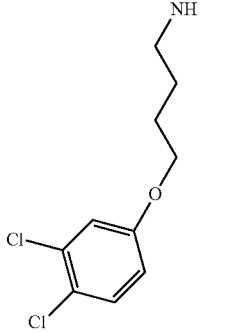
MLB133-650D
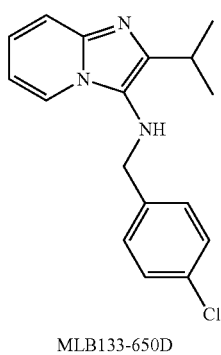
MLB133-653A
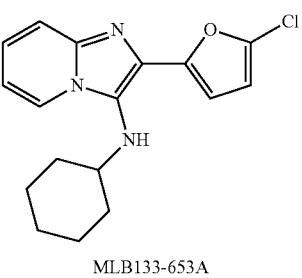
MLB133-653C
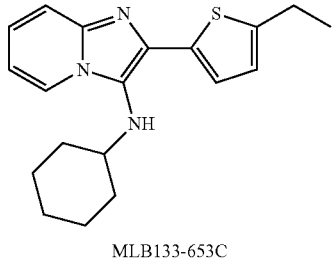

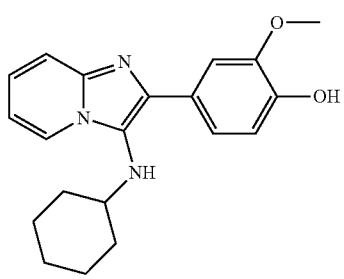
MLB133-654C
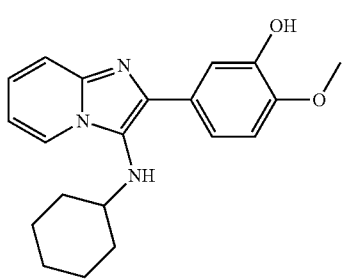
MLB133-654A
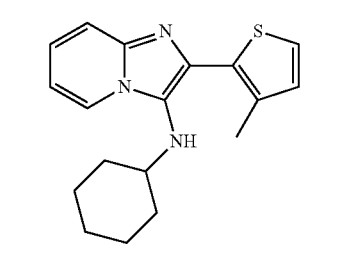
MLB133-654B
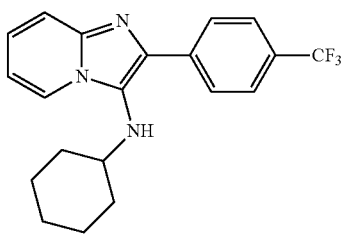
DG 402-49647
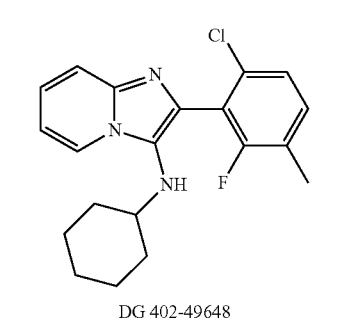
DG 402-49648
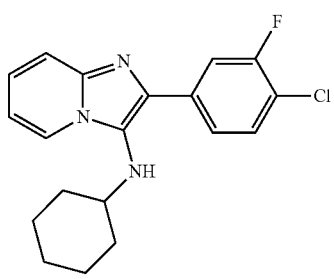
DG 402-49649
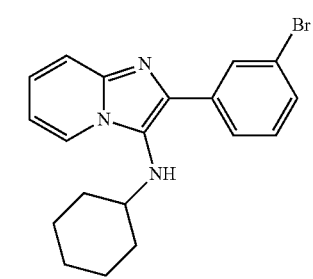
DG 402-49650
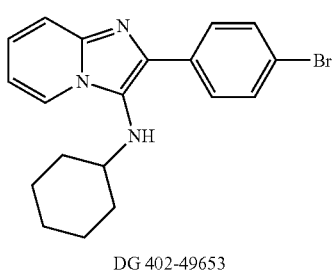
DG 402-49653
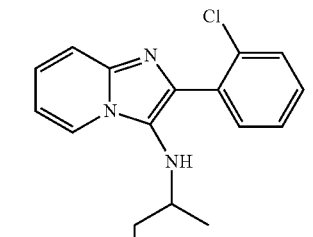
DG 402-49655
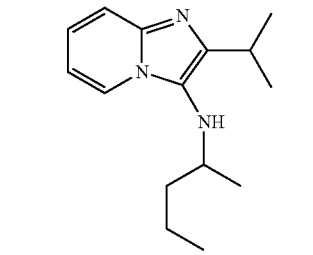
DG 402-49657

-continued
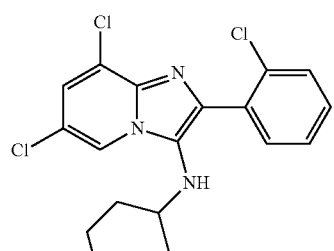
DG 402-49667
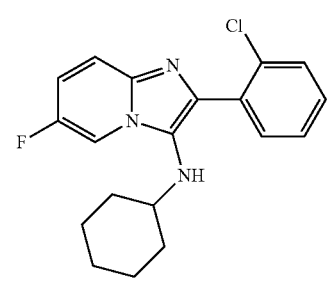
DG 402-49663
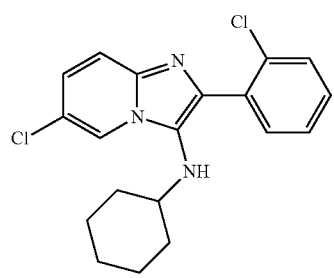
DG 402-49665
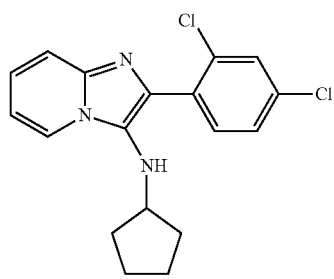
DG 402-49672
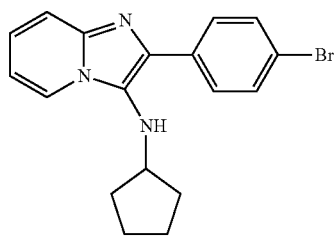
DG 402-49673
-continued
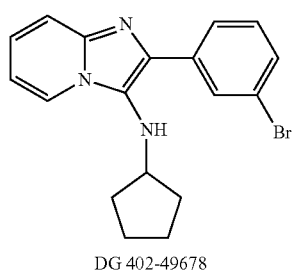
DG 402-49678
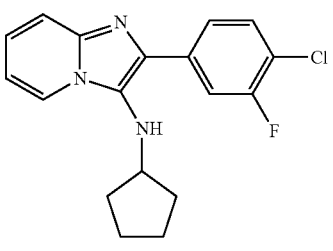
DG 402-49679
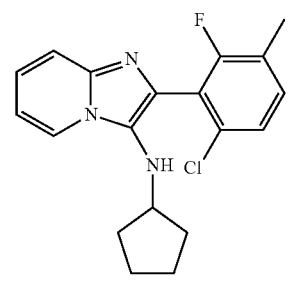
DG 402-49680
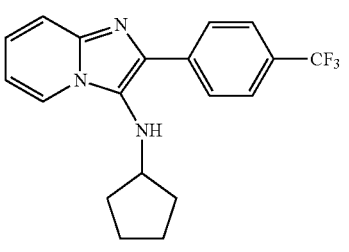
DG 402-49681
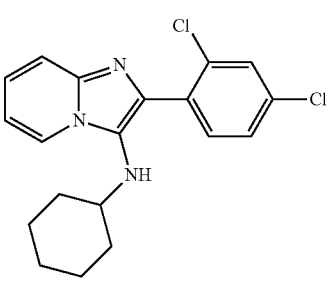
DG 402-49686

| | |
|---|---|
| 90<br>DG 402-49688 | 94<br>DG 402-49700 |
| 91<br>DG 402-49690 | 95<br>DG 402-49702 |
| 92<br>DG 402-49683 | 96<br>DG 402-49704 |
| 93<br>DG 402-49694 | 97<br>DG 402-49754 |
| | 98<br>DG 402-49708 |

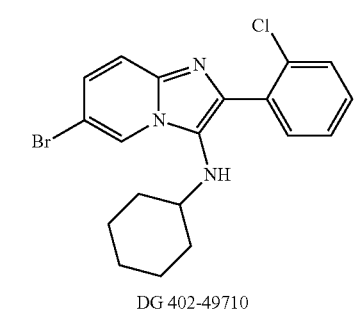
DG 402-49710
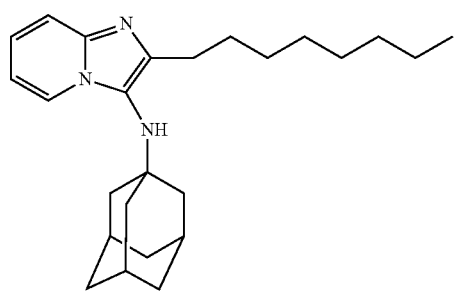
DG 402-49692
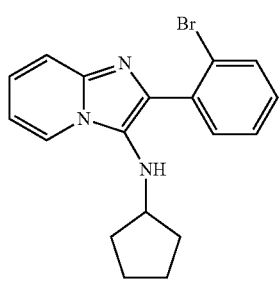 [SMILES: Clc1ccccc1-c1nc2ccccn2c1NC1CCCC1]
DG 402-49675
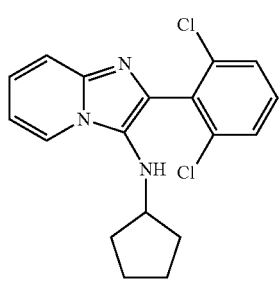
DG 402-49682
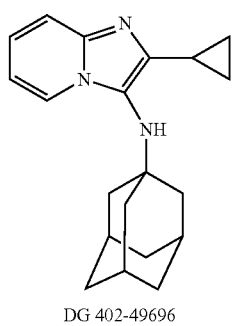
DG 402-49696
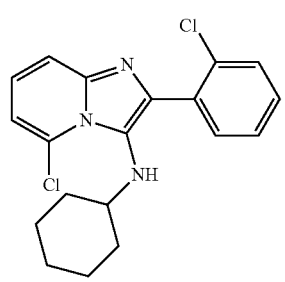
DG 402-49748
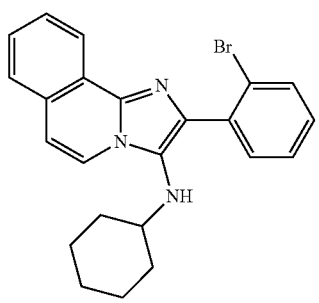
DG 402-49758
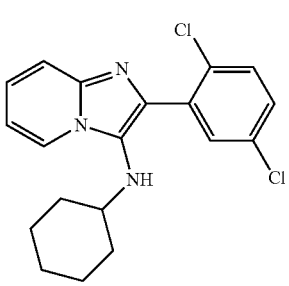
SG389-832C
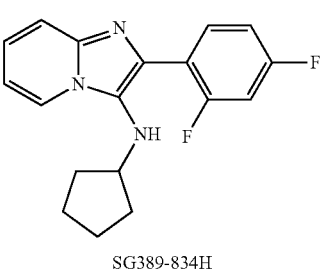
SG389-834H
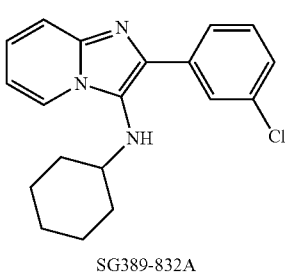
SG389-832A -continued
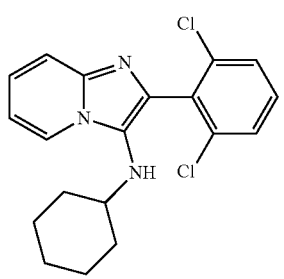
SG389-832D
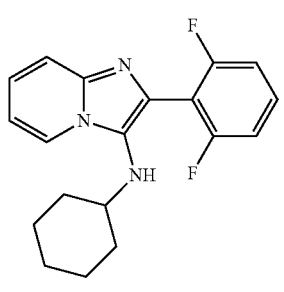
SG389-832E
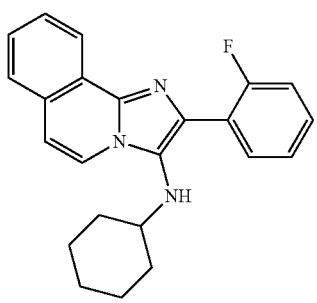
DG 402-49756
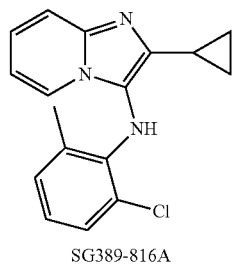
SG389-816A
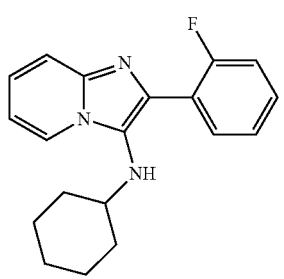
SG389-832B
-continued
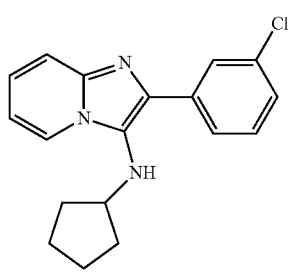
SG389-834A
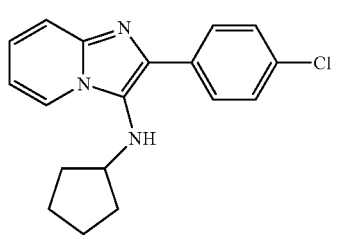
SG389-834C
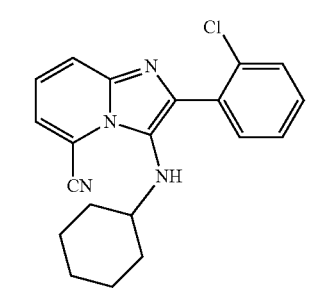
CW23836
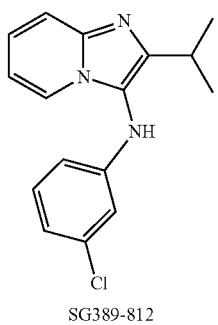
SG389-812
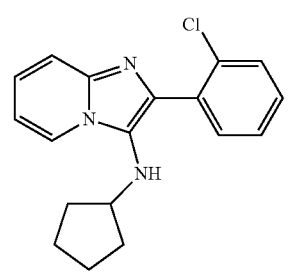
SG389-834B 119
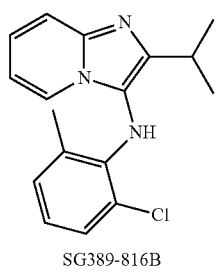
SG389-816B
120
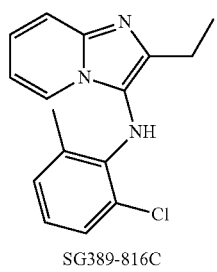
SG389-816C
121
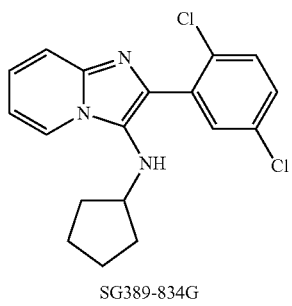
SG389-834G
122
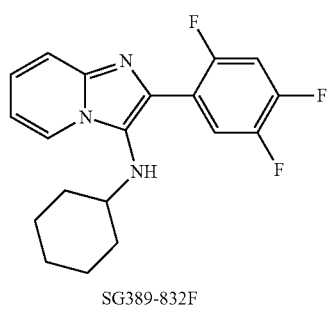
SG389-832F
123
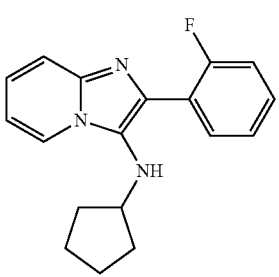
SG389-834E
124
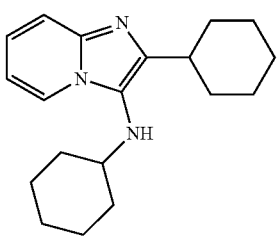
SM60
125
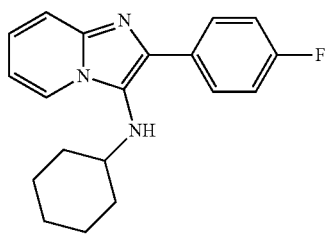
SM2
126
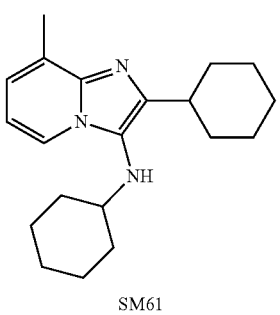
SM61
127
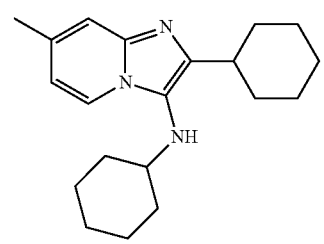
SM62
128
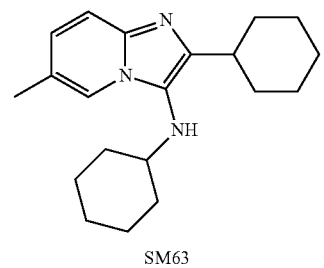
SM63

-continued
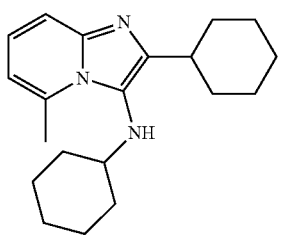
SM64
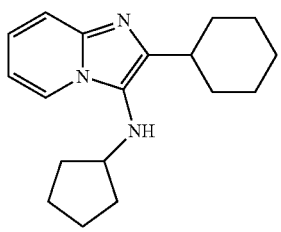
SM66
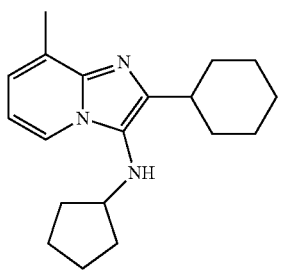
SM67
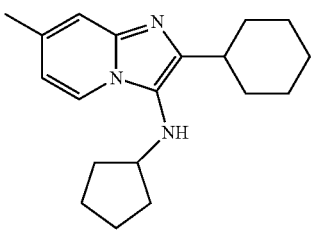
SM68
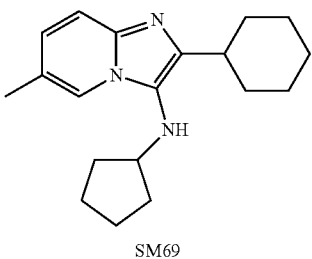
SM69
-continued
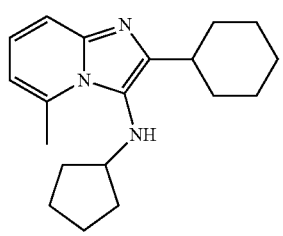
SM70
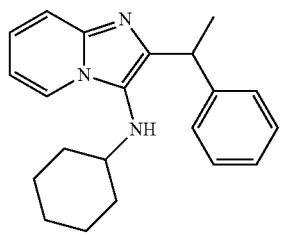
SM52
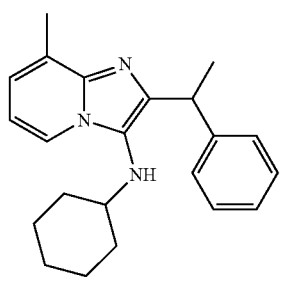
SM53
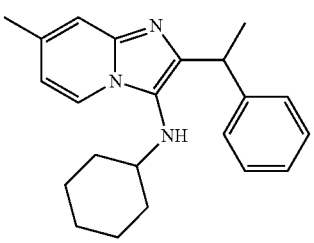
SM54
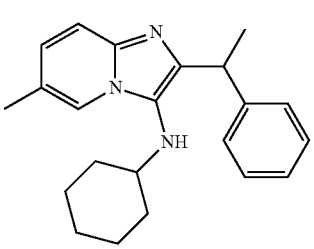
SM55

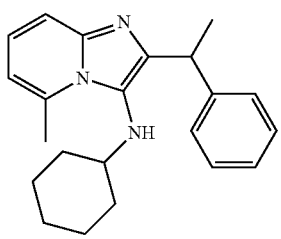
SM56
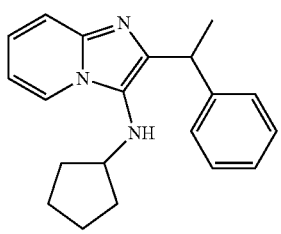
SM51
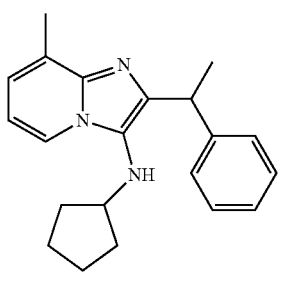
SM72
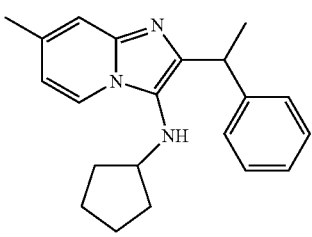
SM73
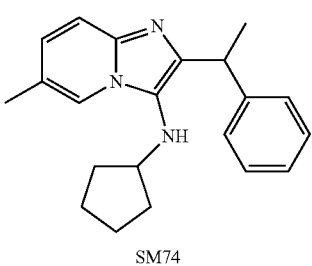
SM74
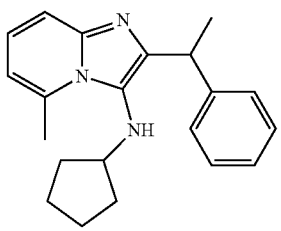
SM75
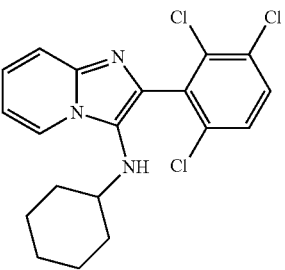
SM3
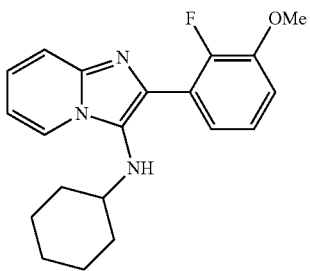
SM4
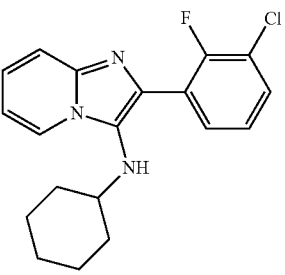
SM6
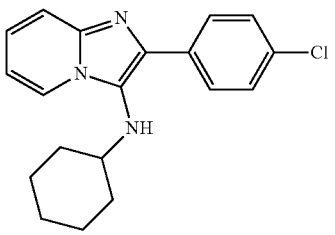
SM7

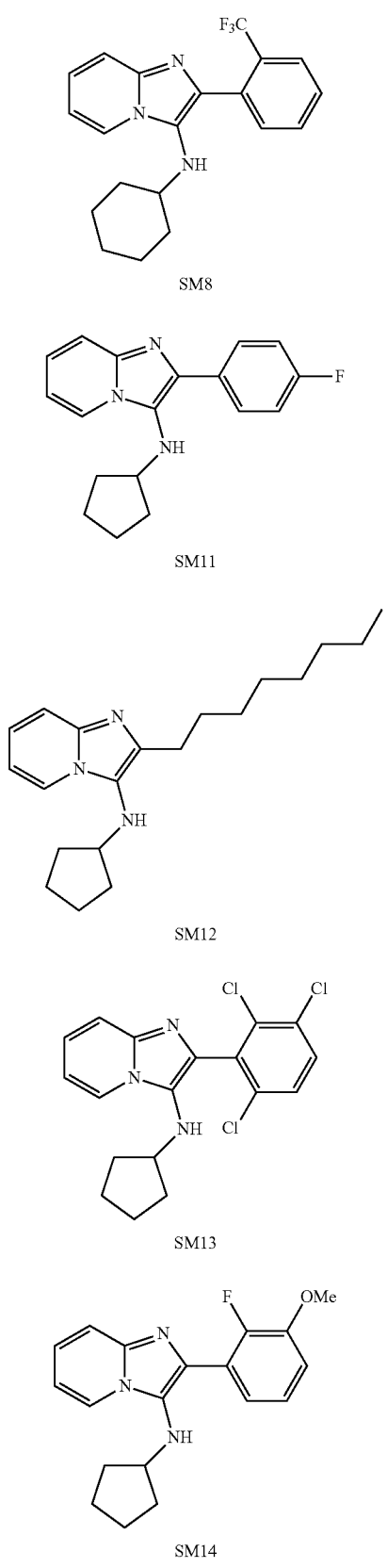
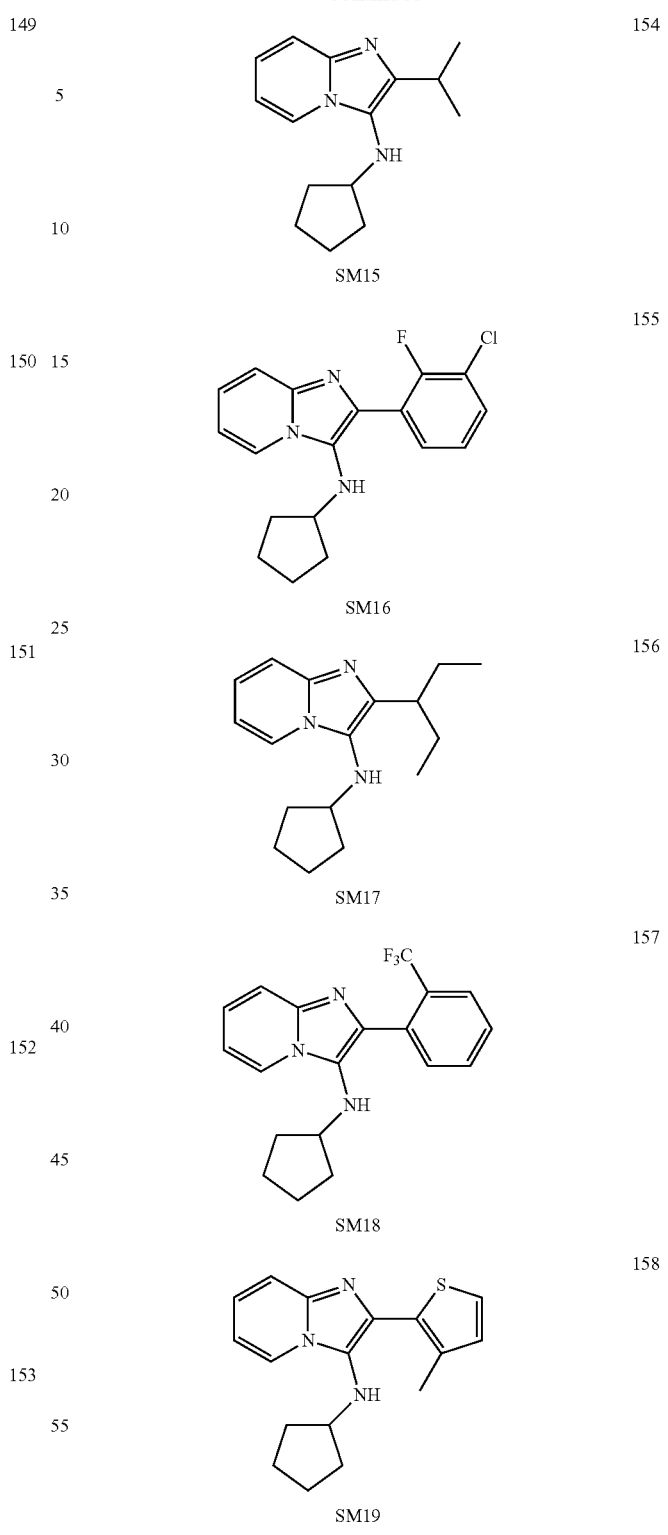

-continued
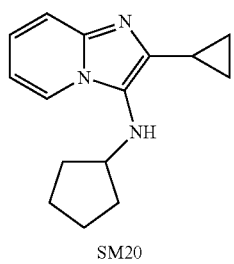
SM20
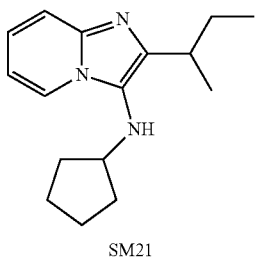
SM21
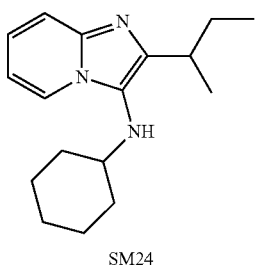
SM24
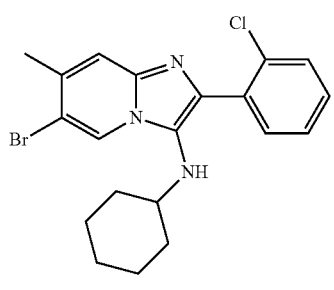
SM26
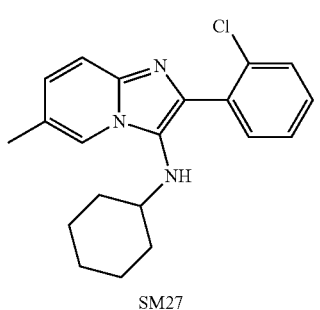
SM27
-continued
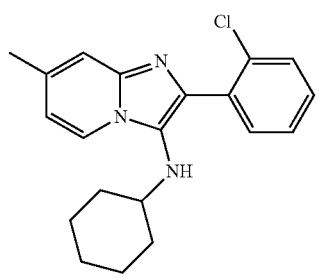 [SMILES: Cc1ccc2nc(-c3ccccc3Cl)c(NC3CCCCC3)n2c1]
SM28
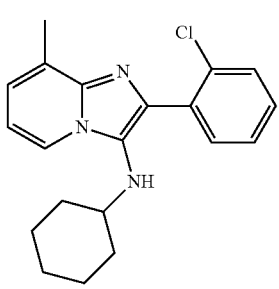 [SMILES: Cc1cccn2c(NC3CCCCC3)c(-c3ccccc3Cl)nc12]
SM29
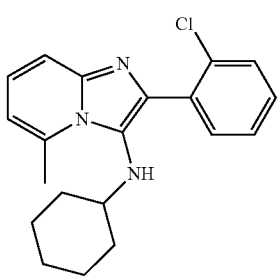
SM30
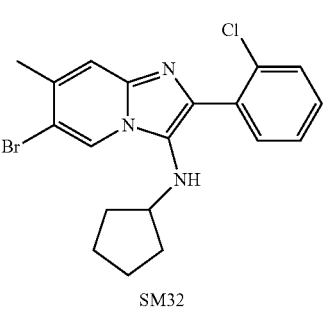
SM32
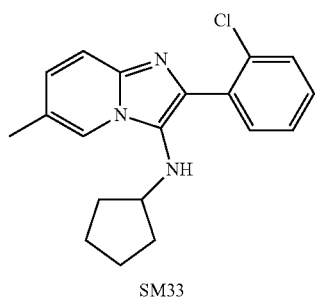
SM33

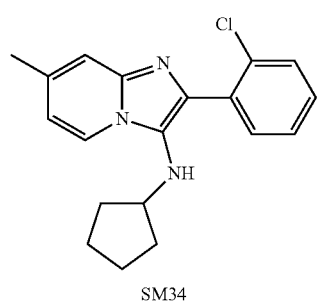
SM34
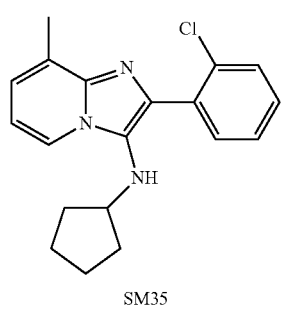
SM35
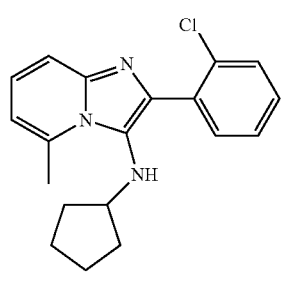
SM36
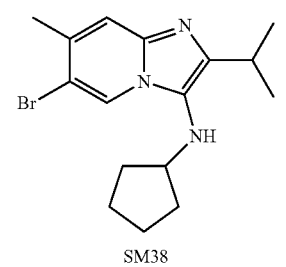
SM38
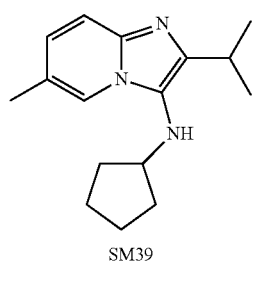
SM39
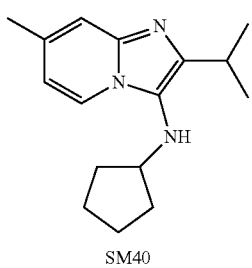
SM40
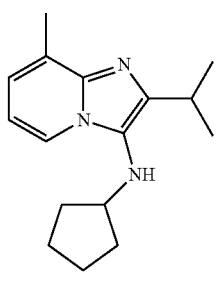
SM41
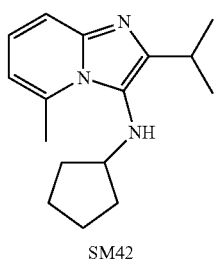
SM42
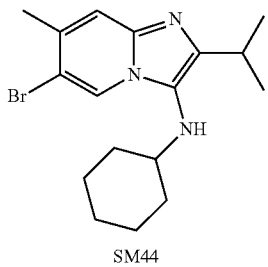
SM44
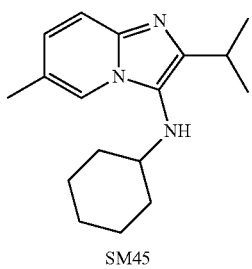
SM45

-continued
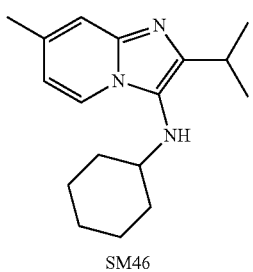
SM46
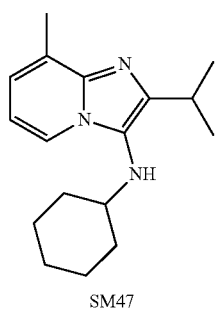
SM47
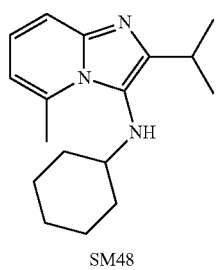
SM48
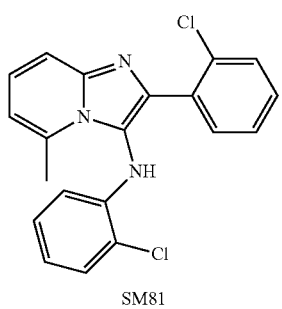
SM81
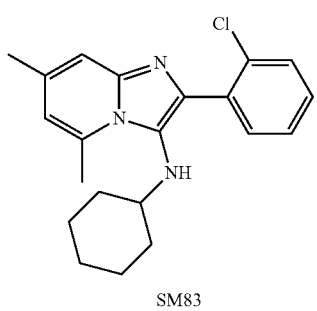
SM83
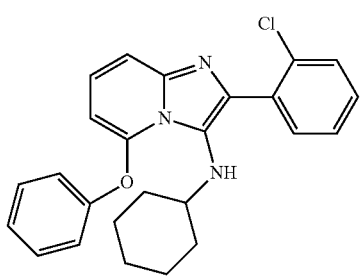
SM92
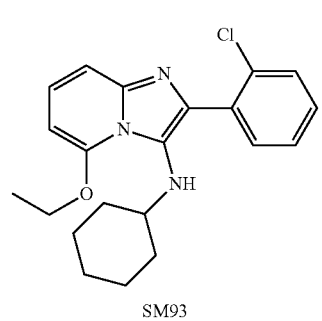
SM93
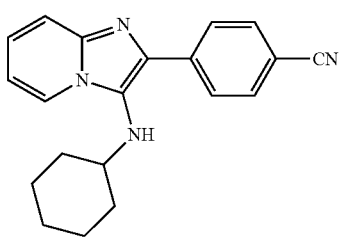
DG402-49720
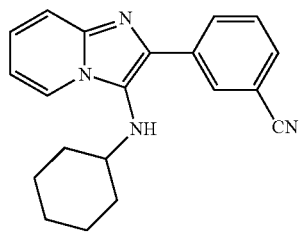
DG402-49722
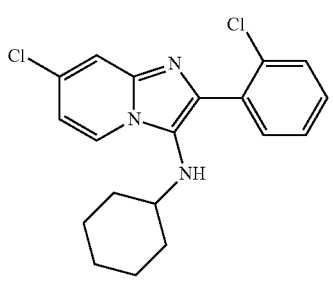
DG402-49744

-continued

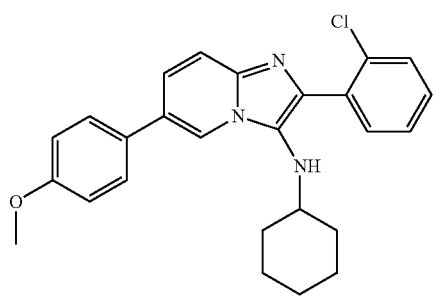

CW23828a

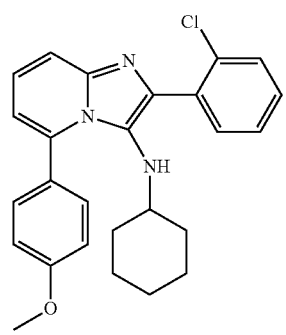

CW23828b

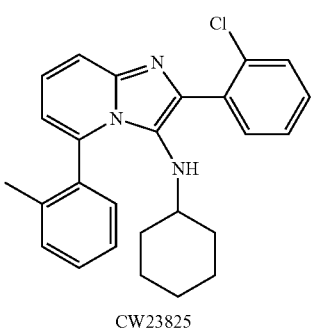

CW23825

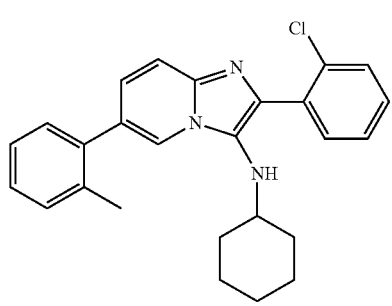

CW23828c

-continued

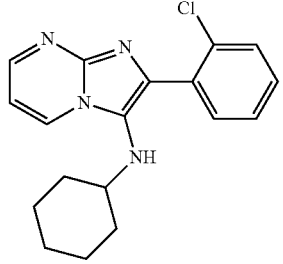 [SMILES: Clc1ccccc1-c1nc2ccccn2c1NC1CCCCC1]

DG402-49750

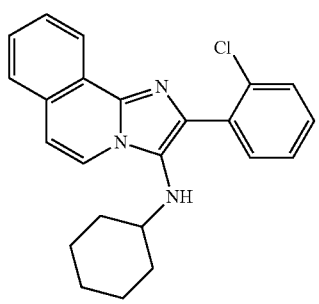

DG 402-49752

The invention is now described, by way of example with reference to the following Examples.

All compounds were prepared by one of four methods

METHOD 1

The appropriate 2-aminopyridine (1.33 mmol), aldehyde (1.33 mmol) and isocyanide (1.36 mmol) in dioxane (2.5 ml) were heated in the presence of montmorillonite K-10 clay (250 mg) for 5-8 h at 95-100° C. After reaction, the liquid was filtered from the clay and the clay was rinsed with dioxane or ethyl acetate (2×2.5 ml). The solvent was removed in vacuo and the residue purified by column chromatography (elution hexane:ethyl acetate) to afford the required product.

Method 1 applies to compounds: 1-15, 17-31, 33-41, 43, 49-64, 67-77, 106-110, 112-115 and 117-183.

METHOD 2

As for method 1, but instead of heating, the reaction was stirred at room temperature for 48 h.

Method 2 applies to compounds: 45-47

METHOD 3

As for method 1, but instead of conventional heating, reaction components were reacted under microwave irradiation at 150 W and 100° C. for 15-30 min in a sealed pressure tube.

Method 3 applies to compounds: 42, 44, 48, 65, 66, 78-105, 111, 116, 186-194. In the case of the pyrimidine 193, the appropriate 2-aminopyrimidine (1.33 mmol) and aldehyde (2.66 mmol) were microwaved at 150 W power and 150° C. for 35 min without solvent. Isocyanide (1.60 mmol), dioxane (1.5 ml) and montmorillonite K-10 clay (250 mg) were then added and irradiated at 150 W and 100° C. for 25 min. After reaction, the liquid was filtered from the clay and the clay was rinsed with dioxane or ethyl acetate.

The solvent was removed in vacuo and the residue purified by column chromatography (elution ethyl acetate) to afford the required product.

METHOD 4

Imidazo[1,2-a]pyridines prepared by method 1 or 3 were further modified to produce compounds 16, 32, 184 and 185. Preparations are described below.

N-butyl-N-(2-isopropylimidazo[1,2-a]pyridin-3-yl)acetamide 16

N-butyl-2-isopropylimidazo[1,2-a]pyridin-3-amine 5 (250 mg, 1.08 mmol) was reacted with acetyl chloride (2 eq., 2.16 mmol, 154 µl) in the presence of $K_2CO_3$ (2 eq., 2.16 mmol, 299 mg) in acetonitrile (10 ml) at room temperature. The reaction progress was monitored by TLC. Purification of the product was achieved by column chromatography, eluting with ethyl acetate:hexane.

N-butyl-N-ethyl-2-isopropylimidazo[1,2-a]pyridin-3-amine 32

N-butyl-N-(2-isopropylimidazo[1,2-a]pyridin-3-yl)acetamide 16 (287 mg, 1.05 mmol) was reacted with $LiAlH_4$ (2 eq., 2.10 mmol, 80 mg) in THF (10 ml) at room temperature. Progress of the reaction was monitored by TLC. Aqueous NaOH solution was used to quench the reaction. Solids were filtered and washed with ethyl acetate and the product was purified by column chromatography, eluting with ethyl acetate.

2-(2-chlorophenyl)-N-cyclohexyl-5-phenoxyimidazo[1,2-a]pyridin-3-amine 184

Phenol (40.43 mg, 0.687 mmol) was dissolved in DMF (5 ml) and sodium metal (10.31 mg, 0.687 mmol) was added portion-wise. 5-Bromo-2-(2-chlorophenyl)-N-cyclohexylimidazo[1,2-a]pyridin-3-amine 42 (139.1 mg, 0.344 mmol) was added to this sodium phenoxide solution and heated at 90° C. for 4 h. The reaction was quenched with water and extracted into ethyl acetate. The product was purified by column chromatography, elution ethyl acetate:hexane.

2-(2-chlorophenyl)-N-cyclohexyl-5-ethoxyimidazo[1,2-a]pyridin-3-amine 185

5-bromo-2-(2-chlorophenyl)-N-cyclohexylimidazo[1,2-a]pyridin-3-amine 42 (152 mg, 0.376 mmol) was added to sodium ethoxide [generated in situ by addition of sodium metal (17.32 mg) to absolute ethanol (10 ml)]. The mixture was heated under reflux for 8 h. Excess solvent was removed in vacuo and the resultant mixture was treated with water before been extracted into ethyl acetate, dried over magnesium sulphate and filtered. Excess solvent was removed under reduced pressure to give an oil that was purified by column chromatography, eluting with hexane:ethyl acetate.

The analytical data of compounds 1-194 are set out below.

1 MLB133-607A N-cyclohexyl-2-cyclopropylimidazo[1,2-a]pyridin-3-amine $^1$H NMR (200 MHz, $CDCl_3$) δ 8.05-7.94 (m, 1H), 7.46-7.33 (m, 1H), 7.01 (ddd, J=1.3, 6.7, 9.0, 1H), 6.69 (td, J=1.0, 6.7, 1H), 3.07-2.67 (m, 2H), 2.11-1.82 (m, 3H), 1.82-1.67 (m, 2H), 1.67-1.48 (m, 1H), 1.41-1.10 (m, 5H), 1.05 (dt, J=4.1, 5.2, 2H), 1.01-0.85 (m, 2H).

$^{13}$C NMR (50 MHz, $CDCl_3$) δ 141.22, 140.49, 124.82, 122.67, 121.94, 116.62, 110.82, 57.24, 34.37, 25.85, 24.94, 8.18, 7.73.

HRMS (ESI): m/z 256.1810 (M+H)$^+$; calc. for $C_{16}H_{22}N_3$: 256.1814.

2 MLB133-607C N-cyclohexyl-2-(2-(methylthio)ethyl)imidazo[1,2-a]pyridin-3-amine $^1$H NMR (200 MHz, $CDCl_3$) δ 8.10-7.94 (m, 1H), 7.48-7.38 (m, 1H), 7.06 (ddd, J=1.3, 6.6, 9.0, 1H), 6.72 (td, J=1.1, 6.8, 1H), 3.20-2.78 (m, 6H), 2.18-2.00 (m, 3H), 1.76 (ddt, J=6.2, 10.2, 18.4, 5H), 1.41-1.03 (m, 5H).

$^{13}$C NMR (50 MHz, $CDCl_3$) δ 141.43, 137.54, 125.25, 123.10, 122.53, 116.90, 111.11, 57.16, 34.43, 34.35, 27.81, 25.79, 24.91, 15.87.

HRMS (ESI): m/z 290.1684 (M+H)$^+$; calc. for $C_{16}H_{24}N_3S$: 290.1691.

3 MLB133-608A 2-sec-butyl-N-cyclohexylimidazo[1,2-a]pyridin-3-amine $^1$H NMR (200 MHz, $CDCl_3$) δ 8.14-7.93 (m, 1H), 7.48 (dt, J=1.3, 9.5, 1H), 7.04 (ddd, J=1.2, 6.7, 8.8, 1H), 6.71 (td, J=1.1, 6.9, 1H), 3.10-2.63 (m, 2H), 2.12-1.48 (m, 9H), 1.48-1.06 (m, 10H), 1.06-0.90 (m, 2H), 0.85 (t, J=7.3, 3H).

$^{13}$C NMR (50 MHz, $CDCl_3$) δ 143.77, 141.75, 124.39, 123.01, 122.71, 117.13, 111.12, 57.58, 34.55, 34.51, 33.63, 30.16, 26.09, 25.23, 25.15, 21.07, 12.87.

HRMS (ESI): m/z 272.2127 (M+H)$^+$; calc. for $C_{17}H_{26}N_3$: 272.2127.

4 MLB133-609A N-cyclohexyl-2-(5-methylisoxazol-3-yl)imidazo[1,2-a]pyridin-3-amine $^1$H NMR (200 MHz, $CDCl_3$) δ 8.01 (d, J=6.9, 1H), 7.52 (d, J=9.1, 1H), 7.18-7.05 (m, 1H), 6.78 (td, J=0.7, 6.8, 1H), 6.63-6.55 (m, 1H), 4.79-3.86 (m, 1H), 3.17-2.91 (m, 1H), 2.48 (s, 3H), 2.03-1.46 (m, 5H), 1.46-0.91 (m, 5H).

$^{13}$C NMR (50 MHz, $CDCl_3$) δ 168.61, 159.55, 141.64, 129.39, 123.54, 123.02, 117.87, 111.94, 100.67, 56.38, 34.07, 25.70, 25.08, 12.21.

HRMS (ESI): m/z 297.1701 (M+H)$^+$; calc. for $C_{17}H_{21}N_4O$: 297.1715.

5 MLB133-616C
N-butyl-2-isopropylimidazo[1,2-a]pyridin-3-amine $^1$H NMR (200 MHz, $CDCl_3$) δ 7.92 (d, J=6.8, 1H), 7.56-7.30 (m, 1H), 6.97 (ddd, J=0.9, 6.7, 8.6, 1H), 6.64 (td, J=0.6, 6.7, 1H), 3.24-2.97 (m, 1H), 2.90 (t, J=6.8, 3H), 1.65-1.34 (m, 4H), 1.30 (d, J=6.9, 6H), 0.87 (t, J=7.1, 3H).

$^{13}$C NMR (50 MHz, $CDCl_3$) δ 143.98, 141.19, 124.52, 122.64, 122.08, 117.08, 110.96, 48.96, 32.90, 26.45, 22.80, 20.22, 13.92.

HRMS (ESI): m/z 232.1808 (M+H)$^+$; calc. for $C_{14}H_{22}N_3$: 232.1814.

6 MLB133-623B N-cyclohexyl-2-isopropylimidazo[1,2-a]pyridin-3-amine $^1$H NMR (200 MHz, $CDCl_3$) δ 8.02 (d, J=6.8, 1H), 7.49 (d, J=8.9, 1H), 7.07-6.95 (m, 1H), 6.72 (dd, J=3.7, 9.7, 1H), 3.31-3.01 (m, 1H), 2.85 (ddd, J=5.2, 7.7, 10.2, 2H), 2.00-1.51 (m, 5H), 1.36 (d, J=6.9, 6H), 1.22 (dt, J=7.3, 12.7, 5H).

$^{13}$C NMR (50 MHz, CDCl$_3$) δ 144.66, 141.40, 123.06, 122.76, 122.44, 117.00, 110.94, 57.23, 34.30, 26.20, 25.85, 24.95, 22.83.

HRMS (ESI): m/z 258.1963 (M+H)$^+$; calc. for C$_{16}$H$_{24}$N$_3$: 258.1970.

7 MLB133-624B 6-chloro-N-cyclohexyl-2-isopropylimidazo[1,2-a]pyridin-3-amine $^1$H NMR (200 MHz, CDCl$_3$) δ 8.11-7.98 (m, 1H), 7.51-7.34 (m, 1H), 7.00 (ddd, J=0.7, 2.1, 9.5, 1H), 3.26-2.99 (m, 1H), 2.99-2.65 (m, 2H), 2.11-1.52 (m, 5H), 1.48-1.28 (m, 6H), 1.28-1.07 (m, 5H).

$^{13}$C NMR (50 MHz, CDCl$_3$) δ 146.07, 139.73, 124.02, 123.66, 120.39, 119.45, 117.36, 57.23, 34.26, 26.28, 25.78, 24.91, 22.72.

HRMS (ESI): m/z 292.1581 (M+H)$^+$; calc. for C$_{16}$H$_{23}$N$_3$Cl: 292.1581.

8 MLB133-641A 2-(2-chlorophenyl)-N-cyclohexylimidazo[1,2-a]pyridin-3-amine $^1$H NMR (200 MHz, CDCl$_3$) δ 8.17 (dt, J=1.0, 6.9, 1H), 7.70 (dd, J=3.0, 6.4, 1H), 7.62-7.52 (m, 1H), 7.52-7.29 (m, 3H), 7.16 (ddd, J=1.1, 6.6, 9.0, 1H), 6.82 (td, J=0.9, 6.7, 1H), 3.29 (d, J=6.7, 1H), 2.68 (s, 1H), 1.88-1.31 (m, 5H), 1.30-0.77 (m, 5H).

$^{13}$C NMR (50 MHz, CDCl$_3$) δ 141.56, 135.04, 133.98, 132.56, 129.42, 129.07, 126.86, 126.33, 123.66, 122.83, 117.52, 111.55, 56.41, 33.87, 25.67, 24.60.

HRMS (ESI): m/z 326.1440 (M+H)$^+$; calc. for C$_{19}$H$_{21}$N$_3$Cl: 326.1424.

9 MLB133-628A N-cyclohexyl-2-ethylimidazo[1,2-a]pyridin-3-amine $^1$H NMR (200 MHz, CDCl$_3$) δ 8.01 (d, J=6.8, 1H), 7.45 (d, J=9.2, 1H), 7.17-6.89 (m, 1H), 6.71 (t, J=6.8, 1H), 2.75 (m+dd, J=7.6, 15.1, 4H), 2.08-1.46 (m, 5H), 1.34 (t, J=7.5, 3H), 1.27-1.02 (m, 5H).

$^{13}$C NMR (50 MHz, CDCl$_3$) δ 141.52, 140.82, 124.27, 123.22, 122.67, 117.02, 111.34, 57.42, 34.55, 26.09, 25.18, 20.74, 14.26.

HRMS (ESI): m/z 244.1809 (M+H)$^+$; calc. for C$_{15}$H$_{22}$N$_3$: 244.1814.

10 MLB133-616B 2-isopropyl-N-(2,4,4-trimethylpentan-2-yl)imidazo[1,2-a]pyridin-3-amine $^1$H NMR (200 MHz, CDCl$_3$) δ 8.15 (d, J=6.7, 1H), 7.47 (d, J=9.0, 1H), 7.17-6.91 (m, 1H), 6.68 (t, J=6.7, 1H), 3.32-2.96 (m, 1H), 2.96-2.37 (m, 1H), 1.35 (d, J=6.8, 6H), 1.15 (d, J=8.1, 6H), 1.07 (d, J=10.9, 10H).

$^{13}$C NMR (50 MHz, CDCl$_3$) δ 146.77, 142.18, 123.36, 122.99, 121.43, 116.91, 110.57, 59.26, 56.93, 31.97, 31.82, 29.23, 26.12, 22.89.

HRMS (ESI): m/z 288.2426 (M+H)$^+$; calc. for C$_{18}$H$_{30}$N$_3$: 288.2440.

11 MLB133-616A 2-isopropyl-N-pentylimidazo[1,2-a]pyridin-3-amine $^1$H NMR (200 MHz, CDCl$_3$) δ 7.98 (d, J=6.8, 1H), 7.48 (d, J=9.0, 1H), 7.04 (ddd, J=6.5, 8.5, 1H), 6.71 (t, J=6.9, 1H), 3.20-3.05 (m, 2H), 2.96 (t, J=7.0, 2H), 1.58 (ddd, J=3.7, 7.9, 14.3, 2H), 1.42-1.10 (m, 10H), 0.90 (t, J=7.0, 3H).

$^{13}$C NMR (50 MHz, CDCl$_3$) δ 143.89, 141.17, 124.52, 122.69, 122.08, 117.05, 111.00, 49.25, 30.50, 29.23, 26.44, 22.79, 22.55, 14.02.

HRMS (ESI): m/z 246.1950 (M+H)$^+$; calc. for C$_{15}$H$_{24}$N$_3$: 246.1970.

12 MLB133-640A 4-(3-(cyclohexylamino)imidazo[1,2-a]pyridin-2-yl)-2-ethoxyphenol $^1$H NMR (200 MHz, CDCl$_3$) δ 8.09 (d, J=6.9, 1H), 7.74-7.60 (m, 1H), 7.60-7.37 (m, 2H), 7.20-7.03 (m, 1H), 6.98 (d, J=8.2, 1H), 6.75 (t, J=7.1, 1H), 4.35-4.04 (m, 3H), 3.36-2.68 (m, 2H), 1.95-1.52 (m, 5H), 1.45 (t, J=6.9, 3H), 1.37-0.97 (m, 5H).

$^{13}$C NMR (50 MHz, CDCl$_3$) δ 146.08, 145.42, 141.38, 136.83, 126.87, 124.06, 123.53, 122.54, 119.92, 117.13, 114.30, 111.34, 111.17, 64.60, 56.83, 34.24, 25.79, 24.85, 15.00.

HRMS (ESI): m/z 352.2025 (M+H)$^+$; calc. for C$_{21}$H$_{26}$N$_3$O$_2$: 352.2025.

13 MLB133-635C 2-cyclopropyl-5,7-dimethyl-N-(naphthalen-2-yl)imidazo[1,2-a]pyridin-3-amine $^1$H NMR (200 MHz, CDCl$_3$) δ 7.73 (d, J=8.7, 2H), 7.55 (d, J=8.2, 1H), 7.46-7.07 (m, 3H), 6.94 (dd, J=2.3, 8.8, 1H), 6.73 (d, J=1.4, 1H), 6.26 (s, 1H), 5.58 (s, 1H), 2.62 (s, 3H), 2.33 (s, 3H), 1.94 (ddd, J=5.1, 8.5, 13.5, 1H), 1.16-0.97 (m, 2H), 0.87 (ddd, J=3.8, 6.3, 11.8, 2H).

$^{13}$C NMR (50 MHz, CDCl$_3$) δ 145.76, 145.18, 144.78, 135.27, 134.89, 134.43, 129.52, 128.25, 127.63, 126.48, 126.12, 122.70, 118.67, 116.19, 115.53, 113.68, 107.06, 20.93, 18.76, 7.83, 7.54.

HRMS (ESI): m/z 328.1803 (M+H)$^+$; calc. for C$_{22}$H$_{22}$N$_3$: 328.1814.

14 MLB133-627A N-isopropyl-2-(4-methoxyphenyl)imidazo[1,2-a]pyridin-3-amine $^1$H NMR (200 MHz, CDCl$_3$) δ 8.14-8.05 (m, 1H), 7.97 (d, J=8.9, 2H), 7.51 (dd, J=0.5, 8.9, 1H), 7.17-7.04 (m, 1H), 6.98 (d, J=8.9, 2H), 6.74 (td, J=0.9, 6.7, 1H), 3.84 (s, 3H), 3.40 (td, J=7.2, 13.1, 1H), 3.16-2.79 (m, 1H), 1.08 (d, J=6.3, 6H).

$^{13}$C NMR (50 MHz, CDCl$_3$) δ 158.95, 141.59, 138.21, 128.31, 127.21, 123.61, 122.54, 117.22, 113.95, 111.34, 55.28, 49.12, 23.45.

HRMS (ESI): m/z 282.1602 (M+H)$^+$; calc. for C$_{17}$H$_{20}$N$_3$O: 282.1606.

15 MLB133-640C N-cyclohexyl-5,7-dimethyl-2-propylimidazo[1,2-a]pyridin-3-amine $^1$H NMR (200 MHz, CDCl$_3$) δ 7.05 (s, 1H), 6.20 (s, 1H), 2.83 (s, 3H), 2.61 (dd, J=8.7, 16.6, 4H), 2.28 (s, 3H), 1.98-1.50 (m, 7H), 1.16 (s, 5H), 0.98 (t, J=7.3, 3H).

$^{13}$C NMR (50 MHz, CDCl$_3$) δ 143.53, 140.95, 135.08, 133.70, 125.46, 115.34, 113.67, 59.57, 33.61, 29.74, 26.01, 25.17, 22.71, 20.77, 19.51, 14.33.

HRMS (ESI): m/z 286.2284 (M+H)$^+$; calc. for C$_{18}$H$_{28}$N$_3$: 286.2283.

16 DG120-034 N-butyl-N-(2-isopropylimidazo[1,2-a]pyridin-3-yl)acetamide $^1$H NMR (200 MHz, DMSO-d$_6$) δ 8.13 (d, J=6.3, 1H), 7.55 (d, J=9.3, 1H), 7.45-7.19 (m, 1H), 6.96 (t, J=6.7, 1H), 3.73-

3.26 (m, 11H), 3.10-2.78 (m, 1H), 2.65-2.42 (m, 1H), 1.73 (s, 1H), 1.63 (s, 2H), 1.54-1.32 (m, 3H), 1.26 (t, J=6.7, 6H), 0.82 (t, J=6.9, 3H).
$^{13}$C NMR (50 MHz, DMSO-$d_6$) δ 175.26, 171.14, 170.96, 146.57, 141.97, 124.82, 122.51, 118.46, 116.80, 112.58, 47.01, 30.61, 29.99, 25.61, 24.08, 22.44, 22.01, 21.82, 21.74, 20.74, 19.56, 13.59.

17 MLB133-628B N,2-bis(4-methoxyphenyl)imidazo[1,2-a]pyridin-3-amine $^1$H NMR (200 MHz, DMSO-$d_6$) δ 8.13-7.79 (m, 3H), 7.55 (dd, J=8.8, 14.7, 1H), 7.39-7.16 (m, 1H), 7.04-6.83 (m, 3H), 6.76 (d, J=8.8, 2H), 6.45 (d, J=8.8, 2H), 3.77 (s, 3H), 3.64 (s, 3H).
$^{13}$C NMR (50 MHz, DMSO-$d_6$) δ 158.66, 152.22, 141.40, 139.19, 139.12, 137.35, 127.65, 126.18, 124.64, 122.81, 116.70, 114.97, 113.79, 113.41, 111.83, 55.19, 55.03.
HRMS (ESI): m/z 346.1548 (M+H)$^+$; calc. for $C_{21}H_{20}N_3O_2$: 346.1556.

18 MLB133-615B N-benzyl-2-isopropylimidazo[1,2-a]pyridin-3-amine $^1$H NMR (200 MHz, CDCl$_3$) δ 7.99 (d, J=6.8, 1H), 7.52 (d, J=8.9, 1H), 7.35 (s, 5H), 7.19-6.97 (m, 1H), 6.72 (t, J=6.7, 1H), 4.15 (d, J=3.7, 2H), 3.35-3.17 (m, 1H), 3.17-2.94 (m, 1H), 1.33 (d, J=6.9, 6H).
$^{13}$C NMR (50 MHz, CDCl$_3$) δ 144.54, 141.34, 139.39, 128.60, 128.22, 127.54, 123.84, 122.89, 122.05, 117.14, 111.10, 53.33, 26.49, 22.74.
HRMS (ESI): m/z 266.1637 (M+H)$^+$; calc. for $C_{17}H_{20}N_3$: 266.1657.

19 MLB133-607B N-cyclohexyl-2-cyclopentylimidazo[1,2-a]pyridin-3-amine $^1$H NMR (200 MHz, CDCl$_3$) δ 8.01 (d, J=7.3, 1H), 7.49 (d, J=9.0, 1H), 7.17-6.92 (m, 1H), 6.71 (t, J=6.8, 1H), 3.34-3.03 (m, 1H), 3.02-2.64 (m, 2H), 2.12-1.82 (m, 8H), 1.82-1.44 (m, 5H), 1.44-1.00 (m, 5H).
$^{13}$C NMR (50 MHz, CDCl$_3$) δ 142.71, 141.52, 124.07, 122.63, 122.31, 116.99, 110.83, 57.19, 37.61, 34.33, 33.53, 26.04, 25.88, 25.00.
HRMS (ESI): m/z 284.2125 (M+H)$^+$; calc. for $C_{18}H_{26}N_3$: 284.2127.

20 MLB133-615C 2-isopropyl-N-(naphthalen-2-yl)imidazo[1,2-a]pyridin-3-amine $^1$H NMR (200 MHz, CDCl$_3$) δ 7.93-7.79 (m, 1H), 7.73 (d, J=8.7, 2H), 7.69-7.58 (m, 1H), 7.51 (d, J=8.1, 1H), 7.43-7.12 (m, 3H), 6.95 (dd, J=2.4, 8.8, 1H), 6.72 (td, J=1.1, 6.8, 1H), 6.66 (d, J=2.2, 1H), 5.73 (s, 1H), 3.37-3.03 (m, 1H), 1.37 (d, J=6.9, 6H).
$^{13}$C NMR (50 MHz, CDCl$_3$) δ 148.20, 143.18, 142.59, 134.74, 129.56, 128.42, 127.63, 126.54, 126.07, 124.12, 122.90, 122.44, 117.36, 116.97, 116.27, 111.68, 106.69, 26.79, 22.31.
HRMS (ESI): m/z 302.1640 (M+H)$^+$; calc. for $C_{20}H_{20}N_3$: 302.1657.

21 MLB133-608C N-cyclohexyl-2-(2,5-dimethoxytetrahydrofuran-3-yl)imidazo[1,2-a]pyridin-3-amine $^1$H NMR (200 MHz, CDCl$_3$) δ 8.09-7.90 (m, 1H), 7.53-7.37 (m, 1H), 7.15-6.95 (m, 1H), 6.80-6.64 (m, 1H), 5.40-4.99 (m, 2H), 3.81-3.62 (m, 1H), 3.44 (dd, J=4.2, 10.4, 6H), 3.04 (dd, J=5.3, 10.8, 1H), 2.85 (td, J=5.5, 9.5, 1H), 2.72-2.41 (m, 1H), 2.41-2.19 (m, 1H), 1.99-1.37 (m, 5H), 1.17 (dq, J=7.5, 13.3, 5H).
$^{13}$C NMR (50 MHz, CDCl$_3$) δ 147.44, 141.52, 138.14, 137.54, 136.67, 125.76, 123.16, 122.83, 122.49, 122.25, 117.18, 117.03, 116.85, 113.69, 111.51, 111.17, 109.68, 109.13, 105.97, 105.38, 104.83, 104.50, 57.13, 57.08, 56.13, 55.74, 54.92, 42.71, 41.75, 38.71, 36.36, 34.34, 34.18, 34.11, 25.73, 25.01, 24.89, 24.85.
HRMS (ESI): m/z 346.2094 (M+H)$^+$; calc. for $C_{19}H_{28}N_3O_3$: 346.2131.

22 MLB133-623A N-cyclohexyl-6-fluoro-2-isopropylimidazo[1,2-a]pyridin-3-amine $^1$H NMR (200 MHz, CDCl$_3$) δ 7.96-7.76 (m, 1H), 7.36 (dd, J=5.0, 9.7, 1H), 6.99-6.70 (m, 1H), 3.22-2.93 (m, 1H), 2.77 (s, 2H), 1.92-1.41 (m, 5H), 1.28 (d, J=6.9, 6H), 1.22-0.87 (m, 5H).
$^{13}$C NMR (50 MHz, CDCl$_3$) δ 155.15, 150.48, 146.47, 138.82, 138.11, 124.36, 117.28, 117.10, 114.49, 113.97, 109.17, 108.35, 57.01, 34.11, 26.20, 25.63, 24.75, 22.61.
HRMS (ESI): m/z 276.1858 (M+H)$^+$; calc. for $C_{16}H_{23}N_3F$: 276.1876.

23 MLB133-623C N-cyclohexyl-2-isopropyl-5,7-dimethylimidazo[1,2-a]pyridin-3-amine $^1$H NMR (200 MHz, CDCl$_3$) δ 7.11 (s, 1H), 6.20 (s, 1H), 3.08 (dt, J=6.9, 13.7, 1H), 2.83 (s, 3H), 2.64 (s, 1H), 2.26 (s, 3H), 1.89-1.51 (m, 5H), 1.32 (d, J=6.9, 6H), 1.26-0.97 (m, 5H).
$^{13}$C NMR (50 MHz, CDCl$_3$) δ 146.49, 143.95, 135.39, 133.92, 124.12, 115.64, 115.61, 114.12, 114.09, 59.82, 33.80, 26.27, 26.19, 25.45, 22.99, 21.03, 19.85.
HRMS (ESI): m/z 286.2277 (M+H)$^+$; calc. for $C_{18}H_{28}N_3$: 286.2283.

24 MLB133-628C 2-cyclopropyl-N-pentylimidazo[1,2-a]pyridin-3-amine $^1$H NMR (200 MHz, CDCl$_3$) δ 8.04-7.91 (m, 1H), 7.48-7.34 (m, 1H), 7.14-6.92 (m, 1H), 6.83-6.60 (m, 1H), 3.03 (t, J=7.1, 3H), 1.99 (ddd, J=5.2, 8.4, 13.5, 1H), 1.74-1.49 (m, 2H), 1.49-1.17 (m, 4H), 1.15-1.00 (m, 2H), 1.00-0.75 (m, 5H).
$^{13}$C NMR (50 MHz, CDCl$_3$) δ 141.31, 139.89, 126.43, 122.93, 121.98, 116.99, 111.18, 49.36, 30.81, 29.51, 22.83, 14.30, 8.33, 7.81.
HRMS (ESI): m/z 244.1819 (M+H)$^+$; calc. for $C_{15}H_{22}N_3$: 244.1814.

25 MLB133-624A 8-(benzyloxy)-N-cyclohexyl-2-isopropylimidazo[1,2-a]pyridin-3-amine $^1$H NMR (200 MHz, CDCl$_3$) δ 7.66 (dd, J=1.0, 6.7, 1H), 7.62-7.45 (m, 2H), 7.45-7.20 (m, 3H), 6.65-6.44 (m, 1H), 6.44-6.20 (m, 1H), 5.41 (s, 2H), 3.32-3.05 (m, 1H), 3.05-2.58 (m, 2H), 2.03-1.54 (m, 5H), 1.42 (d, J=6.9, 6H), 1.35-1.05 (m, 5H).
$^{13}$C NMR (50 MHz, CDCl$_3$) δ 147.73, 144.20, 137.20, 128.73, 127.95, 127.19, 124.30, 116.01, 110.72, 102.01, 70.82, 57.54, 34.55, 26.83, 26.13, 25.23, 23.07.
HRMS (ESI): m/z 364.2351 (M+H)$^+$; calc. for $C_{23}H_{30}N_3O$: 364.2389.

26 MLB133-627C₂-(4-methoxyphenyl)-N-(naphthalen-2-yl)imidazo[1,2-a]pyridin-3-amine ¹H NMR (200 MHz, CDCl₃) δ 7.98 (d, J=8.6, 2H), 7.87-7.57 (m, 4H), 7.57-7.10 (m, 4H), 6.99 (dd, J=2.3, 8.7, 1H), 6.86 (d, J=8.6, 2H), 6.78-6.63 (m, 2H), 5.93 (s, 1H), 3.78 (s, 3H).

¹³C NMR (50 MHz, CDCl₃) δ 159.65, 143.04, 142.80, 139.81, 138.46, 135.12, 130.15, 128.87, 128.59, 127.94, 126.87, 126.47, 126.27, 125.11, 123.31, 122.93, 117.65, 116.66, 114.29, 112.25, 107.30, 55.47.

HRMS (ESI): m/z 366.1577 (M+H)⁺; calc. for C₂₄H₂₀N₃O: 366.1606.

27 MLB133-629B N-benzyl-2-(4-methoxyphenyl)imidazo[1,2-a]pyridin-3-amine

¹H NMR (200 MHz, CDCl₃) δ 8.00-7.85 (m, 3H), 7.60-7.45 (m, 1H), 7.40-7.25 (m, 5H), 7.15-6.95 (m, 3H), 6.75-6.65 (m, 1H), 4.20 (d, 2H), 3.85 (s, 3H), 3.50-3.35 (m, 1H).

¹³C NMR (50 MHz, CDCl₃) δ 159.02, 156.38, 141.43, 139.05, 129.60, 128.58, 128.23, 128.17, 128.09, 127.53, 123.59, 122.14, 117.21, 114.04, 111.37, 55.26, 52.37.

HRMS (ESI): m/z 330.1591 (M+H)⁺; calc. for C₂₁H₂₀N₃O: 330.1606.

28 MLB133-634A N-cyclohexyl-2-((1R,5S)-6,6-dimethylbicyclo[3.1.1]hept-2-en-2-yl)imidazo[1,2-a]pyridin-3-amine ¹H NMR (200 MHz, CDCl₃) δ 8.18-7.78 (m, 1H), 7.57-7.26 (m, 1H), 7.10-6.82 (m, 1H), 6.63 (td, J=0.9, 6.7, 1H), 6.11 (ddd, J=1.3, 3.2, 4.7, 1H), 3.06 (td, J=1.3, 5.8, 1H), 3.01-2.72 (m, 2H), 2.61-2.30 (m, 3H), 2.25-2.03 (m, 1H), 1.92-1.44 (m, 5H), 1.32 (s, 3H), 1.30-1.01 (m, 6H), 0.90 (s, 3H).

¹³C NMR (50 MHz, CDCl₃) δ 141.98, 138.46, 137.13, 123.36, 122.70, 121.85, 117.41, 111.35, 57.61, 44.20, 41.16, 38.12, 34.50, 34.39, 32.50, 32.12, 26.63, 26.10, 25.21, 21.54.

HRMS (ESI): m/z 336.2413 (M+H)⁺; calc. for C₂₂H₃₀N₃: 336.2440.

29 MLB133-627B N-butyl-2-cyclopropylimidazo[1,2-a]pyridin-3-amine

¹H NMR (200 MHz, CDCl₃) δ 8.06-7.92 (m, 1H), 7.45-7.36 (m, 1H), 7.02 (ddd, J=1.3, 6.7, 9.0, 1H), 6.70 (td, J=1.1, 6.8, 1H), 3.25-2.79 (m, 3H), 1.99 (ddd, J=5.1, 8.3, 10.0, 1H), 1.73-1.31 (m, 5H), 1.15-0.73 (m, 6H).

¹³C NMR (50 MHz, CDCl₃) δ 141.04, 139.62, 126.15, 122.71, 121.72, 116.72, 110.95, 48.81, 32.95, 20.22, 13.95, 8.05, 7.56.

HRMS (ESI): m/z 230.1646 (M+H)⁺; calc. for C₁₄H₂₀N₃: 230.1657.

30 MLB133-615A 2-isopropyl-N-(4-methoxyphenyl)imidazo[1,2-a]pyridin-3-amine

¹H NMR (200 MHz, CDCl₃) δ 7.87-7.75 (m, 1H), 7.64-7.50 (m, 1H), 7.23-7.02 (m, 1H), 6.90-6.61 (m, 3H), 6.56-6.31 (m, 2H), 5.23 (s, 1H), 3.73 (s, 3H), 3.27-3.01 (m, 1H), 1.32 (d, J=6.9, 6H).

¹³C NMR (50 MHz, CDCl₃) δ 153.24, 147.91, 142.37, 139.29, 123.85, 122.40, 117.83, 117.46, 115.05, 114.08, 111.51, 55.70, 26.70, 22.33.

HRMS (ESI): m/z 282.1582 (M+H)⁺; calc. for C₁₇H₂₀N₃O: 282.1606.

31 MLB133-640B N-cyclohexyl-2-octylimidazo[1,2-a]pyridin-3-amine

¹H NMR (200 MHz, CDCl₃) δ 8.01 (d, J=6.8, 1H), 7.44 (d, J=8.4, 1H), 7.12-6.92 (m, 1H), 6.70 (t, J=6.7, 1H), 2.98-2.77 (m, 2H), 2.77-2.58 (m, 2H), 1.95-1.48 (m, 7H), 1.48-1.00 (m, 15H), 0.98-0.72 (m, 3H).

¹³C NMR (50 MHz, CDCl₃) δ 141.35, 139.73, 124.40, 122.69, 122.37, 116.85, 110.89, 57.21, 34.33, 31.91, 29.85, 29.67, 29.50, 29.29, 27.51, 25.86, 24.93, 22.68, 14.09.

HRMS (ESI): m/z 328.2747 (M+H)⁺; calc. for C₂₁H₃₄N₃: 328.2753.

32 DG120-036 N-butyl-N-ethyl-2-isopropylimidazo[1,2-a]pyridin-3-amine

¹H NMR (200 MHz, CDCl₃) δ 7.99 (d, J=6.8, 1H), 7.49 (d, J=9.0, 1H), 7.12-6.98 (m, 1H), 6.72 (t, J=6.3, 1H), 3.16 (dt, J=7.0, 13.8, 1H), 2.99 (dd, J=6.3, 12.5, 3H), 2.88-2.70 (m, 1H), 1.74-1.40 (m, 5H), 1.38 (d, J=6.9, 7H), 0.95 (t, J=7.0, 4H).

33 MLB133-608B N-cyclohexyl-2-(4-(dimethylamino)phenyl)imidazo[1,2-a]pyridin-3-amine ¹H NMR (200 MHz, CDCl₃) δ 8.14-8.04 (m, 1H), 7.94 (d, J=8.7, 2H), 7.54-7.47 (m, 1H), 7.07 (ddd, J=1.3, 6.6, 8.9, 1H), 6.81 (d, J=8.9, 1H), 6.73 (td, J=0.9, 6.9, 2H), 3.01 (s, 8H), 1.93-1.43 (m, 5H), 1.43-0.93 (m, 5H).

¹³C NMR (50 MHz, CDCl₃) δ 149.65, 141.40, 137.26, 131.84, 127.83, 123.07, 122.78, 122.41, 116.87, 112.33, 110.95, 56.80, 40.42, 34.15, 25.79, 24.83.

34 MLB133-629A 2-(4-methoxyphenyl)-N-(2,4,4-trimethylpentan-2-yl)imidazo[1,2-a]pyridin-3-amine ¹H NMR (200 MHz, CDCl₃) δ 8.21 (d, J=6.9, 1H), 7.79 (d, J=8.9, 2H), 7.51 (d, J=9.0, 1H), 7.10 (dd, J=7.2, 8.5, 1H), 6.97 (d, J=8.9, 2H), 6.75 (t, J=6.8, 1H), 3.85 (s, 3H), 3.34-2.95 (m, 1H), 1.60 (s, 2H), 1.04 (s, 9H), 0.96 (s, 6H).

¹³C NMR (50 MHz, CDCl₃) δ 159.21, 142.18, 140.03, 129.78, 128.35, 123.91, 123.70, 123.01, 117.39, 113.94, 111.32, 60.88, 57.35, 55.53, 32.15, 32.02, 29.26.

HRMS (ESI): m/z 352.2379 (M+H)⁺; calc. for C₂₂H₃₀N₃O: 352.2389.

35 MLB133-634B (5-(3-(cyclohexylamino)imidazo[1,2-a]pyridin-2-yl)furan-2-yl)methanol ¹H NMR (400 MHz, CDCl₃) δ 8.07-8.02 (m, 1H), 7.49-7.45 (m, 1H), 7.14-7.08 (m, 1H), 6.80-6.71 (m, 2H), 6.33 (d, 1H), 4.66 (s, 2H), 3.49 (br s, 1H), 2.95-2.90 (m, 2H), 1.87-1.82 (m, 2H), 1.75-1.68 (m, 2H), 1.60-1.55 (m, 1H), 1.35-1.10 (m, 5H).

¹³C NMR (101 MHz, DMSO-d₆) δ 154.38, 148.63, 140.53, 127.56, 125.49, 123.72, 123.10, 116.47, 111.52, 108.47, 106.98, 56.25, 55.81, 33.54, 25.36, 24.48.

HRMS (ESI): m/z 312.1679 (M+H)⁺; calc. for C₁₈H₂₂N₃O₂: 312.1712.

36 MLB133-636A 6-chloro-N-cyclohexyl-2-cyclopropylimidazo[1,2-a]pyridin-3-amine ¹H NMR (200 MHz, CDCl₃) δ 8.10-7.93 (m, 1H), 7.41-7.27 (m, 1H), 7.08-6.89 (m, 1H), 3.19-2.57 (m, 2H), 2.07-

1.84 (m, 3H), 1.84-1.68 (m, 2H), 1.68-1.45 (m, 1H), 1.44-1.11 (m, 5H), 1.11-0.80 (m, 4H).

$^{13}$C NMR (50 MHz, CDCl$_3$) δ 141.94, 139.49, 125.32, 123.91, 119.89, 119.36, 116.94, 57.21, 34.34, 25.79, 24.91, 8.20, 7.93.

HRMS (ESI): m/z 290.1408 (M+H)$^+$; calc. for C$_{16}$H$_{21}$N$_3$Cl: 290.1424.

37 MR762-137.4 2-(3,4-dimethoxyphenyl)-N-(2-morpholinoethyl)imidazo[1,2-a]pyridin-3-amine $^1$H NMR (200 MHz, CDCl$_3$) δ 8.16 (d, J=7, 1H), 8.10 (m, 2H), 7.60 (m, 2H), 7.14-7.32 (m, 1H), 6.93 (br t, 1H), 4.14 (br s, 1H), 3.98 (s, 3H), 3.92 (s, 3H), 3.76 (t, 4H), 3.07-3.10 (m, 2H), 2.52-2.58 (m, 2H), 2.44 (t, 4H).

$^{13}$C NMR (50 MHz, CDCl$_3$) δ 149.6, 148.9, 138.7, 126.2, 126.0, 124.1, 122.5, 119.4, 117.3, 112.0, 111.4, 111.3, 110.0, 67.0, 58.7, 56.4, 56.2, 54.0, 44.3.

38 MLB133-649A N-cyclohexyl-2-(pentan-2-yl)imidazo[1,2-a]pyridin-3-amine $^1$H NMR (200 MHz, CDCl$_3$) δ 7.93 (dt, J=1.0, 6.8, 1H), 7.39 (dt, J=0.9, 9.0, 1H), 6.93 (ddd, J=1.3, 6.7, 9.0, 1H), 6.59 (td, J=1.1, 6.7, 1H), 3.05-2.60 (m, 2H), 1.91-1.38 (m, 6H), 1.26 (d, J=6.9, 3H), 1.22-0.93 (m, 7H), 0.80 (t, J=7.2, 3H).

$^{13}$C NMR (50 MHz, CDCl$_3$) δ 143.69, 141.28, 123.68, 122.40, 122.21, 116.71, 110.57, 57.10, 39.10, 34.09, 31.11, 25.63, 24.75, 24.68, 20.86, 13.99.

HRMS (ESI): m/z 286.2251 (M+H)$^+$; calc. for C$_{18}$H$_{28}$N$_3$: 286.2283.

39 MLB133-648B N-cyclohexyl-2-(2,4-dimethoxyphenyl)imidazo[1,2-a]pyridin-3-amine $^1$H NMR (200 MHz, CDCl$_3$) δ 8.09 (dt, J=1.0, 6.7, 1H), 7.76 (d, J=8.5, 1H), 7.53 (d, J=9.0, 1H), 7.08 (ddd, J=1.3, 6.7, 9.1, 1H), 6.75 (td, J=1.1, 6.8, 1H), 6.67 (dd, J=2.4, 8.5, 1H), 6.58 (d, J=2.2, 1H), 3.87 (s, 6H), 3.70 (s, 3H), 2.87-2.40 (m, 1H), 2.01-1.27 (m, 4H), 1.27-0.75 (m, 4H).

$^{13}$C NMR (50 MHz, CDCl$_3$) δ 160.67, 156.86, 132.32, 126.71, 123.30, 122.56, 116.96, 111.38, 105.81, 99.31, 67.09, 56.42, 56.12, 55.44, 34.15, 25.74, 24.83.

HRMS (ESI): m/z 352.2012 (M+H)$^+$; calc. for C$_{21}$H$_{26}$N$_3$O$_2$: 352.2025.

40 MLB133-653B N-cyclohexyl-2-neopentylimidazo[1,2-a]pyridin-3-amine $^1$H NMR (200 MHz, CDCl$_3$) δ 8.01 (dt, J=1.0, 6.6, 1H), 7.46 (dt, J=1.0, 9.3, 1H), 7.03 (ddd, J=1.3, 6.6, 9.0, 1H), 6.70 (td, J=1.1, 6.8, 1H), 3.11-2.75 (m, 2H), 2.64 (s, 2H), 2.07-1.43 (m, 5H), 1.41-1.07 (m, 5H), 1.00 (s, 9H).

$^{13}$C NMR (50 MHz, CDCl$_3$) δ 140.88, 137.31, 126.04, 122.44, 122.39, 116.98, 110.75, 56.84, 41.34, 34.50, 33.12, 29.85, 25.83, 24.96.

HRMS (ESI): m/z 286.2247 (M+H)$^+$; calc. for C$_{18}$H$_{28}$N$_3$: 286.2283.

41 MLB133-655A N-cyclohexyl-2-pentylimidazo[1,2-a]pyridin-3-amine $^1$H NMR (200 MHz, CDCl$_3$) δ 8.06-7.96 (m, 1H), 7.51-7.35 (m, 1H), 7.04 (ddd, J=1.3, 6.7, 9.0, 1H), 6.71 (td, J=1.1, 6.8, 1H), 3.14-2.77 (m, 2H), 2.77-2.50 (m, 2H), 1.98-1.47 (m, 7H), 1.47-1.29 (m, 4H), 1.27-1.05 (m, 5H), 0.90 (t, J=6.9, 3H).

$^{13}$C NMR (50 MHz, CDCl$_3$) δ 141.32, 139.65, 124.40, 122.74, 122.36, 116.81, 110.92, 57.20, 34.32, 32.05, 29.35, 27.43, 25.84, 24.92, 22.57, 14.07.

HRMS (ESI): m/z 286.2270 (M+H)$^+$; calc. for C$_{18}$H$_{28}$N$_3$: 286.2283.

42 DG 402-49706 5-bromo-2-(2-chlorophenyl)-N-cyclohexylimidazo[1,2-a]pyridin-3-amine $^1$H NMR (400 MHz, CDCl$_3$) δ 7.60 (d, J=2.9, 1H), 7.60-7.57 (m, 1H), 7.54 (d, J=1.8, 1H), 7.52 (d, J=1.8, 1H), 7.50-7.48 (m, 1H), 7.47 (d, J=2.5, 1H), 7.37-7.29 (m, 4H), 7.03-6.96 (m, 3H), 6.94 (t, J=4.1, 1H), 3.28 (d, J=6.2, 2H), 2.97-2.62 (m, 2H), 1.66 (d, J=12.4, 5H), 1.59-1.48 (m, 4H), 1.48-1.35 (m, 2H), 1.16-0.97 (m, 7H), 0.97-0.75 (m, 4H).

$^{13}$C NMR (101 MHz, CDCl$_3$) δ 143.74, 138.16, 133.87, 133.32, 132.60, 129.50, 129.21, 128.45, 126.64, 123.78, 118.62, 117.34, 112.21, 58.29, 32.70, 25.73, 24.50.

HRMS (ESI): m/z 404.0516 (M+H)$^+$; calc. for C$_{19}$H$_{20}$N$_3$ClBr: 404.0529.

43 DG 402-49651 2-(2-bromophenyl)-N-cyclohexylimidazo[1,2-a]pyridin-3-amine $^1$H NMR (200 MHz, CDCl$_3$) δ 8.43-7.97 (m, 3H), 7.64 (td, J=1.5, 7.7, 4H), 7.58-7.48 (m, 2H), 7.39 (td, J=1.3, 7.5, 2H), 7.31-7.21 (m, 2H), 7.21-7.13 (m, 2H), 7.11 (dd, J=1.3, 6.7, 1H), 6.80 (td, J=1.1, 6.7, 2H), 3.42-3.09 (m, 2H), 2.82-2.48 (m, 2H), 1.80-1.33 (m, 12H), 1.21-0.81 (m, 13H).

$^{13}$C NMR (50 MHz, CDCl$_3$) δ 141.35, 136.12, 132.67, 132.50, 129.26, 127.26, 125.80, 123.51, 122.87, 122.79, 117.53, 111.46, 56.34, 33.80, 25.64, 24.51.

HRMS (ESI): m/z 370.0892 (M+H)$^+$; calc. for C$_{19}$H$_{21}$N$_3$Br: 370.0919.

44 DG 402-49659 2-(2-chlorophenyl)-N-pentylimidazo[1,2-a]pyridin-3-amine $^1$H NMR (400 MHz, CDCl$_3$) δ 8.12 (dt, J=1.2, 6.9, 1H), 7.79-7.61 (m, 1H), 7.55 (dt, J=1.1, 9.1, 1H), 7.51-7.44 (m, 1H), 7.42-7.28 (m, 2H), 7.14 (ddd, J=1.3, 6.7, 9.1, 1H), 6.82 (td, J=1.1, 6.8, 1H), 3.30 (t, J=6.2, 1H), 2.83 (q, J=6.7, 2H), 1.95-1.64 (m, 1H), 1.42-1.24 (m, 2H), 1.24-1.05 (m, 3H), 0.90-0.60 (m, 3H).

$^{13}$C NMR (101 MHz, CDCl$_3$) δ 141.47, 133.93, 132.84, 132.60, 129.48, 129.14, 126.87, 123.57, 122.60, 117.69, 111.62, 48.27, 30.02, 28.93, 22.38, 13.90.

HRMS (ESI): m/z 314.1414 (M+H)$^+$; calc. for C$_{18}$H$_{21}$N$_3$Cl: 314.1424.

45 DG789-110 N-butyl-2-(4-methoxyphenyl)imidazo[1,2-a]pyridin-3-amine $^1$H NMR (400 MHz, CDCl$_3$) δ 8.08 (dt, J=1.2, 6.8, 1H), 7.97-7.89 (m, 2H), 7.61-7.55 (m, 1H), 7.15 (ddd, J=1.3, 6.7, 9.0, 1H), 6.99-6.94 (m, 2H), 6.82 (td, J=1.1, 6.8, 1H), 3.85 (s, 4H), 3.02 (t, J=7.1, 2H), 1.58 (dt, J=6.9, 14.4, 2H), 1.41 (dq, J=7.2, 14.3, 2H), 0.92 (t, J=7.3, 3H).

$^{13}$C NMR (101 MHz, CDCl$_3$) δ 159.10, 140.57, 134.37, 128.20, 125.71, 125.54, 124.57, 122.43, 116.53, 114.03, 112.06, 55.22, 47.92, 32.78, 20.18, 13.89.

HRMS (ESI): m/z 296.1735 (M+H)$^+$; calc. for C$_{18}$H$_{22}$N$_3$O: 296.1763.

46 DG789-112 2-(4-methoxyphenyl)-N-pentylimidazo[1,2-a]pyridin-3-amine $^1$H NMR (400 MHz, CDCl$_3$) δ 8.06 (dt, J=1.1, 6.8, 1H), 7.95-7.89 (m, 2H), 7.56 (d, J=9.0, 1H), 7.13 (ddd, J=1.3, 6.7, 9.0, 1H), 7.01-6.94 (m, 2H), 6.80 (td, J=1.1, 6.8, 1H), 3.85 (s, 4H), 3.01 (t, J=7.1, 2H), 1.58 (dd, J=7.6, 14.8, 2H), 1.34 (ddd, J=5.1, 9.9, 19.4, 4H), 0.89 (t, J=7.1, 3H).

$^{13}$C NMR (101 MHz, CDCl$_3$) δ 159.04, 140.79, 134.74, 128.20, 126.10, 125.52, 124.24, 122.35, 116.72, 114.01, 111.85, 55.22, 48.20, 30.36, 29.17, 22.47, 13.97.

HRMS (ESI): m/z 310.1906 (M+H)$^+$; calc. for C$_{19}$H$_{24}$N$_3$O: 310.1919.

47 DG789-116 N-cyclopropyl-2-(4-methoxyphenyl)imidazo[1,2-a]pyridin-3-amine

48 DG 402-49760 5-chloro-2-(2-chlorophenyl)-N-cyclopentylimidazo[1,2-a]pyridin-3-amine $^1$H NMR (400 MHz, CDCl$_3$) δ 7.63-7.58 (m, 1H), 7.52-7.46 (m, 2H), 7.38-7.30 (m, 2H), 7.04 (dd, J=7.2, 9.0, 1H), 6.78 (dd, J=1.1, 7.2, 1H), 3.57-3.40 (m, 1H), 3.27 (d, J=5.7, 1H), 1.70-1.46 (m, 2H), 1.46-1.30 (m, 4H), 1.30-1.14 (m, 2H).

$^{13}$C NMR (101 MHz, CDCl$_3$) δ 143.66, 137.58, 133.63, 133.36, 132.65, 129.50, 129.27, 126.64, 126.37, 126.13, 123.65, 116.80, 114.02, 61.91, 32.48, 22.98.

HRMS (ESI): m/z 346.0865 (M+H)$^+$; calc. for C$_{18}$H$_{18}$N$_3$Cl$_2$: 346.0878.

49 MLB133-635A N-butyl-6-chloro-2-(5-methyl-isoxazol-3-yl)imidazo[1,2-a]pyridin-3-amine $^1$H NMR (200 MHz, CDCl$_3$) δ 8.08-7.95 (m, 1H), 7.46 (d, J=9.6, 1H), 7.06 (dd, J=2.0, 9.6, 1H), 6.56 (s, 1H), 4.54 (t, J=6.8, 1H), 3.07 (dd, J=6.9, 13.8, 2H), 2.48 (s, 3H), 1.73-1.50 (m, 2H), 1.50-1.22 (m, 2H), 0.92 (t, J=7.2, 3H).

$^{13}$C NMR (50 MHz, CDCl$_3$) δ 168.93, 159.22, 139.76, 131.08, 124.93, 124.54, 120.57, 120.51, 118.33, 100.50, 47.42, 32.64, 20.13, 13.85, 12.21.

HRMS (ESI): m/z 305.1180 (M+H)$^+$; calc. for C$_{15}$H$_{18}$N$_4$ClO: 305.1169.

50 MLB133-634C N-benzyl-6-chloro-2-(5-methyl-isoxazol-3-yl)imidazo[1,2-a]pyridin-3-amine $^1$H NMR (200 MHz, CDCl$_3$) δ 7.98 (dd, J=0.9, 1.9, 1H), 7.48 (dd, J=0.8, 9.6, 1H), 7.44-7.22 (m, 5H), 7.08 (dd, J=2.0, 9.6, 1H), 6.61-6.54 (m, 1H), 4.80 (t, J=6.4, 1H), 4.25 (d, J=6.5, 2H), 2.49 (d, J=11.7, 3H).

$^{13}$C NMR (50 MHz, CDCl$_3$) δ 169.36, 159.09, 140.09, 138.64, 130.45, 128.80, 128.50, 127.88, 125.78, 121.07, 120.93, 118.35, 100.84, 52.22, 12.49.

HRMS (ESI): m/z 339.0979 (M+H)$^+$; calc. for C$_{18}$H$_{16}$N$_4$OCl: 339.1013.

51 MLB133-635B N-butyl-5,7-dimethyl-2-(5-methylisoxazol-3-yl)imidazo[1,2-a]pyridin-3-amine $^1$H NMR (200 MHz, CDCl$_3$) δ 7.09 (s, 1H), 6.56 (d, J=0.6, 1H), 6.25 (s, 1H), 3.98 (t, J=7.2, 1H), 3.09-2.73 (m, 5H), 2.45 (s, 3H), 2.26 (s, 3H), 1.76-1.50 (m, 2H), 1.38 (dq, J=7.1, 13.8, 2H), 0.90 (t, J=7.2, 3H).

$^{13}$C NMR (50 MHz, CDCl$_3$) δ 168.42, 159.50, 143.95, 135.77, 134.93, 132.46, 126.01, 116.10, 114.03, 100.75, 52.08, 31.99, 20.86, 20.19, 18.57, 13.93, 12.10.

HRMS (ESI): m/z 299.1869 (M+H)$^+$; calc. for C$_{17}$H$_{23}$N$_4$O: 299.1872.

52 MLB133-636B N-benzyl-2-cyclopropylimidazo[1,2-a]pyridin-3-amine $^1$H NMR (200 MHz, CDCl$_3$) δ 7.96 (d, J=6.8, 1H), 7.55-7.18 (m, 6H), 7.12-6.97 (m, 1H), 6.77-6.54 (m, 1H), 4.21 (s, 2H), 3.52-2.83 (m, 1H), 1.85 (ddd, J=5.1, 8.3, 9.9, 1H), 1.11-0.97 (m, 2H), 0.91 (dtd, J=2.1, 4.9, 7.3, 2H).

$^{13}$C NMR (50 MHz, CDCl$_3$) δ 139.53, 128.72, 128.55, 128.28, 127.88, 127.46, 122.92, 121.68, 116.70, 111.00, 107.42, 53.26, 8.00, 7.57.

HRMS (ESI): m/z 264.1477 (M+H)$^+$; calc. for C$_{17}$H$_{18}$N$_3$: 264.1501.

53 MR762-137.15 N-cyclohexyl-2-(furan-2-yl)imidazo[1,2-a]pyridin-3-amine $^1$H NMR (200 MHz, CDCl$_3$) δ 8.07 (dd, J=6.7, 1.2, 1H), 7.53 (d, J=9.0, 1H), 7.51 (d, J=1.6, 1H), 7.15 (ddd, J=9.0, 6.7, 1.2, 1H), 6.91 (d, J=3.3, 1H), 6.79 (td, J=6.7, 1.0, 1H), 6.55 (dd, J=3.3, 1.6, 1H), 3.62 (br s, 1H) 2.85-3.10 (m, 1H), 1.50-2.00, 1.05-1.45 (m, 9H).

$^{13}$C NMR (50 MHz, CDCl$_3$) δ 149.72, 141.56, 141.37, 127.40, 125.45, 124.45, 122.81, 116.90, 111.91, 111.52, 106.98, 57.12, 34.13, 25.76, 25.01.

54 10061 N-cyclohexyl-2-(4-methoxyphenyl)imidazo[1,2-a]pyridin-3-amine $^1$H NMR (200 MHz, CDCl$_3$) δ 8.11 (d, J=6.8, 2H), 8.02 (d, J=8.6, 2H), 7.16-7.08 (m, 1H), 7.02-6.98 (d, J=8.6, 2H), 6.80-6.73 (m, 1H), 3.87 (s, 3H), 1.80-1.59 (br m, 10H).

$^{13}$C NMR (50 MHz, CDCl$_3$) δ 158.3, 141.6, 138.3, 137.1, 128.6, 127.3, 124.3, 123.9, 118.5, 117.3, 116.2, 57.1, 55.5, 34.4, 26.0, 25.1.

55 MR762-137.8 2-(furan-2-yl)-N-(2-morpholinoethyl)imidazo[1,2-a]pyridin-3-amine $^1$H NMR (200 MHz, CDCl$_3$) δ 8.07 (dd, J=6.4, 1.2, 1H), 7.51 (d, J=8.0, 1H), 7.45 (d, J=0.8, 1H), 7.11 (ddd, J=8.0, 6.4, 1.2, 1H), 6.89 (d, J=3.2, 1H), 6.78 (td, J=6.4, 0.8, 1H), 6.53 (dd, J=3.2, 1.2, 1H), 4.34 (br s, 1H), 3.76 (m 4H), 3.13 (t, J=6.0, 2H), 2.61 (t, J=6.4, 2H), 2.50 (br s, 4H).

$^{13}$C NMR (50 MHz, CDCl$_3$) δ 150.3, 141.7, 141.3, 126.9, 126.7, 123.9, 122.4, 117.3, 111.6, 111.5, 106.3, 67.0, 58.2, 53.5, 44.3.

56 MR762-137.11 N-cyclohexyl-2-(3,4-dimethoxyphenyl)imidazo[1,2-a]pyridin-3-amine $^1$H NMR (200 MHz, CDCl$_3$) δ 8.01 (d, J=6.8, 1H), 7.71 (d, J=1.8, 1H), 7.60-7.48 (m, 2H), 7.12-6.94 (m, 1H), 6.90, (d, J=8.4, 1H), 3.97 (s, 3H), 3.91 (s, 3H), 3.20-2.81 (m, 2H), 1.83-1.21 (br m, 10H).

$^{13}$C NMR (50 MHz, CDCl$_3$) 149.3, 148.7, 141.6, 136.7, 127.6, 124.4, 123.9, 122.8, 119.7, 117.3, 111.7, 111.4, 110.9, 67.3, 57.0, 56.2, 56.1, 34.5, 26.0, 25.1.

57 MLB133-639A 4-(3-(cyclohexylamino)imidazo[1,2-a]pyridin-2-yl)-2,6-dimethoxyphenol $^1$H NMR (200 MHz, DMSO-d$_6$) δ 8.49-8.22 (m, 2H), 7.45 (d, J=8.8, 1H), 7.21-7.06 (m, 1H), 6.86 (t, J=6.7, 1H), 4.87-4.59 (m, 1H), 3.85 (s, 6H), 3.07-2.81 (m, 1H), 1.86-1.43 (m, 5H), 1.43-0.92 (m, 5H).

$^{13}$C NMR (50 MHz, DMSO-d$_6$) δ 147.76, 140.11, 135.09, 134.79, 124.95, 124.41, 123.44, 123.03, 116.24, 110.93, 104.05, 56.18, 55.86, 33.58, 25.44, 24.40.

HRMS (ESI): m/z 368.1946 (M+H)$^+$; calc. for C$_{21}$H$_{26}$N$_3$O$_3$: 368.1974.

58 MLB133-639C 2-(4-(benzyloxy)benzyl)-N-cyclohexylimidazo[1,2-a]pyridin-3-amine $^1$H NMR (200 MHz, CDCl$_3$) δ 8.10 (d, J=6.8, 1H), 8.01 (d, J=8.8, 2H), 7.59-7.27 (m, 7H), 7.13-7.00 (m, 2H), 6.76 (t, J=6.8, 1H), 5.13 (s, 2H), 2.98 (m, 1H), 1.75 (m, 5H), 1.47-0.97 (m, 5H).

$^{13}$C NMR (50 MHz, CDCl$_3$) δ 158.10, 141.42, 136.97, 136.56, 129.52, 128.45, 128.28, 127.83, 127.43, 124.05, 123.51, 122.52, 117.07, 114.82, 111.27, 69.99, 56.77, 34.13, 25.73, 24.79.

HRMS (ESI): m/z 412.2364 (M+H)$^+$; calc. for C$_{27}$H$_{30}$N$_3$O: 412.2389.

59 MLB133-639B 2-(3-(cyclohexylamino)imidazo[1,2-a]pyridin-2-yl)phenol $^1$H NMR (200 MHz, DMSO-d$_6$+CD$_3$OD) δ 8.36 (d, J=6.8, 1H), 8.17 (dd, J=1.7, 8.1, 1H), 7.54 (d, J=6.8, 1H), 7.40-7.15 (m, 2H), 7.10-6.85 (m, 3H), 3.05-2.81 (m, 1H), 1.99-1.44 (m, 5H), 1.44-1.01 (m, 5H).

$^{13}$C NMR (50 MHz, DMSO-d$_6$+CD$_3$OD) δ 156.77, 141.58, 135.94, 129.75, 129.14, 125.78, 125.08, 123.89, 119.89, 117.86, 116.87, 113.01, 57.65, 34.24, 26.43, 25.54.

HRMS (ESI): m/z 308.1767 (M+H)$^+$; calc. for C$_{19}$H$_{22}$N$_3$O: 308.1763.

60 MLB133-649C N-cyclohexyl-2-(pentan-3-yl)imidazo[1,2-a]pyridin-3-amine $^1$H NMR (200 MHz, CDCl$_3$) δ 8.05 (dt, J=1.0, 6.8, 1H), 7.58-7.38 (m, 1H), 7.03 (ddd, J=1.3, 6.6, 9.0, 1H), 6.70 (td, J=1.1, 6.7, 1H), 3.20-2.72 (m, 1H), 2.72-2.42 (m, 1H), 1.99-1.44 (m, 9H), 1.41-1.01 (m, 6H), 0.80 (t, J=7.4, 6H).

$^{13}$C NMR (50 MHz, CDCl$_3$) δ 142.04, 141.60, 125.60, 122.61, 122.45, 116.96, 110.69, 57.56, 40.98, 34.25, 28.31, 25.86, 24.92, 12.62.

HRMS (ESI): m/z 286.2281 (M+H)$^+$; calc. for C$_{18}$H$_{28}$N$_3$: 286.2283.

61 MLB133-648A N-cyclohexyl-2-(4-nitrophenyl)imidazo[1,2-a]pyridin-3-amine $^1$H NMR (200 MHz, CDCl$_3$) δ 8.49-8.21 (m, 4H), 8.07 (dt, J=1.0, 6.9, 1H), 7.55 (d, J=8.3, 1H), 7.18 (ddd, J=1.3, 6.7, 9.1, 1H), 6.83 (td, J=1.0, 6.8, 1H), 3.28-2.79 (m, 2H), 2.04-1.47 (m, 5H), 1.47-0.97 (m, 5H).

$^{13}$C NMR (50 MHz, CDCl$_3$) δ 146.55, 142.06, 141.13, 134.43, 127.26, 126.47, 124.83, 123.80, 122.65, 117.89, 112.23, 57.12, 34.36, 25.66, 24.87.

HRMS (ESI): m/z 337.1670 (M+H)$^+$; calc. for C$_{19}$H$_{21}$N$_4$O$_2$: 337.1665.

62 MLB133-648C N-cyclohexyl-2-isobutylimidazo[1,2-a]pyridin-3-amine $^1$H NMR (200 MHz, CDCl$_3$) δ 8.08-7.95 (m, 1H), 7.50-7.36 (m, 1H), 7.03 (ddd, J=1.2, 6.7, 9.0, 1H), 6.70 (td, J=0.9, 6.7, 1H), 3.00-2.69 (m, 2H), 2.58 (d, J=7.1, 2H), 2.20 (dt, J=6.8, 13.4, 1H), 2.04-1.49 (m, 5H), 1.38-1.07 (m, 5H), 0.95 (d, J=6.6, 6H).

$^{13}$C NMR (50 MHz, CDCl$_3$) δ 141.29, 138.72, 125.17, 122.65, 122.38, 116.83, 110.81, 57.21, 36.67, 34.34, 28.88, 25.83, 24.92, 22.74.

HRMS (ESI): m/z 272.2105 (M+H)$^+$; calc. for C$_{17}$H$_{26}$N$_3$: 272.2127.

63 MLB133-649B 4-(3-(cyclohexylamino)imidazo[1,2-a]pyridin-2-yl)phenol $^1$H NMR (200 MHz, DMSO-d$_6$) δ 9.41 (s, 1H), 8.26 (d, J=6.9, 1H), 8.03 (d, J=8.6, 2H), 7.41 (d, J=8.9, 1H), 7.28-7.01 (m, 1H), 6.83 (t, J=7.3, 3H), 4.60 (d, J=5.5, 1H), 3.45-3.38 (m, 1H), 3.00-2.65 (m, 1H), 2.01-1.40 (m, 5H), 1.40-0.85 (m, 5H).

$^{13}$C NMR (50 MHz, DMSO-d$_6$) δ 154.73, 138.53, 133.82, 126.11, 123.79, 122.44, 121.29, 121.20, 114.42, 113.20, 109.01, 54.45, 31.83, 23.77, 22.78.

HRMS (ESI): m/z 308.1754 (M+H)$^+$; calc. for C$_{19}$H$_{22}$N$_3$O: 308.1763.

64 MLB133-650A 2-tert-butyl-N-cyclohexylimidazo[1,2-a]pyridin-3-amine $^1$H NMR (200 MHz, CDCl$_3$) δ 8.08 (dt, J=1.0, 6.9, 1H), 7.47 (d, J=9.0, 1H), 7.04 (ddd, J=1.3, 6.6, 8.9, 1H), 6.69 (td, J=0.9, 6.7, 1H), 3.17-2.71 (m, 2H), 2.06-1.51 (m, 6H), 1.47 (s, 9H), 1.40-1.02 (m, 5H).

$^{13}$C NMR (50 MHz, CDCl$_3$) δ 140.10, 138.20, 123.62, 122.89, 116.56, 111.17, 109.72, 58.68, 34.13, 33.19, 30.66, 25.82, 25.05.

HRMS (ESI): m/z 272.2102 (M+H)$^+$; calc. for C$_{17}$H$_{26}$N$_3$: 272.2127.

65 MLB133-650B N-(4-(3,4-dichlorophenoxy)butyl)-2-(furan-2-yl)imidazo[1,2-a]pyridin-3-amine $^1$H NMR (200 MHz, CDCl$_3$) δ 7.88 (d, J=6.9, 1H), 7.50-7.25 (m, 2H), 7.15 (d, J=8.9, 1H), 6.98 (ddd, J=1.0, 6.7, 8.2, 1H), 6.83 (d, J=2.9, 1H), 6.79-6.72 (m, 1H), 6.70-6.50 (m, 2H), 6.47-6.24 (m, 2H), 3.79 (dd, J=7.6, 13.5, 2H), 3.59 (d, J=6.1, 1H), 2.98 (dd, J=6.4, 12.9, 2H), 1.88-1.31 (m, 4H).

$^{13}$C NMR (50 MHz, CDCl$_3$) δ 157.76, 150.15, 141.52, 141.32, 132.52, 130.38, 129.19, 127.45, 126.16, 123.57, 122.13, 117.09, 116.14, 115.54, 114.26, 111.51, 106.26, 68.07, 48.10, 26.99, 26.46.

HRMS (ESI): m/z 416.0902 (M+H)$^+$; calc. for C$_{21}$H$_{20}$N$_3$O$_2$Cl$_2$: 416.0933.

66 MLB133-650C N-(4-(3,4-dichlorophenoxy)butyl)-2-isopropylimidazo[1,2-a]pyridin-3-amine $^1$H NMR (200 MHz, CDCl$_3$) δ 7.88 (dt, J=1.0, 6.8, 1H), 7.37 (br dt, J=9.0, 1H), 7.16 (d, J=8.9, 1H), 6.95 (dd, J=1.2, 6.7, 1H), 6.90 (dd, J=1.3, 6.8, 1H), 6.85 (d, J=2.9, 1H), 6.71-6.49 (m, 1H), 3.82 (t, J=6.0, 2H), 3.20-2.99 (m, 1H), 2.92 (d, J=6.1, 3H), 1.89-1.44 (m, 4H), 1.27 (d, J=6.9, 6H).

$^{13}$C NMR (50 MHz, CDCl$_3$) δ 157.76, 144.16, 141.06, 132.51, 129.16, 128.99, 123.96, 122.57, 121.87, 120.40, 116.86, 115.52, 114.26, 110.86, 68.08, 48.68, 27.25, 26.51, 26.25, 22.64.

HRMS (ESI): m/z 392.1259 (M+H)$^+$; calc. for C$_{20}$H$_{24}$N$_3$OCl$_2$: 392.1296.

67 MLB133-650D N-(4-chlorobenzyl)-2-isopropylimidazo[1,2-a]pyridin-3-amine $^1$H NMR (200 MHz, CDCl$_3$) δ 7.96 (d, J=6.8, 2H), 7.52 (d, J=9.0, 2H), 7.18-6.99 (m, 2H), 6.73 (t, J=6.7, 2H), 4.03 (s, 2H), 3.39-3.07 (m, 1H), 3.07-2.81 (m, 1H), 1.23 (d, J=6.9, 6H).

$^{13}$C NMR (101 MHz, CDCl$_3$) δ 144.68, 141.38, 137.86, 133.42, 129.58, 128.75, 123.52, 123.24, 122.00, 117.17, 111.34, 52.60, 26.43, 22.69.

HRMS (ESI): m/z 300.1241 (M+H)$^+$; calc. for C$_{17}$H$_{19}$N$_3$Cl: 300.1268.

68 MLB133-653A 2-(5-chlorofuran-2-yl)-N-cyclohexylimidazo[1,2-a]pyridin-3-amine $^1$H NMR (200 MHz, CDCl$_3$) δ 7.98 (dt, J=1.1, 6.8, 1H), 7.47-7.34 (m, 1H), 7.04 (ddd, J=1.3, 6.7, 9.1, 1H), 6.76 (d, J=3.4, 1H), 6.69 (td, J=1.0, 6.8, 1H), 6.21 (d, J=3.4, 1H), 3.42 (d, J=6.6, 1H), 3.07-2.73 (m, 1H), 2.01-1.41 (m, 5H), 1.41-0.99 (m, 5H).
$^{13}$C NMR (50 MHz, CDCl$_3$) δ 149.97, 141.83, 135.16, 127.34, 125.70, 124.15, 122.79, 117.22, 111.66, 108.25, 108.04, 57.38, 34.18, 25.76, 24.95.
HRMS (ESI): m/z 316.1195 (M+H)$^+$; calc. for C$_{17}$H$_{19}$N$_3$OCl: 316.1217.

69 MLB133-653C N-cyclohexyl-2-(5-ethylthiophen-2-yl)imidazo[1,2-a]pyridin-3-amine $^1$H NMR (200 MHz, CDCl3) δ 8.07 (dt, J=1.1, 6.9, 1H), 7.50 (d, J=9.0, 1H), 7.41 (d, J=3.6, 1H), 7.10 (ddd, J=1.3, 6.6, 9.0, 1H), 6.92-6.79 (m, 1H), 6.79-6.66 (m, 1H), 3.27-2.97 (m, 2H), 2.90 (dd, J=7.6, 15.1, 2H), 2.09-1.51 (m, 5H), 1.36 (t, J=7.5, 4H), 1.30-1.00 (m, 4H).
$^{13}$C NMR (50 MHz, CDCl$_3$) δ 147.81, 140.51, 125.43, 125.06, 124.05, 123.45, 122.97, 116.09, 112.42, 57.03, 34.26, 25.74, 24.92, 23.51, 15.86.
HRMS (ESI): m/z 326.1695 (M+H)$^+$; calc. for C$_{19}$H$_{24}$N$_3$S: 326.1691.

70 MLB133-654C 4-(3-(cyclohexylamino)imidazo[1,2-a]pyridin-2-yl)-2-methoxyphenol $^1$H NMR (200 MHz, DMSO-d$_6$) δ 8.98 (s, 1H), 8.30 (d, 1H), 7.80 (s, 1H), 7.65 (d, 1H), 7.45 (d, 1H), 7.15 (t, 1H), 6.95-6.75 (m, 2H), 4.70 (d, 1H), 3.85 (s, 3H), 3.00-2.80 (m, 1H), 1.85-0.95 (m, 10H).
$^{13}$C NMR (50 MHz, DMSO-d$_6$) δ 147.31, 145.71, 140.23, 135.31, 126.14, 124.33, 123.28, 123.08, 119.41, 116.30, 115.33, 110.96, 110.62, 56.21, 55.49, 33.55, 25.44, 24.43.
HRMS (ESI): m/z 338.1872 (M+H)$^+$; calc. for C$_{20}$H$_{24}$N$_3$O$_2$: 338.1869.

71 MLB133-654A 5-(3-(cyclohexylamino)imidazo[1,2-a]pyridin-2-yl)-2-methoxyphenol $^1$H NMR (200 MHz, CDCl$_3$-CD$_3$OD) δ 8.04 (d, 1H), 7.50-7.25 (m, 3H), 7.15-7.00 (m, 1H), 6.85 (d, 1H), 6.75-6.65 (m, 1H), 3.83 (s, 3H), 3.75-3.45 (m, 1H), 2.95-2.75 (m, 1H), 1.85-0.90 (m, 10H).
$^{13}$C NMR (50 MHz, CDCl$_3$-DMSO-d$_6$) δ 147.18, 145.94, 140.35, 134.58, 125.63, 125.20, 124.38, 122.77, 118.47, 115.46, 113.79, 112.21, 111.22, 56.50, 55.59, 33.78, 25.46, 24.61.
HRMS (ESI): m/z 338.1873 (M+H)$^+$; calc. for C$_{20}$H$_{24}$N$_3$O$_2$: 338.1869.

72 MLB133-654B N-cyclohexyl-2-(3-methylthiophen-2-yl)imidazo[1,2-a]pyridin-3-amine $^1$H NMR (200 MHz, CDCl3) δ 8.12 (d, J=6.9, 1H), 7.56 (d, J=8.9, 1H), 7.28 (d, J=4.3, 1H), 7.20-7.06 (m, 1H), 6.96 (d, J=5.1, 1H), 6.80 (td, J=0.7, 6.8, 1H), 3.46-3.04 (m, 1H), 3.04-2.76 (m, 1H), 2.47 (s, 3H), 2.02-1.43 (m, 5H), 1.36-0.94 (m, 5H).

$^{13}$C NMR (50 MHz, CDCl$_3$) δ 141.26, 135.92, 131.79, 130.54, 129.38, 125.91, 124.12, 123.58, 122.66, 117.33, 111.51, 56.75, 33.92, 25.73, 24.74, 15.24.
HRMS (ESI): m/z 312.1534 (M+H)$^+$; calc. for C$_{18}$H$_{22}$N$_3$S: 312.1534.

73 DG 402-49647 N-cyclohexyl-2-(4-(trifluoromethyl)phenyl)imidazo[1,2-a]pyridin-3-amine $^1$H NMR (200 MHz, CDCl$_3$) δ 8.22 (d, J=8.2, 2H), 8.08 (dt, J=1.0, 6.0, 1H), 7.68 (d, J=8.3, 2H), 7.60-7.45 (m, 1H), 7.15 (ddd, J=1.2, 6.7, 9.0, 1H), 6.80 (td, J=1.0, 6.7, 1H), 3.29-2.67 (m, 2H), 1.96-1.42 (m, 5H), 1.42-0.91 (m, 5H).
$^{13}$C NMR (50 MHz, CDCl$_3$) δ 141.75, 138.01, 135.14, 128.46, 126.91, 125.59, 125.31 (dd, J=3.8, 7.6), 124.45, 124.34, 122.64, 117.57, 111.84, 56.94, 34.22, 25.65, 24.81.
HRMS (ESI): m/z 360.1683 (M+H)$^+$; calc. for C$_{20}$H$_{21}$N$_3$F$_3$: 360.1688.

74 DG 402-49648 2-(6-chloro-2-fluoro-3-methylphenyl)-N-cyclohexylimidazo[1,2-a]pyridin-3-amine $^1$H NMR (400 MHz, CDCl$_3$) δ 8.14 (d, J=6.9, 1H), 7.57 (d, J=9.1, 1H), 7.26-7.05 (m, 3H), 6.82 (dd, J=3.8, 9.7, 1H), 3.02 (s, 1H), 2.82-2.60 (m, 1H), 2.31 (d, J=2.1, 3H), 1.75 (d, J=11.7, 2H), 1.65-1.54 (m, 2H), 1.54-1.40 (m, 1H), 1.22-0.87 (m, 5H).
$^{13}$C NMR (101 MHz, CDCl$_3$) δ 160.71, 158.24, 141.67, 132.21, 131.55, 131.49, 127.21, 124.60, 124.56, 123.95, 123.77, 123.62, 122.76, 117.77, 111.56, 56.31, 33.76, 25.60, 24.61, 14.54.
HRMS (ESI): m/z 358.1481 (M+H)$^+$; calc. for C$_{20}$H$_{22}$N$_3$ClF: 358.1486.

75 DG 402-49649 2-(4-chloro-3-fluorophenyl)-N-cyclohexylimidazo[1,2-a]pyridin-3-amine $^1$H NMR (200 MHz, CDCl$_3$) δ 8.06 (d, J=6.8, 1H), 7.97 (dd, J=1.9, 10.9, 1H), 7.91-7.77 (m, 1H), 7.52 (d, J=9.3, 1H), 7.44 (t, J=8.1, 1H), 7.23-7.08 (m, 1H), 6.81 (td, J=0.8, 6.8, 1H), 3.16-2.79 (m, 2H), 1.99-1.42 (m, 6H), 1.42-0.90 (m, 7H).
$^{13}$C NMR (50 MHz, CDCl$_3$) δ 160.56, 155.65, 141.62, 130.43, 125.07, 124.50, 123.14, 123.07, 122.58, 117.46, 115.11, 114.66, 111.96, 56.91, 34.24, 25.65, 24.83.
HRMS (ESI): m/z 344.1323 (M+H)$^+$; calc. for C$_{19}$H$_{20}$N$_3$FCl: 344.1330.

76 DG 402-49650 2-(3-bromophenyl)-N-cyclohexylimidazo[1,2-a]pyridin-3-amine $^1$H NMR (200 MHz, CDCl$_3$) δ 8.35-8.21 (m, 1H), 8.15-8.04 (m, 1H), 8.04-7.90 (m, 1H), 7.61-7.47 (m, 1H), 7.43 (ddd, J=1.1, 1.9, 7.9, 1H), 7.29 (dd, J=5.4, 10.3, 1H), 7.13 (ddd, J=1.3, 6.7, 9.0, 1H), 6.79 (td, J=1.1, 6.8, 1H), 3.29-2.66 (m, 2H), 1.69 (M, 6H), 1.41-0.74 (m, 7H).
$^{13}$C NMR (50 MHz, CDCl$_3$) δ 141.62, 136.60, 131.01, 130.03, 129.98, 129.89, 125.34, 124.13, 122.69, 122.63, 117.46, 111.72, 56.97, 34.25, 25.70, 24.82.
HRMS (ESI): m/z 370.0911 (M+H)$^+$; calc. for C$_{19}$H$_{21}$N$_3$Br: 370.0919.

77 DG 402-49653 2-(4-bromophenyl)-N-cyclohexylimidazo[1,2-a]pyridin-3-amine $^1$H NMR (200 MHz, CDCl$_3$) δ 8.09-8.00 (m, 1H), 7.94 (d, J=8.6, 2H), 7.58-7.43 (m, 3H), 7.10 (ddd, J=1.3, 6.7, 9.0, 1H), 6.75 (td, J=1.1, 6.8, 1H), 3.01 (s, 2H), 1.93-1.39 (m, 5H), 1.16 (s, 5H).

¹³C NMR (50 MHz, CDCl₃) δ 141.57, 135.62, 133.46, 131.43, 128.49, 124.83, 123.98, 122.55, 121.09, 117.33, 111.58, 56.77, 34.32, 25.66, 24.76.

HRMS (ESI): m/z 370.0926 (M+H)⁺; calc. for $C_{19}H_{21}N_3Br$: 370.0919.

78 DG 402-49655 2-(2-chlorophenyl)-N-(pentan-2-yl)imidazo[1,2-a]pyridin-3-amine ¹H NMR (200 MHz, CDCl₃) δ 8.26-8.03 (m, 1H), 7.77-7.61 (m, 1H), 7.61-7.50 (m, 1H), 7.50-7.41 (m, 1H), 7.41-7.21 (m, 2H), 7.12 (ddd, J=1.1, 6.7, 8.9, 1H), 6.78 (td, J=0.7, 6.7, 1H), 3.33-3.03 (m, 1H), 3.03-2.74 (m, 1H), 1.44-0.99 (m, 4H), 0.84 (d, J=6.3, 3H), 0.75 (dd, J=6.2, 7.4, 3H).

¹³C NMR (50 MHz, CDCl₃) δ 141.51, 134.02, 132.58, 132.41, 129.29, 129.23, 128.97, 126.73, 123.51, 123.37, 122.63, 117.43, 111.41, 53.14, 39.54, 20.79, 18.85, 13.93.

HRMS (ESI): m/z 314.1402 (M+H)⁺; calc. for $C_{18}H_{21}N_3Cl$: 314.1424.

79 DG 402-49657 2-isopropyl-N-(pentan-2-yl)imidazo[1,2-a]pyridin-3-amine

¹H NMR (200 MHz, CDCl₃) δ 8.12-7.92 (m, 1H), 7.59-7.40 (m, 1H), 7.05 (ddd, J=1.2, 6.7, 8.9, 1H), 6.71 (dd, J=0.8, 13.6, 1H), 3.25-2.98 (m, 2H), 2.95-2.56 (m, 1H), 1.63-1.40 (m, 3H), 1.37 (dd, J=2.9, 6.9, 6H), 1.06 (d, J=6.3, 2H), 0.93 (dd, J=5.5, 8.4, 3H).

¹³C NMR (50 MHz, CDCl₃) δ 144.92, 141.51, 123.23, 122.69, 122.36, 117.07, 110.92, 53.66, 40.03, 26.24, 22.73, 21.01, 19.45, 14.24.

HRMS (ESI): m/z 246.1967 (M+H)⁺; calc. for $C_{15}H_{24}N_3$: 246.1970.

80 DG 402-49667 6,8-dichloro-2-(2-chlorophenyl)-N-cyclohexylimidazo[1,2-a]pyridin-3-amine ¹H NMR (400 MHz, CDCl₃) δ 8.13 (d, J=1.8, 1H), 7.75-7.64 (m, 1H), 7.52-7.42 (m, 2H), 7.42-7.29 (m, 4H), 7.24 (d, J=1.8, 1H), 3.29 (s, 1H), 2.66 (dd, J=7.7, 11.3, 1H), 2.01-0.74 (m, 29H).

¹³C NMR (101 MHz, CDCl₃) δ 137.08, 133.13, 132.79, 132.67, 129.64, 129.60, 129.40, 128.19, 127.05, 123.79, 123.63, 119.68, 119.25, 67.07, 56.46, 33.79, 25.53, 24.49.

HRMS (ESI): m/z 394.0643 (M+H)⁺; calc. for $C_{19}H_{19}N_3Cl_3$: 394.0645.

81 DG 402-49663 2-(2-chlorophenyl)-N-cyclohexyl-6-fluoroimidazo[1,2-a]pyridin-3-amine ¹H NMR (400 MHz, CDCl₃) δ 8.13 (d, J=1.8, 1H), 7.71-7.67 (m, 1H), 7.48-7.44 (m, 1H), 7.38-7.33 (m, 2H), 7.24 (d, J=1.8, 1H), 3.33 (d, J=29.8, 1H), 2.66 (s, 1H), 1.77-1.60 (m, 3H), 1.51 (dd, J=14.4, 43.3, 2H), 1.12-0.97 (m, 5H).

¹³C NMR (101 MHz, CDCl₃) δ 154.41, 152.06, 139.17, 136.70, 133.59, 132.41, 129.50, 129.33, 127.59, 127.57, 127.01, 118.12, 118.03, 115.96, 115.70, 109.51, 109.10, 56.28, 33.81, 25.55, 24.55.

HRMS (ESI): m/z 344.1299 (M+H)⁺; calc. for $C_{19}H_{20}N_3ClF$: 344.1330.

82 DG 402-49665 6-chloro-2-(2-chlorophenyl)-N-cyclohexylimidazo[1,2-a]pyridin-3-amine ¹H NMR (200 MHz, CDCl₃) δ 8.25-8.11 (m, 1H), 7.75-7.56 (m, 1H), 7.55-7.39 (m, 2H), 7.39-7.25 (m, 2H), 7.10 (ddd, J=1.2, 1.9, 9.5, 1H), 3.27 (d, J=6.8, 1H), 2.80-2.46 (m, 1H), 1.82-1.34 (m, 5H), 1.23-0.76 (m, 5H).

¹³C NMR (50 MHz, CDCl₃) δ 139.84, 136.39, 133.58, 132.56, 132.38, 129.44, 129.27, 126.88, 126.72, 124.94, 120.67, 120.08, 117.96, 56.36, 33.79, 25.58, 24.52.

HRMS (ESI): m/z 360.1019 (M+H)⁺; calc. for $C_{19}H_{20}N_3Cl_2$: 360.1034.

83 DG 402-49672 N-cyclopentyl-2-(2,4-dichlorophenyl)imidazo[1,2-a]pyridin-3-amine ¹H NMR (200 MHz, CDCl₃) δ 8.16 (dt, J=1.2, 7.3, 1H), 7.63 (d, J=8.3, 1H), 7.58-7.41 (m, 2H), 7.42-7.30 (m, 1H), 7.15 (ddd, J=1.3, 6.7, 9.1, 1H), 6.82 (t, J=6.8, 1H), 3.33 (dt, J=5.7, 11.0, 1H), 3.14 (d, J=6.2, 1H), 1.75-1.37 (m, 6H), 1.37-1.04 (m, 2H).

¹³C NMR (50 MHz, CDCl₃) δ 141.65, 134.28, 134.07, 133.27, 133.21, 132.75, 129.24, 127.27, 127.06, 123.97, 122.72, 117.53, 111.72, 59.36, 33.27, 23.29.

HRMS (ESI): m/z 346.0889 (M+H)⁺; calc. for $C_{18}H_{18}N_3Cl_2$: 346.0878.

84 DG 402-49673 2-(4-bromophenyl)-N-cyclopentylimidazo[1,2-a]pyridin-3-amine ¹H NMR (400 MHz, CDCl₃) δ 8.05 (dt, J=1.1, 6.9, 1H), 8.00-7.89 (m, 2H), 7.61-7.44 (m, 3H), 7.12 (ddd, J=1.3, 6.7, 9.0, 1H), 6.76 (td, J=1.1, 6.8, 1H), 3.72-3.47 (m, 1H), 2.99 (d, J=3.9, 1H), 1.83-1.60 (m, 4H), 1.60-1.49 (m, 2H), 1.49-1.35 (m, 2H).

¹³C NMR (101 MHz, CDCl₃) δ 141.63, 135.83, 133.49, 131.45, 128.62, 125.49, 124.10, 122.47, 121.18, 117.44, 111.67, 59.06, 33.46, 23.57.

HRMS (ESI): m/z 356.0727 (M+H)⁺; calc. for $C_{18}H_{19}N_3Br$: 356.0762.

85 DG 402-49678 2-(3-bromophenyl)-N-cyclopentylimidazo[1,2-a]pyridin-3-amine ¹H NMR (400 MHz, CDCl₃) δ 8.31-8.28 (m, 1H), 8.09 (d, J=6.8, 1H), 8.04-7.97 (m, 1H), 7.52 (dt, J=3.5, 7.8, 1H), 7.43 (ddd, J=0.9, 1.9, 7.9, 1H), 7.32-7.24 (m, 1H), 7.17-7.11 (m, 1H), 6.79 (td, J=0.8, 6.8, 1H), 3.66 (t, J=10.3, 1H), 3.01 (s, 1H), 1.88-1.65 (m, 4H), 1.65-1.53 (m, 2H), 1.53-1.39 (m, 2H).

¹³C NMR (101 MHz, CDCl₃) δ 141.71, 136.63, 135.41, 130.13, 130.10, 130.06, 129.94, 125.80, 125.52, 124.26, 122.70, 122.55, 117.61, 111.82, 59.24, 33.56, 23.61.

HRMS (ESI): m/z 356.0774 (M+H)⁺; calc. for $C_{18}H_{19}N_3Br$: 356.0762.

86 DG 402-49679 2-(4-chloro-3-fluorophenyl)-N-cyclopentylimidazo[1,2-a]pyridin-3-amine ¹H NMR (400 MHz, CDCl₃) δ 8.05 (d, J=6.7, 1H), 7.96 (d, J=10.9, 1H), 7.85 (d, J=8.4, 1H), 7.51 (d, J=9.0, 1H), 7.42 (t, J=8.0, 1H), 7.20-7.07 (m, 1H), 6.79 (t, J=6.7, 1H), 3.88-3.40 (m, 1H), 2.97 (d, J=3.8, 1H), 1.87-1.62 (m, 4H), 1.62-1.52 (m, 2H), 1.52-1.35 (m, 2H).

¹³C NMR (101 MHz, CDCl₃) δ 159.39, 156.93, 141.73, 135.29, 135.22, 134.97, 130.38, 125.70, 124.44, 123.27, 123.23, 122.49, 119.51, 119.33, 117.62, 115.13, 114.90, 111.92, 59.12, 33.54, 23.61.

HRMS (ESI): m/z 330.1173 (M+H)⁺; calc. for $C_{18}H_{18}N_3FCl$: 330.1173.

87 DG 402-49680 2-(6-chloro-2-fluoro-3-methylphenyl)-N-cyclopentylimidazo[1,2-a]pyridin-3-amine $^1$H NMR (400 MHz, CDCl$_3$) δ 8.23-8.08 (m, 1H), 7.56 (ddd, J=1.0, 1.9, 9.1, 1H), 7.23-7.06 (m, 3H), 6.87-6.72 (m, 1H), 3.54-3.27 (m, 1H), 2.96 (d, J=6.4, 1H), 2.39-2.21 (m, 3H), 1.72-1.51 (m, 4H), 1.51-1.37 (m, 2H), 1.37-1.16 (m, 2H).
$^{13}$C NMR (101 MHz, CDCl$_3$) δ 160.78, 158.31, 141.64, 132.36, 132.32, 131.52, 131.45, 129.80, 127.90, 124.58, 124.54, 123.93, 123.74, 123.57, 122.61, 122.11, 121.92, 117.83, 111.52, 59.33, 33.16, 23.24, 14.48, 14.44.
HRMS (ESI): m/z 344.1328 (M+H)$^+$; calc. for C$_{19}$H$_{20}$N$_3$FCl: 344.1330.

88 DG 402-49681 N-cyclopentyl-2-(4-(trifluoromethyl)phenyl)imidazo[1,2-a]pyridin-3-amine $^1$H NMR (400 MHz, CDCl$_3$) δ 8.21 (d, J=8.0, 2H), 8.07 (d, J=6.9, 1H), 7.67 (d, J=7.9, 2H), 7.53 (d, J=9.1, 1H), 7.15 (dd, J=7.2, 8.5, 1H), 6.79 (t, J=6.8, 1H), 3.75-3.50 (m, J=9.6, 1H), 3.04 (d, J=3.2, 1H), 1.87-1.62 (m, 4H), 1.62-1.51 (m, 2H), 1.50-1.36 (m, 2H).
$^{13}$C NMR (101 MHz, CDCl$_3$) δ 141.81, 138.09, 138.08, 135.39, 129.07, 128.75, 127.10, 126.25, 125.69, 125.33, 125.29, 125.25, 125.22, 124.40, 122.56, 117.66, 111.89, 59.20, 33.51, 23.57.
HRMS (ESI): m/z 346.1525 (M+H)$^+$; calc. for C$_{19}$H$_{19}$N$_3$F$_3$: 346.1531.

89 DG 402-49686 N-cyclohexyl-2-(2,4-dichlorophenyl)imidazo[1,2-a]pyridin-3-amine $^1$H NMR (400 MHz, CDCl$_3$) δ 8.14 (ddd, J=0.9, 1.6, 6.9, 1H), 7.64-7.60 (m, 1H), 7.56-7.52 (m, 1H), 7.51-7.48 (m, 1H), 7.38-7.33 (m, 1H), 7.19-7.12 (m, 1H), 6.81 (tt, J=1.8, 9.2, 1H), 3.19 (d, J=6.0, 1H), 2.67 (dd, J=3.8, 9.0, 1H), 1.65 (t, J=11.2, 2H), 1.59 (dd, J=4.6, 8.9, 2H), 1.53-1.42 (m, 1H), 1.17-0.92 (m, 6H).
$^{13}$C NMR (101 MHz, CDCl$_3$) δ 141.75, 134.27, 134.14, 133.34, 133.14, 132.80, 129.29, 127.33, 126.44, 123.93, 122.89, 117.57, 111.70, 56.43, 33.89, 25.62, 24.58.
HRMS (ESI): m/z 360.1025 (M+H)$^+$; calc. for C$_{19}$H$_{20}$N$_3$Cl$_2$: 360.1034.

90 DG 402-49688 N-(1-adamantyl)-2-(2-chlorophenyl)imidazo[1,2-a]pyridin-3-amine $^1$H NMR (400 MHz, CDCl$_3$) δ 8.39-8.34 (m, 1H), 7.75-7.68 (m, 1H), 7.52 (ddd, J=5.0, 6.0, 11.0, 1H), 7.48-7.43 (m, 1H), 7.40-7.29 (m, 2H), 7.17-7.11 (m, 1H), 6.82-6.75 (m, 1H), 3.28-3.11 (m, 1H), 1.95-1.83 (m, 3H), 1.52 (d, J=12.2, 3H), 1.42 (t, J=10.7, 9H).
$^{13}$C NMR (101 MHz, CDCl$_3$) δ 142.21, 137.82, 134.92, 132.85, 132.46, 129.45, 129.04, 126.94, 124.04, 123.94, 123.77, 117.36, 111.21, 55.83, 43.49, 36.17, 29.61.
HRMS (ESI): m/z 378.1731 (M+H)$^+$; calc. for C$_{23}$H$_{25}$N$_3$Cl: 378.1737.

91 DG 402-49690 N-(1-adamantyl)-2-(5-methylisoxazol-3-yl)imidazo[1,2-a]pyridin-3-amine $^1$H NMR (400 MHz, CDCl$_3$) δ 8.30 (dt, J=7.3, 15.7, 1H), 7.50 (dt, J=6.1, 12.2, 1H), 7.16-7.07 (m, 1H), 6.80-6.70 (m, 1H), 6.63-6.56 (m, 1H), 4.17-3.98 (m, 1H), 2.60-2.40 (m, 3H), 1.98 (d, J=20.6, 2H), 1.82-1.70 (m, 5H), 1.62-1.47 (m, 5H).
$^{13}$C NMR (101 MHz, CDCl$_3$) δ 168.66, 159.46, 142.39, 128.08, 126.54, 124.33, 124.13, 117.50, 111.52, 101.16, 57.60, 43.42, 36.20, 29.78, 12.20.
HRMS (ESI): m/z 349.2013 (M+H)$^+$; calc. for C$_{21}$H$_{25}$N$_4$O: 349.2028.

92 DG 402-49683 N-cyclopentyl-2-(2,6-difluorophenyl)imidazo[1,2-a]pyridin-3-amine $^1$H NMR (400 MHz, CDCl$_3$) δ 8.19-8.13 (m, 1H), 7.56 (t, J=10.7, 1H), 7.41-7.29 (m, 1H), 7.19-7.11 (m, 1H), 7.06-6.97 (m, 2H), 6.87-6.75 (m, 1H), 3.48-3.32 (m, 1H), 3.07 (d, J=6.1, 1H), 1.73-1.53 (m, 4H), 1.53-1.38 (m, 2H), 1.38-1.24 (m, 2H).
$^{13}$C NMR (101 MHz, CDCl$_3$) δ 162.09, 162.02, 159.61, 159.54, 142.02, 129.83, 129.72, 129.62, 128.46, 126.59, 123.80, 122.64, 117.88, 111.75, 111.69, 111.66, 111.56, 111.49, 59.42, 33.23, 23.24.
HRMS (ESI): m/z 314.1462 (M+H)$^+$; calc. for C$_{18}$H$_{18}$N$_3$F$_2$: 314.1469.

93 DG 402-49694 N-(1-adamantyl)-2-(3-methylthiophen-2-yl)imidazo[1,2-a]pyridin-3-amine $^1$H NMR (400 MHz, CDCl$_3$) δ 8.28 (dt, J=1.2, 7.0, 1H), 7.51 (dt, J=1.1, 9.1, 1H), 7.27 (d, J=4.8, 1H), 7.12 (ddd, J=1.3, 6.6, 9.0, 1H), 6.93 (d, J=5.1, 1H), 6.76 (td, J=1.1, 6.8, 1H), 3.01 (s, 1H), 2.36 (s, 3H), 1.94 (s, 3H), 1.67-1.34 (m, 12H).
$^{13}$C NMR (101 MHz, CDCl$_3$) δ 142.08, 135.20, 131.03, 130.16, 127.25, 124.57, 123.81, 123.58, 120.05, 117.31, 111.16, 56.25, 43.44, 36.19, 29.68, 15.17.
HRMS (ESI): m/z 364.1836 (M+H)$^+$; calc. for C$_{22}$H$_{26}$N$_3$S: 364.1847.

94 DG 402-49700 2-(2-chlorophenyl)-N-(1-adamantyl)imidazo[2,1-a]isoquinolin-3-amine $^1$H NMR (400 MHz, CDCl$_3$) δ 8.66 (ddd, J=6.1, 6.6, 12.7, 1H), 8.18 (d, J=7.4, 1H), 7.78 (dd, J=1.8, 7.6, 1H), 7.73-7.67 (m, 1H), 7.62-7.50 (m, 2H), 7.48-7.44 (m, 1H), 7.42-7.36 (m, 1H), 7.36-7.29 (m, 1H), 7.05 (t, J=5.0, 1H), 3.23 (s, 1H), 1.90 (s, 3H), 1.66 (d, J=2.9, 3H), 1.51 (s, 2H), 1.46 (d, J=2.4, 8H).
$^{13}$C NMR (101 MHz, CDCl$_3$) δ 139.64, 135.61, 134.88, 132.95, 132.50, 129.60, 129.57, 129.39, 128.86, 128.28, 127.80, 127.76, 127.00, 126.76, 123.88, 122.79, 121.30, 111.80, 55.63, 43.50, 36.12, 29.58.
HRMS (ESI): m/z 428.1896 (M+H)$^+$; calc. for C$_{27}$H$_{27}$N$_3$Cl: 428.1894.

95 DG 402-49702 6-bromo-2-(2-chlorophenyl)-N-cyclohexyl-5-methylimidazo[1,2-a]pyridin-3-amine $^1$H NMR (200 MHz, CDCl$_3$) δ 7.71-7.55 (m, 1H), 7.55-7.42 (m, 1H), 7.42-7.29 (m, 2H), 7.25 (d, J=4.3, 2H), 3.18 (s, 3H), 2.55 (s, 1H), 1.53 (d, J=17.9, 5H), 1.16-0.65 (m, 5H).
$^{13}$C NMR (50 MHz, CDCl$_3$) δ 142.05, 138.18, 137.93, 135.11, 134.05, 132.69, 132.49, 129.40, 129.23, 128.26, 126.90, 116.25, 109.91, 58.69, 33.04, 25.68, 24.68, 17.94.
HRMS (ESI): m/z 418.0676 (M+H)$^+$; calc. for C$_{20}$H$_{22}$N$_3$ClBr: 418.0686.

96 DG 402-49704 2-(2-chlorophenyl)-3-(cyclohexylamino)imidazo[1,2-a]pyridine-6-carbonitrile $^1$H NMR (400 MHz, CDCl$_3$) δ 8.65-8.55 (m, 1H), 7.68-7.63 (m, 1H), 7.61 (ddd, J=0.9, 3.4, 9.3, 1H), 7.53-7.46 (m, 1H), 7.43-7.32 (m, 2H), 7.27-7.19 (m, 1H), 3.53-3.13 (m, 1H), 2.86-2.55 (m, 1H), 1.60 (dd, J=23.5, 47.2, 5H), 1.20-0.95 (m, 5H).

$^{13}$C NMR (101 MHz, CDCl$_3$) δ 140.47, 137.48, 132.83, 132.57, 132.30, 129.76, 129.62, 129.36, 127.41, 127.07, 123.24, 118.50, 117.05, 97.81, 56.58, 33.76, 25.44, 24.45.

HRMS (ESI): m/z 351.1361 (M+H)$^+$; calc. for C$_{20}$H$_{20}$N$_4$Cl: 351.1376.

97 DG 402-49754 2-(2-chlorophenyl)-N-cyclohexylimidazo[1,2-a]quinolin-1-amine $^1$H NMR (400 MHz, CDCl$_3$) δ 9.44 (dt, J=5.7, 11.5, 1H), 7.74 (dt, J=4.5, 9.0, 1H), 7.71-7.65 (m, 1H), 7.62-7.55 (m, 1H), 7.52-7.47 (m, 1H), 7.46-7.40 (m, 3H), 7.39-7.36 (m, 1H), 7.36-7.33 (m, 1H), 3.60-3.39 (m, 1H), 2.86-2.67 (m, 1H), 1.74 (dd, J=12.6, 18.3, 2H), 1.60-1.36 (m, 3H), 1.11-0.86 (m, 5H).

$^{13}$C NMR (101 MHz, CDCl$_3$) δ 140.68, 134.79, 132.65, 131.29, 129.57, 129.44, 129.34, 129.05, 128.43, 127.66, 127.36, 127.01, 125.69, 124.42, 124.33, 117.52, 117.11, 56.59, 33.10, 25.58, 24.62.

HRMS (ESI): m/z 376.1576 (M+H)$^+$; calc. for C$_{23}$H$_{23}$N$_3$Cl: 376.1581.

98 DG 402-49708 6-bromo-2-(2-chlorophenyl)-N-cyclohexyl-8-methylimidazo[1,2-a]pyridin-3-amine $^1$H NMR (400 MHz, CDCl$_3$) δ 8.22-8.08 (m, 1H), 7.74-7.59 (m, 1H), 7.53-7.41 (m, 1H), 7.41-7.27 (m, 2H), 7.03 (dd, J=1.1, 1.8, 1H), 3.22 (d, J=6.9, 1H), 2.72-2.61 (m, 1H), 2.60 (s, 3H), 1.73-1.40 (m, 6H), 1.17-0.82 (m, 6H).

$^{13}$C NMR (101 MHz, CDCl$_3$) δ 140.39, 135.51, 133.81, 132.77, 132.61, 129.42, 129.25, 128.52, 126.99, 126.84, 125.82, 120.85, 106.62, 56.38, 33.80, 25.59, 24.53, 16.43.

HRMS (ESI): m/z 418.0676 (M+H)$^+$; calc. for C$_{20}$H$_{22}$N$_3$ClBr: 418.0686.

99 DG 402-49710 6-bromo-2-(2-chlorophenyl)-N-cyclohexylimidazo[1,2-a]pyridin-3-amine $^1$H NMR (400 MHz, CDCl3) δ 8.33-8.21 (m, 1H), 7.70-7.56 (m, 1H), 7.52-7.45 (m, 1H), 7.45-7.40 (m, 1H), 7.40-7.29 (m, 2H), 7.20 (dd, J=1.9, 9.5, 1H), 3.25 (d, J=6.9, 1H), 2.66 (dd, J=3.4, 6.5, 1H), 1.75-1.62 (m, 2H), 1.61-1.52 (m, 2H), 1.52-1.39 (m, 1H), 1.18-0.86 (m, 5H).

$^{13}$C NMR (101 MHz, CDCl3) δ 139.99, 136.23, 133.61, 132.62, 132.46, 129.52, 129.35, 127.06, 126.97, 126.62, 123.02, 118.30, 106.65, 56.41, 33.81, 25.58, 24.53.

HRMS (ESI): m/z 404.0512 (M+H)$^+$; calc. for C$_{19}$H$_{20}$N$_3$ClBr: 404.0529.

100 DG 402-49692 N-(1-adamantyl)-2-octylimidazo[1,2-a]pyridin-3-amine $^1$H NMR (400 MHz, CDCl$_3$) δ 8.30-8.09 (m, 1H), 7.43 (dt, J=1.1, 9.0, 1H), 7.04 (ddd, J=1.3, 6.6, 9.0, 1H), 6.69 (td, J=1.1, 6.8, 1H), 2.77-2.70 (m, 2H), 2.05 (d, J=8.4, 3H), 1.79 (dt, J=7.7, 15.7, 2H), 1.72 (d, J=2.5, 6H), 1.64 (d, J=12.3, 3H), 1.57 (d, J=12.3, 3H), 1.45-1.17 (m, 11H), 0.87 (t, J=6.9, 3H).

$^{13}$C NMR (101 MHz, CDCl$_3$) δ 141.92, 141.67, 123.26, 122.92, 122.06, 116.66, 110.52, 55.48, 44.01, 36.27, 31.87, 29.91, 29.73, 29.54, 29.46, 29.25, 27.98, 22.65, 14.06.

HRMS (ESI): m/z 380.3053 (M+H)$^+$; calc. for C$_{25}$H$_{38}$N$_3$: 380.3066.

101 DG 402-49675 2-(2-bromophenyl)-N-cyclopentylimidazo[1,2-a]pyridin-3-amine $^1$H NMR (400 MHz, CDCl$_3$) δ 8.17 (dt, J=1.1, 6.9, 1H), 7.64 (ddd, J=1.3, 4.4, 9.5, 2H), 7.59-7.49 (m, 1H), 7.40 (ddd, J=0.6, 1.2, 7.5, 1H), 7.27-7.20 (m, 1H), 7.18-7.08 (m, 1H), 6.80 (ddd, J=0.6, 1.0, 6.7, 1H), 3.46-3.27 (m, 1H), 3.21 (d, J=6.4, 1H), 1.68-1.48 (m, 4H), 1.48-1.35 (m, 2H), 1.35-1.13 (m, 2H).

$^{13}$C NMR (101 MHz, CDCl$_3$) δ 141.31, 136.72, 136.11, 132.69, 132.53, 129.32, 127.29, 126.48, 123.65, 122.88, 122.68, 117.54, 111.55, 59.30, 33.16, 23.19.

HRMS (ESI): m/z 356.0768 (M+H)$^+$; calc. for C$_{18}$H$_{19}$N$_3$Br: 356.0762.

102 DG 402-49682 N-cyclopentyl-2-(2,6-dichlorophenyl)imidazo[1,2-a]pyridin-3-amine $^1$H NMR (400 MHz, CDCl$_3$) δ 8.16 (d, J=6.9, 1H), 7.67-7.49 (m, 1H), 7.49-7.36 (m, 2H), 7.33-7.21 (m, 1H), 7.19-7.03 (m, 1H), 6.81 (dd, J=3.6, 10.3, 1H), 3.50-3.32 (m, 1H), 2.84 (d, J=6.0, 1H), 1.72-1.53 (m, 4H), 1.53-1.40 (m, 2H), 1.40-1.27 (m, 2H).

$^{13}$C NMR (101 MHz, CDCl$_3$) δ 141.46, 136.35, 132.97, 129.88, 128.01, 127.38, 123.61, 122.70, 117.89, 111.60, 59.41, 33.29, 23.34.

HRMS (ESI): m/z 346.0877 (M+H)$^+$; calc. for C$_{18}$H$_{18}$N$_3$Cl$_2$: 346.0878.

103 DG 402-49696 N-(1-adamantyl)-2-cyclopropylimidazo[1,2-a]pyridin-3-amine $^1$H NMR (400 MHz, CDCl$_3$) δ 8.18 (dt, J=1.2, 6.9, 1H), 7.39 (dt, J=1.1, 9.0, 1H), 7.03 (ddt, J=1.2, 6.7, 9.0, 1H), 6.68 (td, J=1.1, 6.8, 1H), 2.77 (s, 1H), 2.19-1.93 (m, 4H), 1.77 (d, J=2.5, 6H), 1.61 (q, J=12.2, 6H), 1.13-1.03 (m, 2H), 0.99-0.91 (m, 2H).

$^{13}$C NMR (101 MHz, CDCl$_3$) δ 142.47, 141.73, 122.88, 122.75, 122.49, 116.39, 110.46, 55.60, 43.98, 36.27, 29.73, 8.87, 8.18.

HRMS (ESI): m/z 308.2128 (M+H)$^+$; calc. for C$_{20}$H$_{26}$N$_3$: 308.2127.

104 DG402-49748 5-chloro-2-(2-chlorophenyl)-N-cyclohexylimidazo[1,2-a]pyridin-3-amine $^1$H NMR (400 MHz, CDCl$_3$) δ 7.63-7.56 (m, 1H), 7.49 (dddd, J=1.3, 1.8, 4.5, 5.0, 2H), 7.39-7.30 (m, 2H), 7.08-6.99 (m, 1H), 6.80-6.73 (m, 1H), 3.31 (d, J=6.8, 1H), 2.81 (s, 1H), 1.67 (d, J=12.5, 2H), 1.52 (s, 2H), 1.45 (s, 1H), 1.06 (t, J=10.4, 3H), 0.89 (d, J=10.1, 2H).

$^{13}$C NMR (101 MHz, CDCl$_3$) δ 143.62, 137.52, 133.65, 133.24, 132.59, 129.49, 129.25, 128.24, 126.67, 125.99, 123.55, 116.77, 114.06, 58.58, 32.78, 25.67, 24.50.

HRMS (ESI): m/z 360.1014 (M+H)$^+$; calc. for C$_{19}$H$_{20}$N$_3$Cl$_2$: 360.1034.

105 DG 402-49758 2-(2-bromophenyl)-N-cyclohexylimidazo[2,1-a]isoquinolin-3-amine $^1$H NMR (400 MHz, CDCl$_3$) δ 8.66 (d, J=8.0, 1H), 7.99 (dd, J=1.3, 7.3, 1H), 7.75-7.63 (m, 3H), 7.63-7.56 (m, 1H), 7.56-7.48 (m, 1H), 7.42 (ddd, J=1.4, 4.5, 7.6, 1 H), 7.32-7.18 (m, 1H), 7.06 (d, J=7.3, 1H), 3.29 (d, J=6.9, 1H), 2.70 (s, 1H), 1.79-1.64 (m, 2H), 1.57 (s, 2H), 1.51-1.42 (m, 1H), 1.17-0.97 (m, 4H), 0.95-0.75 (m, 1H).

¹³C NMR (101 MHz, CDCl₃) δ 138.83, 136.11, 134.54, 132.88, 132.55, 129.39, 129.25, 127.85, 127.74, 127.62, 127.50, 126.87, 123.95, 123.13, 122.73, 120.43, 112.28, 56.86, 33.75, 25.62, 24.53.

HRMS (ESI): m/z 420.1063 (M+H)⁺; calc. for C₂₃H₂₃N₃Br: 420.1075.

106 SG389-832C N-cyclohexyl-2-(2,5-dichlorophenyl)imidazo[1,2-a]pyridin-3-amine ¹H NMR (200 MHz, CDCl₃) δ 8.15 (d, J=7.1, 1H), 7.69 (d, J=2.5, 1H), 7.52 (d, J=9.1, 1H), 7.46-7.06 (m, 5H), 6.84 (d, J=6.7, 1H), 2.25-2.07 (m, 5H), 1.83-1.43 (m, 12H), 1.41-0.96 (m, 25H), 0.96-0.73 (m, 16H).

¹³C NMR (50 MHz, CDCl₃) δ 138.21, 132.79, 132.26, 130.77, 130.64, 130.58, 129.45, 129.10, 128.52, 124.09, 122.92, 117.54, 111.80, 56.52, 33.93, 31.59, 24.61.

HRMS (ESI): m/z 360.1037 (M+H)⁺; calc. for C₁₉H₂₀N₃Cl₂: 360.1034.

107 SG389-834H N-cyclopentyl-2-(2,4-difluorophenyl)imidazo[1,2-a]pyridin-3-amine ¹H NMR (400 MHz, CDCl₃) δ 8.15 (dt, J=1.0, 6.9, 1H), 7.60 (d, J=8.3, 1H), 7.51 (dt, J=0.9, 9.0, 1H), 7.48 (d, J=2.1, 1H), 7.34-7.30 (m, 1H), 7.14 (ddd, J=1.2, 6.7, 9.0, 1H), 6.79 (td, J=0.9, 6.7, 1H), 3.39-3.27 (m, 1H), 3.20 (s, 1H), 1.68-1.48 (m, 4H), 1.48-1.34 (m, 2H), 1.34-1.17 (m, 2H).

¹³C NMR (101 MHz, CDCl₃) δ 141.30, 134.09, 133.50, 133.02, 132.97, 132.30, 129.01, 127.05, 126.87, 123.99, 122.53, 117.06, 111.62, 58.99, 32.94, 22.99.

HRMS (ESI): m/z 314.1473 (M+H)⁺; calc. for C₁₈H₁₈N₃F₂: 314.1469.

108 SG389-832A 2-(3-chlorophenyl)-N-cyclohexylimidazo[1,2-a]pyridin-3-amine

¹H NMR (200 MHz, CDCl₃) δ 8.21-8.10 (m, 1H), 8.07 (d, J=6.9, 1H), 8.01-7.82 (m, 1H), 7.52 (d, J=9.1, 1H), 7.43-7.20 (m, 2H), 7.20-7.02 (m, 1H), 6.78 (t, J=6.8, 1H), 3.20-2.75 (m, 2H), 1.99-1.42 (m, 6H), 1.42-0.92 (m, 5H).

¹³C NMR (50 MHz, CDCl₃) δ 141.55, 136.30, 135.18, 134.39, 129.55, 127.06, 127.02, 125.17, 124.86, 124.08, 122.60, 117.40, 111.66, 56.90, 34.19, 25.67, 24.78.

HRMS (ESI): m/z 326.1423 (M+H)⁺; calc. for C₁₉H₂₁N₃Cl: 326.1424.

109 SG389-832D N-cyclohexyl-2-(2,6-dichlorophenyl)imidazo[1,2-a]pyridin-3-amine ¹H NMR (200 MHz, CDCl₃) δ 8.15 (d, J=6.9, 1H), 7.56 (d, J=9.1, 1H), 7.48-7.35 (m, 2H), 7.28 (dd, J=6.6, 8.8, 1H), 7.21-7.02 (m, 1H), 6.81 (td, J=0.7, 6.7, 1H), 3.03-2.55 (m, 2H), 1.93-1.40 (m, 8H), 1.39-0.96 (m, 14H), 0.96-0.65 (m, 8H).

¹³C NMR (50 MHz, CDCl₃) δ 141.53, 136.31, 133.06, 129.85, 128.90, 128.00, 126.72, 123.56, 122.85, 117.83, 111.55, 56.58, 33.84, 25.69, 24.60.

HRMS (ESI): m/z 360.1042 (M+H)⁺; calc. for C₁₉H₂₀N₃Cl₂: 360.1034.

110 SG389-832E N-cyclohexyl-2-(2,6-difluorophenyl)imidazo[1,2-a]pyridin-3-amine ¹H NMR (400 MHz, CDCl₃) δ 8.13 (dt, J=1.2, 6.9, 1H), 7.57 (dt, J=1.1, 9.1, 1H), 7.34 (tt, J=6.4, 8.3, 1H), 7.14 (ddd, J=1.3, 6.6, 9.1, 1H), 7.03 (t, J=8.1, 2H), 6.80 (td, J=1.1, 6.8, 1H), 3.12 (s, 1H), 2.71 (s, 1H), 1.84-1.66 (m, 2H), 1.66-1.54 (m, 2H), 1.54-1.42 (m, 1H), 1.21-0.92 (m, 6H).

¹³C NMR (101 MHz, CDCl₃) δ 161.92, 161.85, 159.44, 159.37, 141.97, 129.75, 129.64, 129.54, 127.74, 126.45, 123.75, 122.71, 117.69, 111.72, 111.59, 111.46, 56.40, 33.87, 25.53, 24.64.

HRMS (ESI): m/z 328.1630 (M+H)⁺; calc. for C₁₉H₂₀N₃F₂: 328.1625.

111 DG 402-49756 N-cyclohexyl-2-(2-fluorophenyl)imidazo[2,1-a]isoquinolin-3-amine ¹H NMR (400 MHz, CDCl₃) δ 8.66 (ddd, J=0.7, 1.3, 2.6, 1H), 8.04-7.94 (m, 2H), 7.70 (dd, J=0.9, 8.0, 1H), 7.66-7.57 (m, 1H), 7.54 (ddd, J=1.4, 7.2, 7.7, 1H), 7.40-7.27 (m, 2H), 7.20-7.12 (m, 1H), 7.05 (d, J=7.2, 1H), 3.49 (s, 1H), 2.72 (s, 1H), 1.78 (s, 2H), 1.62 (s, 2H), 1.51 (s, 1H), 1.10 (d, J=7.7, 5H).

¹³C NMR (101 MHz, CDCl₃) δ 160.62, 158.21, 139.52, 131.50, 129.37, 128.88, 128.79, 127.86, 127.82, 126.90, 124.76, 123.94, 122.75, 120.52, 119.88, 115.68, 115.45, 112.25, 57.26, 33.96, 25.63, 24.83.

HRMS (ESI): m/z 360.1857 (M+H)⁺; calc. for C₂₃H₂₃N₃F: 360.1876.

112 SG389-816A N-(2-chloro-6-methylphenyl)-2-cyclopropylimidazo[1,2-a]pyridin-3-amine ¹H NMR (200 MHz, CDCl₃) δ 7.91 (d, J=6.8, 1H), 7.46 (d, J=9.0, 1H), 7.25 (d, J=6.8, 1H), 7.17-7.00 (m, 1H), 6.93 (d, J=7.1, 1H), 6.77 (dd, J=6.7, 14.2, 2H), 5.87 (s, 1H), 2.85 (s, 1H), 1.79-1.49 (m, 3H), 1.16-0.85 (m, 2H), 0.85-0.54 (m, 2H).

¹³C NMR (50 MHz, CDCl₃) δ 142.56, 141.29, 139.91, 130.63, 128.32, 127.15, 123.48, 123.38, 121.58, 121.34, 120.13, 116.68, 111.66, 18.16, 7.62, 7.17.

HRMS (ESI): m/z 298.1123 (M+H)⁺; calc. for C₁₇H₁₇N₃Cl: 298.111.

113 SG389-832B N-cyclohexyl-2-(2-fluorophenyl)imidazo[1,2-a]pyridin-3-amine

¹H NMR (200 MHz, CDCl₃) δ 8.15 (d, J=6.9, 1H), 7.92 (td, J=2.3, 7.6, 1H), 7.54 (d, J=9.1, 1H), 7.22 (m, 4H), 6.79 (t, J=6.7, 1H), 3.45 (t, J=7.8, 1H), 2.91-2.46 (m, 1H), 1.88-1.34 (m, 5H), 1.21-0.83 (m, 5H).

¹³C NMR (50 MHz, CDCl₃) δ 141.74, 131.58, 131.49, 129.15, 128.98, 124.60, 124.54, 123.65, 122.88, 117.38, 115.76, 115.29, 111.44, 56.65, 34.01, 25.66, 24.79.

HRMS (ESI): m/z 310.1724 (M+H)⁺; calc. for C₁₉H₂₁N₃F: 310.1720.

114 SG389-834A 2-(3-chlorophenyl)-N-cyclopentylimidazo[1,2-a]pyridin-3-amine ¹H NMR (400 MHz, CDCl₃) δ 8.13 (t, J=1.9, 1H), 8.04 (dt, J=1.1, 6.9, 1H), 7.94 (dt, J=1.4, 7.7, 1H), 7.50 (dt, J=1.0, 9.0, 1H), 7.33 (t, J=7.8, 1H), 7.25 (ddd, J=1.1, 2.1, 8.0, 1H), 7.15-7.07 (m, 1H), 6.75 (td, J=1.1, 6.8, 1H), 3.70-3.52 (m, 1H), 3.03 (d, J=3.2, 1H), 1.84-1.61 (m, 4H), 1.59-1.49 (m, 2H), 1.49-1.32 (m, 2H).

¹³C NMR (101 MHz, CDCl₃) δ 141.48, 136.13, 135.21, 134.29, 129.53, 127.09, 126.98, 125.72, 124.90, 124.28, 122.49, 117.31, 111.74, 59.01, 33.40, 23.49.

HRMS (ESI): m/z 312.1273 (M+H)⁺; calc. for C₁₈H₁₉N₃Cl: 312.1268.

115 SG389-834C₂-(4-chlorophenyl)-N-cyclopentyl-imidazo[1,2-a]pyridin-3-amine $^1$H NMR (400 MHz, CDCl$_3$) δ 8.08 (dt, J=1.2, 6.9, 1H), 8.04-7.98 (m, 2H), 7.52 (dt, J=1.0, 9.1, 1H), 7.42-7.37 (m, 2H), 7.14 (ddd, J=1.3, 6.7, 9.0, 1H), 6.79 (td, J=1.1, 6.8, 1H), 3.62 (s, 1H), 3.02 (s, 1H), 1.83-1.62 (m, 4H), 1.62-1.50 (m, 2H), 1.50-1.38 (m, 2H).

$^{13}$C NMR (101 MHz, CDCl$_3$) δ 141.49, 135.58, 133.05, 132.74, 128.58, 128.33, 125.47, 124.38, 122.54, 117.29, 111.85, 59.05, 33.45, 23.56.

HRMS (ESI): m/z 312.1273 (M+H)$^+$; calc. for C$_{18}$H$_{19}$N$_3$Cl: 312.1268.

116 CW23836 2-(2-chlorophenyl)-3-(cyclohexylamino)imidazo[1,2-a]pyridine-5-carbonitrile $^1$H NMR (400 MHz, CDCl$_3$) δ 7.80 (dd, J=0.9, 9.0, 1H), 7.62 (dt, J=3.1, 5.4, 1H), 7.54-7.47 (m, 1H), 7.45-7.34 (m, 3H), 7.17 (dd, J=7.1, 8.9, 1H), 3.33 (d, J=7.1, 1H), 2.79 (d, J=3.3, 1H), 1.73 (d, J=10.2, 2H), 1.55 (d, J=3.8, 3H), 1.44 (d, J=13.8, 1H), 1.04 (dd, J=10.2, 19.7, 5H).

$^{13}$C NMR (101 MHz, CDCl$_3$) δ 141.06, 138.44, 133.09, 132.37, 129.80, 129.66, 128.09, 127.08, 124.31, 124.30, 122.94, 121.90, 113.97, 108.02, 57.24, 32.67, 25.60, 24.54.

117 SG389-812 N-(3-chlorophenyl)-2-isopropylimidazo[1,2-a]pyridin-3-amine $^1$H NMR (200 MHz, CDCl$_3$) δ 7.78 (d, J=6.8, 1H), 7.56 (d, J=9.0, 1H), 7.25-7.11 (m, 1H), 7.06 (t, J=8.0, 1H), 6.86-6.61 (m, 2H), 6.51 (t, J=2.0, 1H), 6.37 (dd, J=2.2, 8.1, 1H), 5.81 (s, 1H), 3.27-2.83 (m, 1H), 1.29 (d, J=6.9, 6H).

$^{13}$C NMR (50 MHz, CDCl$_3$) δ 148.27, 146.94, 142.60, 135.34, 130.53, 124.27, 122.19, 119.44, 117.33, 116.27, 113.16, 111.83, 111.28, 26.71, 22.22.

HRMS (ESI): m/z 286.1118 (M+H)$^+$; calc. for C$_{16}$H$_{17}$N$_3$Cl: 286.111.

118 SG389-834B 2-(2-chlorophenyl)-N-cyclopentyl-imidazo[1,2-a]pyridin-3-amine $^1$H NMR (200 MHz, CDCl$_3$) δ 8.23-8.13 (m, 1H), 7.76-7.62 (m, 1H), 7.62-7.42 (m, 2H), 7.42-7.23 (m, 2H), 7.15 (ddd, J=1.3, 6.8, 9.1, 1H), 6.81 (td, J=1.0, 6.8, 1H), 3.34 (dt, J=5.0, 10.2, 1H), 3.21 (d, J=6.4, 1H), 2.21-1.82 (m, 1H), 1.72-1.04 (m, 7H).

$^{13}$C NMR (50 MHz, CDCl$_3$) δ 141.55, 134.01, 132.66, 132.57, 129.44, 129.11, 127.00, 126.87, 123.74, 122.71, 117.56, 111.60, 59.42, 33.24, 23.28.

HRMS (ESI): m/z 312.1270 (M+H)$^+$; calc. for C$_{18}$H$_{19}$N$_3$Cl: 312.1268.

119 SG389-816B N-(2-chloro-6-methylphenyl)-2-isopropylimidazo[1,2-a]pyridin-3-amine $^1$H NMR (200 MHz, CDCl$_3$) δ 8.02 (dd, J=1.1, 6.8, 1H), 7.56 (d, J=9.0, 1H), 7.26 (d, J=7.8, 1H), 7.20-6.99 (m, 1H), 6.93 (d, J=6.7, 1H), 6.88-6.63 (m, 2H), 5.77 (s, 1H), 2.85 (dt, J=6.9, 13.8, 1H), 1.61 (s, 3H), 1.23 (dd, J=7.3, 14.5, 6H).

$^{13}$C NMR (50 MHz, CDCl$_3$) δ 146.67, 141.52, 140.23, 130.59, 128.13, 127.27, 123.44, 123.32, 122.01, 121.38, 118.58, 117.02, 111.81, 26.15, 21.73 (br), 18.03.

HRMS (ESI): m/z 300.1271 (M+H)$^+$; calc. for C$_{17}$H$_{19}$N$_3$Cl: 300.1268.

120 SG389-816C N-(2-chloro-6-methylphenyl)-2-ethylimidazo[1,2-a]pyridin-3-amine $^1$H NMR (200 MHz, CDCl$_3$) δ 8.14-7.91 (m, 1H), 7.52 (d, J=9.0, 1H), 7.26 (d, J=6.1, 1H), 7.21-7.03 (m, 1H), 6.94 (d, J=7.1, 1H), 6.81 (t, J=7.6, 2H), 5.76 (s, 1H), 2.50 (dd, J=7.6, 15.1, 2H), 1.62 (s, 3H), 1.14 (t, J=7.6, 3H).

$^{13}$C NMR (50 MHz, CDCl$_3$) δ 142.86, 141.53, 140.10, 130.61, 128.49, 127.27, 123.58, 123.46, 122.01, 121.58, 119.58, 117.02, 111.86, 20.34, 18.11, 12.84.

HRMS (ESI): m/z 286.1117 (M+H)$^+$; calc. for C$_{16}$H$_{17}$N$_3$Cl: 286.1111.

121 SG389-834G N-cyclopentyl-2-(2,5-dichlorophenyl)imidazo[1,2-a]pyridin-3-amine $^1$H NMR (400 MHz, CDCl$_3$) δ 8.16 (dt, J=1.2, 6.9, 1H), 7.67 (d, J=2.6, 1H), 7.49 (dt, J=1.1, 9.1, 1H), 7.39 (d, J=8.6, 1H), 7.29 (dd, J=2.6, 8.6, 1H), 7.17 (ddd, J=1.3, 6.7, 9.1, 1H), 6.82 (tt, J=3.2, 6.5, 1H), 3.37 (d, J=25.1, 1H), 3.18 (s, 1H), 2.02-1.88 (m, 1H), 1.70-1.50 (m, 4H), 1.50-1.37 (m, 2H), 1.37-1.19 (m, 2H).

$^{13}$C NMR (101 MHz, CDCl$_3$) δ 141.47, 135.21, 132.65, 132.04, 130.71, 130.45, 129.10, 128.93, 128.48, 124.32, 122.70, 117.19, 111.87, 59.24, 33.10, 23.10.

HRMS (ESI): m/z 346.0878 (M+H)$^+$; calc. for C$_{18}$H$_{18}$N$_3$Cl$_2$: 346.0878.

122 SG389-832F N-cyclohexyl-2-(2,4,5-trifluorophenyl)imidazo[1,2-a]pyridin-3-amine $^1$H NMR (400 MHz, CDCl$_3$) δ 8.14 (dt, J=1.1, 6.9, 1H), 7.57 (dt, J=1.1, 9.1, 1H), 7.35 (tt, J=6.4, 8.4, 1H), 7.15 (ddd, J=1.3, 6.6, 9.1, 1H), 7.03 (t, J=8.1, 1H), 6.81 (td, J=1.1, 6.8, 1H), 3.11 (s, 1H), 2.67 (m, 1H), 1.75 (m, 2H), 1.69-1.56 (m, 2H), 1.56-1.38 (m, 1H), 1.07 (m, 5H).

$^{13}$C NMR (101 MHz, CDCl$_3$) δ 161.95, 161.88, 159.48, 159.41, 142.03, 129.69, 123.82, 122.76, 117.76, 111.78, 111.65, 111.52, 56.46, 34.04, 25.58, 24.70.

HRMS (ESI): m/z 346.1534 (M+H)$^+$; calc. for C$_{19}$H$_{19}$N$_3$F$_3$: 346.1531.

123 SG389-834E N-cyclopentyl-2-(2-fluorophenyl)imidazo[1,2-a]pyridin-3-amine $^1$H NMR (200 MHz, CDCl$_3$) δ 8.15 (d, J=6.9, 1H), 7.92 (td, J=2.2, 7.5, 1H), 7.53 (d, J=9.0, 1H), 7.29 (ddd, J=4.8, 8.8, 13.0, 2H), 7.13 (dd, J=9.4, 16.2, 2H), 6.75 (t, J=6.3, 1H), 3.55-3.15 (m, 2H), 1.77-1.09 (m, 8H).

$^{13}$C NMR (50 MHz, CDCl$_3$) δ 161.82, 156.95, 141.45, 131.43, 131.35, 129.31, 129.14, 124.53, 124.46, 124.17, 122.70, 116.93, 115.65, 115.18, 111.70, 59.30, 33.09, 23.16.

HRMS (ESI): m/z 296.1566 (M+H)$^+$; calc. for C$_{18}$H$_{19}$N$_3$F: 296.1563.

124 SM60 N,2-dicyclohexylimidazo[1,2-a]pyridin-3-amine $^1$H NMR (200 MHz, CDCl$_3$) δ 8.07-7.97 (m, 1H), 7.53-7.43 (m, 1H), 7.04 (ddd, J=1.2, 6.5, 8.9, 1H), 6.71 (td, J=0.8, 6.6, 1H), 3.02-2.59 (m, 2H), 2.03-1.51 (m, 13H), 1.51-1.00 (m, 8H).

$^{13}$C NMR (50 MHz, CDCl3) δ 144.01, 141.36, 138.21, 122.68, 122.43, 116.98, 110.93, 57.21, 36.47, 34.28, 33.02, 26.91, 26.04, 25.86, 24.95.

HRMS (ESI): m/z 298.2261 (M+H)$^+$; calc. for $C_{19}H_{28}N_3$: 298.2283.

125 SM2 N-cyclohexyl-2-(4-fluorophenyl)imidazo[1,2-a]pyridin-3-amine $^1$H NMR (200 MHz, CDCl$_3$) δ 8.13-7.92 (m, 2H), 7.52 (dt, J=1.0, 9.1, 1H), 7.22-6.97 (m, 2H), 6.77 (td, J=1.1, 6.8, 1H), 3.31-2.47 (m, 2H), 1.93-1.40 (m, 4H), 1.40-0.86 (m, 4H).

$^{13}$C NMR (50 MHz, CDCl$_3$) δ 164.7, 160.0, 142.1, 131.3, 129.6, 129.4, 124.9, 124.0, 123.4, 117.9, 116.4, 115.7, 112.2, 57.3, 35.3, 26.1, 25.0.

HRMS (ESI): m/z 310.1721 (M+H)$^+$; calc. for $C_{19}H_{21}N_3F$: 310.1720.

126 SM61 N,2-dicyclohexyl-8-methylimidazo[1,2-a]pyridin-3-amine $^1$H NMR (200 MHz, CDCl$_3$) δ 7.89 (dd, J=0.9, 7.0, 1H), 6.83 (d, J=6.8, 1H), 6.61 (t, J=6.8, 1H), 3.01-2.65 (m, 2H), 2.57 (s, 3H), 2.05-1.52 (m, 15H), 1.52-1.32 (m, 4H), 1.32-1.02 (m, 6H).

$^{13}$C NMR (50 MHz, CDCl$_3$) δ 143.45, 138.22, 126.60, 123.69, 121.57, 120.35, 110.81, 57.34, 37.09, 34.29, 32.90, 26.95, 25.96, 25.89, 24.99, 16.93.

HRMS (ESI): m/z 312.2404 (M+H)$^+$; calc. for $C_{20}H_{30}N_3$: 312.2440.

127 SM62 N,2-dicyclohexyl-7-methylimidazo[1,2-a]pyridin-3-amine $^1$H NMR (200 MHz, CDCl$_3$) δ 7.89 (d, J=7.2, 1H), 7.23 (s, 1H), 6.54 (dd, J=1.3, 6.8, 1H), 2.98-2.55 (m, 2H), 2.35 (s, 3H), 1.96-1.66 (m, 10H), 1.66-1.48 (m, 3H), 1.48-1.30 (m, 3H), 1.30-1.00 (m, 5H).

$^{13}$C NMR (50 MHz, CDCl$_3$) δ 137.08, 133.51, 128.81, 126.28, 121.76, 115.49, 113.53, 57.35, 36.49, 34.25, 33.00, 26.94, 26.06, 25.89, 24.96, 21.23.

HRMS (ESI): m/z 312.2409 (M+H)$^+$; calc. for $C_{20}H_{30}N_3$: 312.2440.

128 SM63 N,2-dicyclohexyl-6-methylimidazo[1,2-a]pyridin-3-amine $^1$H NMR (200 MHz, CDCl$_3$) δ 7.77 (s, 1H), 7.37 (d, J=9.1, 1H), 6.89 (dd, J=1.7, 9.1, 1H), 2.97-2.78 (m, 2H), 2.31 (s, 3H), 2.06-1.49 (m, 13H), 1.34 (m, 8H).

$^{13}$C NMR (50 MHz, CDCl$_3$) δ 143.91, 140.49, 125.77, 123.03, 120.41, 120.11, 116.36, 57.13, 36.46, 34.26, 33.04, 26.94, 26.06, 25.88, 24.97, 18.38.

HRMS (ESI): m/z 312.2408 (M+H)$^+$; calc. for $C_{20}H_{30}N_3$: 312.2440.

129 SM64 N,2-dicyclohexyl-5-methylimidazo[1,2-a]pyridin-3-amine $^1$H NMR (200 MHz, CDCl$_3$) δ 7.32 (d, J=8.2, 1H), 7.07-6.74 (m, 1H), 6.34 (d, J=6.8, 1H), 2.88 (s, 3H), 2.70 (m, 2H), 2.00-1.53 (m, 13H), 1.52-0.98 (m, 8H).

$^{13}$C NMR (50 MHz, CDCl$_3$) δ 146.00, 143.08, 135.88, 124.67, 122.94, 115.28, 112.64, 59.65, 36.23, 33.44, 32.87, 26.93, 25.96, 25.15, 19.76.

HRMS (ESI): m/z 312.2428 (M+H)$^+$; calc. for $C_{20}H_{30}N_3$: 312.2440.

130 SM66 2-cyclohexyl-N-cyclopentylimidazo[1,2-a]pyridin-3-amine $^1$H NMR (200 MHz, CDCl$_3$) δ 8.03 (dd, J=0.8, 6.7, 1H), 7.47 (dd, J=0.9, 9.0, 1H), 7.13-6.90 (m, 1H), 6.70 (t, J=6.7, 1H), 3.59 (m, 1H), 3.00-2.49 (m, 1H), 2.25-0.94 (m, 19H).

$^{13}$C NMR (50 MHz, CDCl$_3$) δ 144.25, 141.35, 123.99, 122.73, 122.30, 117.01, 110.94, 59.92, 36.53, 33.53, 33.00, 26.91, 26.03, 23.60.

HRMS (ESI): m/z 284.2106 (M+H)$^+$; calc. for $C_{18}H_{26}N_3$: 284.2127.

131 SM67 2-cyclohexyl-N-cyclopentyl-8-methylimidazo[1,2-a]pyridin-3-amine $^1$H NMR (200 MHz, CDCl$_3$) δ 7.91 (d, J=6.3, 1H), 6.84 (d, J=6.8, 1H), 6.62 (t, J=6.7, 1H), 3.59 (m, 1H), 2.99-2.64 (m, 1H), 2.57 (s, 3H), 2.16-0.77 (m, 19H).

$^{13}$C NMR (50 MHz, CDCl$_3$) δ 143.58, 126.58, 124.38, 123.88, 121.70, 120.19, 110.86, 60.00, 37.06, 33.52, 32.84, 26.92, 25.94, 23.60, 16.88.

HRMS (ESI): m/z 298.2234 (M+H)$^+$; calc. for $C_{19}H_{28}N_3$: 298.2283.

132 SM68 2-cyclohexyl-N-cyclopentyl-7-methylimidazo[1,2-a]pyridin-3-amine $^1$H NMR (200 MHz, CDCl$_3$) δ 7.92 (d, J=6.5, 1H), 7.26 (d, J=6.4, 1H), 6.57 (t, J=6.6, 1H), 2.88-2.61 (m, 1H), 2.29 (s, 3H), 2.08-1.31 (m, 12H), 1.31-1.00 (m, 7H).

$^{13}$C NMR (50 MHz, CDCl3) δ 144.2, 142.6, 134.4, 123.3, 122.6, 116.1, 115.3, 60.8, 37.4, 35.38, 34.3, 27.2, 26.5, 25.7, 21.6.

HRMS (ESI): m/z 298.2247 (M+H)$^+$; calc. for $C_{19}H_{28}N_3$: 298.2283.

133 SM69 2-cyclohexyl-N-cyclopentyl-6-methylimidazo[1,2-a]pyridin-3-amine $^1$H NMR (200 MHz, CDCl$_3$) δ 7.81 (s, 1H), 7.42 (d, J=9.1, 1H), 6.92 (d, J=9.3, 1H), 3.69-3.48 (m, 1H), 2.91-2.58 (m, 1H), 2.32 (s, 3H), 2.00-0.98 (m, 19H).

$^{13}$C NMR (50 MHz, CDCl$_3$) δ 143.87, 140.64, 139.16, 138.19, 125.96, 123.66, 120.80, 119.99, 116.31, 114.35, 59.76, 36.47, 33.48, 32.97, 29.29, 26.92, 26.02, 25.64, 23.60, 18.33.

HRMS (ESI): m/z 298.2250 (M+H)$^+$; calc. for $C_{19}H_{28}N_3$: 298.2283.

134 SM70 2-cyclohexyl-N-cyclopentyl-5-methylimidazo[1,2-a]pyridin-3-amine $^1$H NMR (200 MHz, CDCl$_3$) δ 7.36 (t, J=7.4, 1H), 7.03-6.78 (m, 1H), 6.35 (t, J=7.3, 1H), 4.01-3.24 (m, 4H), 2.92 (s, 2H), 2.71-2.50 (m, 2H), 2.50-2.07 (m, 4H), 2.04-0.96 (m, 27H).

$^{13}$C NMR (50 MHz, CDCl$_3$) δ 145.55, 136.00, 125.97, 123.29, 122.79, 122.74, 115.31, 115.22, 115.09, 112.86, 112.52, 112.28, 62.69, 36.24, 32.94, 32.89, 26.99, 26.87, 26.01, 23.71, 19.74.

HRMS (ESI): m/z 298.2251 (M+H)$^+$; calc. for $C_{19}H_{28}N_3$: 298.2283.

135 SM52 N-cyclohexyl-2-(1-phenylethyl)imidazo[1,2-a]pyridin-3-amine

¹H NMR (200 MHz, CDCl₃) δ 8.06-7.95 (m, 1H), 7.58-7.44 (m, 1H), 7.44-7.11 (m, 5H), 7.05 (ddd, J=1.2, 6.7, 8.8, 1H), 6.71 (t, J=6.7, 1H), 4.33 (q, J=7.1, 1H), 2.87-2.28 (m, 2H), 1.98-1.43 (m, 8H), 1.43-0.78 (m, 6H).
¹³C NMR (50 MHz, CDCl₃) δ 145.64, 142.00, 141.09, 128.41, 128.35, 127.97, 127.43, 126.01, 122.77, 122.43, 117.07, 111.08, 57.20, 37.99, 34.13, 25.75, 24.90, 24.80, 21.71.
HRMS (ESI): m/z 320.2073 (M+H)⁺; calc. for $C_{21}H_{26}N_3$: 320.2127.

136 SM53 N-cyclohexyl-8-methyl-2-(1-phenylethyl)imidazo[1,2-a]pyridin-3-amine ¹H NMR (200 MHz, CDCl₃) δ 7.98-7.83 (m, 1H), 7.62-7.10 (m, 5H), 6.95-6.83 (m, 1H), 6.64 (t, J=6.8, 1H), 4.42 (q, J=7.1, 1H), 2.65 (s, 3H), 2.52-2.23 (m, 1H), 1.84 (d, J=7.2, 3H), 1.77-1.47 (m, 5H), 1.36-0.90 (m, 5H).
¹³C NMR (50 MHz, CDCl₃) δ 145.60, 141.51, 141.35, 128.28, 127.57, 126.75, 125.95, 124.79, 121.56, 120.39, 110.91, 57.38, 38.31, 34.02, 25.79, 24.92, 21.71, 16.74.
HRMS (ESI): m/z 334.2242 (M+H)⁺; calc. for $C_{22}H_{28}N_3$: 334.2283.

137 SM54 N-cyclohexyl-7-methyl-2-(1-phenylethyl)imidazo[1,2-a]pyridin-3-amine ¹H NMR (200 MHz, CDCl₃) δ 7.92 (m, 1H), 7.42-7.14 (m, 6H), 6.65 (dd, 1H), 4.32 (q, 1H), 2.78 (s, 1H), 2.31 (s, 1H), 1.83 (d, 3H), 1.88-1.54 (m, 5H), 1.29-1.04 (m, 5H).
¹³C NMR (50 MHz, CDCl₃) δ 146.8, 142.0, 134.7, 129.3, 128.4, 128.0, 127.5, 126.8, 123.1, 121.8, 116.7, 115.6, 59.8, 39.5, 34.8, 26.6, 25.3, 23.9, 22.2.
HRMS (ESI): m/z 334.2255 (M+H)⁺; calc. for $C_{22}H_{28}N_3$: 334.2283.

138 SM55 N-cyclohexyl-6-methyl-2-(1-phenylethyl)imidazo[1,2-a]pyridin-3-amine ¹H NMR (200 MHz, CDCl₃) δ 7.84-7.67 (m, 1H), 7.54-7.00 (m, 6H), 6.99-6.78 (m, 1H), 4.30 (q, J=7.1, 1H), 2.89-2.44 (m, 2H), 2.30 (s, 3H), 1.74 (d, J=3.7, 3H), 1.72-1.48 (m, 6H), 1.44-0.83 (m, 5H).
¹³C NMR (50 MHz, CDCl₃) δ 159.24, 145.78, 141.86, 140.19, 128.31, 127.41, 125.93, 125.85, 120.57, 120.08, 116.43, 57.10, 37.98, 34.09, 25.76, 24.91, 21.72, 18.32.
HRMS (ESI): m/z 334.2257 (M+H)⁺; calc. for $C_{22}H_{28}N_3$: 334.2283.

139 SM56 N-cyclohexyl-5-methyl-2-(1-phenylethyl)imidazo[1,2-a]pyridin-3-amine ¹H NMR (200 MHz, CDCl₃) δ 7.59-7.02 (m, 8H), 6.92 (dd, J=6.8, 8.9, 1H), 6.42-6.29 (m, 1H), 4.30 (q, J=7.1, 1H), 3.68 (s, 1H), 2.84 (s, 3H), 1.76 (d, J=7.2, 3H), 1.72-1.46 (m, 4H), 1.46-0.83 (m, 6H).
¹³C NMR (50 MHz, CDCl₃) δ 145.91, 143.89, 142.83, 136.00, 128.24, 127.41, 125.83, 123.11, 115.40, 112.92, 59.27, 37.67, 33.57, 33.44, 25.88, 25.18, 24.95, 21.97, 19.81.
HRMS (ESI): m/z 334.2255 (M+H)⁺; calc. for $C_{22}H_{28}N_3$: 334.2283.

140 SM51 N-cyclopentyl-2-(1-phenylethyl)imidazo[1,2-a]pyridin-3-amine

¹H NMR (200 MHz, CDCl₃) δ 8.08-7.90 (m, 1H), 7.60-7.43 (m, 1H), 7.43-7.11 (m, 5H), 7.06 (ddd, J=1.4, 6.7, 9.0, 1H), 6.71 (td, J=1.2, 6.8, 1H), 4.35 (q, J=7.1, 1H), 3.61-3.22 (m, 1H), 2.65-1.98 (m, 2H), 1.86-1.75 (m, 3H), 1.75-1.05 (m, 9H).
¹³C NMR (50 MHz, CDCl₃) δ 145.64, 142.08, 141.11, 128.74, 128.34, 127.42, 122.79, 122.28, 117.18, 111.11, 59.75, 37.93, 33.57, 33.41, 23.55, 21.77.
HRMS (ESI): m/z 306.1950 (M+H)⁺; calc. for $C_{20}H_{24}N_3$: 306.1970.

141 SM72 N-cyclopentyl-8-methyl-2-(1-phenylethyl)imidazo[1,2-a]pyridin-3-amine ¹H NMR (200 MHz, CDCl₃) δ 7.91 (d, J=7.3, 1H), 7.51-7.10 (m, 5H), 6.89 (d, J=6.8, 1H), 6.65 (t, J=6.7, 1H), 4.43 (q, J=7.2, 1H), 3.44 (dt, J=5.1, 10.2, 1H), 2.65 (s, 3H), 1.83 (d, J=7.2, 3H), 1.79-1.11 (m, 8H).
¹³C NMR (50 MHz, CDCl₃) δ 145.54, 141.38, 128.27, 127.54, 126.79, 125.94, 125.54, 121.71, 120.22, 111.01, 59.93, 38.19, 33.46, 33.36, 23.57, 21.75, 16.74.
HRMS (ESI): m/z 320.2105 (M+H)⁺; calc. for $C_{21}H_{26}N_3$: 320.2127.

142 SM73 N-cyclopentyl-7-methyl-2-(1-phenylethyl)imidazo[1,2-a]pyridin-3-amine ¹H NMR (200 MHz, CDCl₃) δ 7.89 (d, J=6.9, 1H), 7.52-7.01 (m, 5H), 6.54 (dd, J=1.6, 6.9, 1H), 4.32 (q, J=7.2, 1H), 3.45 (dt, J=5.6, 11.0, 1H), 2.35 (s, 3H), 1.77 (d, J=7.2, 3H), 1.73-1.44 (m, 5H), 1.44-1.04 (m, 3H).
¹³C NMR (50 MHz, CDCl₃) δ 145.76, 141.63, 141.59, 133.64, 128.30, 127.43, 125.92, 124.63, 121.61, 115.65, 113.71, 59.86, 37.88, 33.51, 33.38, 23.57, 21.75, 21.19.
HRMS (ESI): m/z 320.2121 (M+H)⁺; calc. for $C_{21}H_{26}N_3$: 320.2127.

143 SM74 N-cyclopentyl-6-methyl-2-(1-phenylethyl)imidazo[1,2-a]pyridin-3-amine ¹H NMR (200 MHz, CDCl₃) δ 7.81-7.73 (m, 1H), 7.55-7.06 (m, 5H), 6.91 (dd, J=1.7, 9.1, 1H), 4.32 (q, J=7.2, 1H), 3.58-3.31 (m, 1H), 2.30 (s, 3H), 1.77 (d, J=7.2, 3H), 1.72-1.09 (m, 8H).
¹³C NMR (50 MHz, CDCl₃) δ 145.81, 141.83, 140.20, 138.23, 128.37, 127.46, 127.31, 126.00, 120.72, 120.02, 116.59, 59.67, 37.97, 33.60, 23.62, 21.83, 18.40.
HRMS (ESI): m/z 320.2095 (M+H)⁺; calc. for $C_{21}H_{26}N_3$: 320.2127.

144 SM75 N-cyclopentyl-5-methyl-2-(1-phenylethyl)imidazo[1,2-a]pyridin-3-amine ¹H NMR (200 MHz, CDCl₃) δ 7.46-7.03 (m, 6H), 6.93 (dd, J=6.9, 8.9, 1H), 6.36 (d, J=6.7, 1H), 4.34 (q, J=7.1, 1H), 3.49 (dt, J=5.7, 11.2, 1H), 2.85 (s, 3H), 1.77 (d, J=7.2, 3H), 1.73-1.07 (m, 8H).
¹³C NMR (50 MHz, CDCl₃) δ 145.96, 143.65, 142.86, 136.02, 128.27, 127.42, 127.01, 125.86, 123.16, 115.49, 112.93, 62.31, 37.53, 33.15, 32.74, 23.74, 23.61, 22.04, 19.68.
HRMS (ESI): m/z 320.2106 (M+H)⁺; calc. for $C_{21}H_{26}N_3$: 320.2127.

145 SM3 N-cyclohexyl-2-(2,3,6-trichlorophenyl)imidazo[1,2-a]pyridin-3-amine

¹H NMR (200 MHz, CDCl₃) δ 8.23-8.07 (m, 1H), 7.62-7.50 (m, 1H), 7.47 (d, J=8.7, 1H), 7.36 (d, J=8.7, 1H), 7.18

(dd, J=1.3, 6.7, 1H), 6.82 (td, J=0.9, 6.7, 1H), 2.77 (m, 2H), 1.85-1.35 (m, 3H), 1.35-0.71 (m, 3H).
¹³C NMR (50 MHz, CDCl₃) δ 141.56, 134.79, 134.48, 133.04, 131.85, 130.54, 128.27, 126.61, 123.79, 122.90, 117.81, 111.69, 56.63, 33.84, 25.63, 24.58.
HRMS (ESI): m/z 394.0645 (M+H)⁺; calc. for C₁₉H₁₉N₃Cl₃: 394.0645.

146 SM4 N-cyclohexyl-2-(2-fluoro-3-methoxyphenyl)imidazo[1,2-a]pyridin-3-amine ¹H NMR (200 MHz, CDCl₃) δ 8.29-8.03 (m, 1H), 7.60-7.39 (m, 2H), 7.33-7.05 (m, 2H), 6.97 (td, J=1.6, 8.2, 1H), 6.77 (td, J=1.1, 6.8, 1H), 3.93 (s, 3H), 3.72-3.26 (m, 1H), 2.91-2.54 (m, 1H), 1.94-1.36 (m, 5H), 1.33-0.81 (m, 5H).
¹³C NMR (50 MHz, CDCl₃) δ 152.17, 148.23, 147.99, 147.32, 142.22, 127.26, 124.54, 123.96, 123.56, 117.67, 112.66, 111.74, 56.95, 56.67, 34.31, 25.93, 25.14.
HRMS (ESI): m/z 340.1824 (M+H)⁺; calc. for C₂₀H₂₃N₃OF: 340.1825.

147 SM6 2-(3-chloro-2-fluorophenyl)-N-cyclohexylimidazo[1,2-a]pyridin-3-amine ¹H NMR (200 MHz, CDCl₃) δ 8.27-8.03 (m, 1H), 7.81 (ddd, J=1.8, 6.6, 8.4, 1H), 7.64-7.47 (m, 1H), 7.40 (ddd, J=1.8, 7.1, 8.0, 1H), 7.31-7.03 (m, 2H), 6.80 (td, J=1.2, 6.8, 1H), 3.56-3.17 (m, 1H), 2.87-2.50 (m, 1H), 1.89-1.33 (m, 5H), 1.10 (d, J=7.0, 5H).
¹³C NMR (50 MHz, CDCl₃) δ 157.31, 152.40, 142.05, 129.94, 129.87, 129.58, 127.10, 124.93, 124.84, 124.01, 122.99, 117.47, 111.64, 56.74, 34.04, 25.62, 24.79.
HRMS (ESI): m/z 344.1329 (M+H)⁺; calc. for C₁₉H₂₀N₃FCl: 344.1330.

148 SM7 2-(4-chlorophenyl)-N-cyclohexylimidazo[1,2-a]pyridin-3-amine

¹H NMR (200 MHz, CDCl₃) δ 8.13-7.98 (m, 3H), 7.53 (d, J=9.0, 1H), 7.46-7.37 (m, 2H), 7.14 (dd, J=7.8, 9.1, 1H), 6.79 (t, J=6.8, 1H), 3.13-2.84 (m, 2H), 1.95-1.46 (m, 6H), 1.22 (m, 4H).
¹³C NMR (50 MHz, CDCl₃) δ 141.65, 133.09, 132.93, 128.58, 128.26, 123.99, 122.60, 117.45, 111.62, 56.87, 34.23, 25.72, 24.82.
HRMS (ESI): m/z 326.1422 (M+H)⁺; calc. for C₁₉H₂₁N₃Cl: 326.1424.

149 SM8 N-cyclohexyl-2-(2-(trifluoromethyl)phenyl)imidazo[1,2-a]pyridin-3-amine ¹H NMR (200 MHz, CDCl₃) δ 8.28-7.99 (m, 1H), 7.85-7.71 (m, 1H), 7.66-7.40 (m, 4H), 7.13 (ddd, J=1.3, 6.7, 9.0, 1H), 6.80 (td, J=1.1, 6.8, 1H), 3.28-2.83 (m, 1H), 2.66 (m, 1H), 1.90-1.35 (m, 5H), 1.23-0.80 (m, 5H).
¹³C NMR (50 MHz, CDCl₃) δ 141.06, 138.17, 135.28, 132.83, 131.21, 128.11, 126.85, 126.14 (q, J=5.1, 1H), 123.49, 122.77, 121.40, 117.59, 111.50, 56.25, 33.81, 25.63, 24.51.
HRMS (ESI): m/z 360.1688 (M+H)⁺; calc. for C₂₀H₂₁N₃F₃: 360.1688.

150 SM11 N-cyclopentyl-2-(4-fluorophenyl)imidazo[1,2-a]pyridin-3-amine

¹H NMR (200 MHz, CDCl₃) δ 8.21-7.90 (m, 3H), 7.55 (dt, J=1.0, 9.1, 1H), 7.22-6.97 (m, 3H), 6.78 (td, J=1.0, 6.8, 1H), 3.63 (m, 1H), 1.93-1.27 (m, 9H).
¹³C NMR (50 MHz, CDCl₃) δ 164.68, 159.78, 141.48, 138.21, 129.01, 128.85, 124.17, 122.53, 117.36, 115.57, 115.15, 111.77, 59.20, 33.55, 23.64.
HRMS (ESI): m/z 296.1560 (M+H)⁺; calc. for C₁₈H₁₉N₃F: 296.1563.

151 SM12 N-cyclopentyl-2-octylimidazo[1,2-a]pyridin-3-amine

¹H NMR (200 MHz, CDCl₃) δ 8.03 (d, J=6.8, 1H), 7.45 (d, J=9.0, 1H), 7.05 (ddd, J=1.2, 6.5, 8.7, 1H), 6.71 (td, J=1.0, 6.8, 1H), 3.71-3.45 (m, 1H), 2.88-2.51 (m, 2H), 1.92-1.67 (m, 7H), 1.67-1.42 (m, 5H), 1.42-1.11 (m, 10H), 0.87 (m, 2H).
¹³C NMR (50 MHz, CDCl₃) δ 141.31, 139.81, 126.46, 122.81, 122.24, 116.83, 110.95, 59.79, 33.55, 31.90, 29.86, 29.67, 29.49, 29.28, 27.51, 23.60, 22.67, 14.08.
HRMS (ESI): m/z 314.2595 (M+H)⁺; calc. for C₂₀H₃₂N₃: 314.2596.

152 SM13 N-cyclopentyl-2-(2,3,6-trichlorophenyl)imidazo[1,2-a]pyridin-3-amine ¹H NMR (200 MHz, CDCl₃) δ 8.21-8.10 (m, 1H), 7.59-7.50 (m, 1H), 7.50-7.41 (m, 1H), 7.41-7.33 (m, 1H), 7.16 (ddd, J=1.0, 6.5, 8.0, 1H), 6.82 (td, J=0.8, 6.7, 1H), 3.56-3.28 (m, 2H), 2.79 (d, J=5.6, 1H), 1.79-1.40 (m, 7H), 1.40-1.04 (m, 4H).
¹³C NMR (50 MHz, CDCl₃) δ 148.09, 141.46, 137.64, 134.80, 134.78, 134.50, 131.85, 130.56, 130.01, 128.88, 128.25, 127.27, 123.88, 122.73, 117.79, 114.22, 111.76, 107.50, 59.43, 33.38, 23.41.
HRMS (ESI): m/z 380.0490 (M+H)⁺; calc. for C₁₈H₁₇N₃Cl₃: 380.0488.

153 SM14 N-cyclopentyl-2-(2-fluoro-3-methoxyphenyl)imidazo[1,2-a]pyridin-3-amine ¹H NMR (200 MHz, CDCl₃) δ 8.14 (d, J=6.9, 1H), 7.65-7.35 (m, 2H), 7.26-7.03 (m, 2H), 6.95 (td, J=1.6, 8.2, 1H), 6.75 (t, J=6.8, 1H), 3.91 (s, 3H), 3.53-3.22 (m, 2H), 1.76-1.07 (m, 8H).
¹³C NMR (50 MHz, CDCl₃) δ 151.87, 147.84, 147.60, 147.01, 141.78, 131.51, 127.51, 124.16, 124.07, 123.62, 122.67, 117.29, 112.37, 111.37, 59.40, 56.29, 33.13, 23.24.
HRMS (ESI): m/z 326.1668 (M+H)⁺; calc. for C₁₉H₂₁N₃OF: 326.1669.

154 SM15 N-cyclopentyl-2-isopropylimidazo[1,2-a]pyridin-3-amine

¹H NMR (200 MHz, CDCl₃) δ 8.18-7.92 (m, 1H), 7.49 (m, 1H), 7.14-6.94 (m, 1H), 6.82-6.61 (m, 1H), 3.80-3.47 (m, 1H), 3.32-3.02 (m, 1H), 2.90-2.66 (m, 1H), 1.93-1.68 (m, 4H), 1.68-1.43 (m, 4H), 1.38 (d, J=9.0, 6H).
¹³C NMR (50 MHz, CDCl₃) δ 160.21, 155.76, 138.10, 126.18, 116.34, 105.78, 105.24, 58.19, 37.28, 37.04, 34.17, 25.09, 18.18, 17.96.
HRMS (ESI): m/z 244.1812 (M+H)⁺; calc. for C₁₅H₂₂N₃: 244.1814.

155 SM16 2-(3-chloro-2-fluorophenyl)-N-cyclopentylimidazo[1,2-a]pyridin-3-amine ¹H NMR (200 MHz, CDCl₃) δ 8.23 (d, 1H), 7.92-7.86 (m, 1H), 7.55 (d, 1H), 7.48-7.30 (d, 1H), 7.28-7.07 (m, 2H), 6.92-6.76 (m, 1H), 6.56-3.22 (m, 2H), 1.80-1.12 (m, 8H).

¹³C NMR (50 MHz, CDCl₃) δ 157.39, 152.48, 142.01, 138.19, 129.87, 129.62, 127.73, 124.93, 124.50, 124.08, 122.87, 117.52, 111.50, 59.58, 33.30, 23.31.

HRMS (ESI): m/z 330.1173 (M+H)⁺; calc. for $C_{18}H_{18}N_3FCl$: 330.1173.

156 SM17 N-cyclopentyl-2-(pentan-3-yl)imidazo[1,2-a]pyridin-3-amine

¹H NMR (200 MHz, CDCl₃) δ 8.06 (dt, J=1.0, 6.8, 1H), 7.49 (d, J=9.1, 1H), 7.04 (ddd, J=1.2, 6.6, 8.9, 1H), 6.71 (td, J=0.9, 6.8, 1H), 3.64 (dt, J=5.3, 10.8, 1H), 3.02-2.73 (m, 1H), 2.62 (ddd, J=6.4, 8.2, 14.6, 1H), 1.96-1.68 (m, 8H), 1.68-1.41 (m, 4H), 1.37 (d, J=6.8, 1H), 0.82 (t, J=7.4, 6H).

¹³C NMR (50 MHz, CDCl₃) δ 142.09, 141.51, 126.28, 122.65, 122.26, 116.94, 110.72, 60.03, 40.98, 33.58, 28.25, 23.65, 12.60.

HRMS (ESI): m/z 272.2125 (M+H)⁺; calc. for $C_{17}H_{26}N_3$: 272.2127.

157 SM18 N-cyclopentyl-2-(2-(trifluoromethyl)phenyl)imidazo[1,2-a]pyridin-3-amine ¹H NMR (200 MHz, CDCl₃) δ 8.13 (d, J=6.9, 1H), 7.78 (d, J=7.5, 1H), 7.66-7.41 (m, 4H), 7.23-7.03 (m, 1H), 6.81 (td, J=0.9, 6.7, 1H), 3.52-3.21 (m, 1H), 3.06-2.78 (m, 1H), 1.40 (m, 8H).

¹³C NMR (50 MHz, CDCl₃) δ 141.03, 135.34, 132.87, 131.23, 129.95, 128.14, 126.72, 126.17 (q, J=5.1), 123.60, 122.64, 121.42, 117.65, 111.59, 59.16, 33.33, 23.35.

HRMS (ESI): m/z 346.1531 (M+H)⁺; calc. for $C_{19}H_{19}N_3F_3$: 346.1531.

158 SM19 N-cyclopentyl-2-(3-methylthiophen-2-yl)imidazo[1,2-a]pyridin-3-amine ¹H NMR (200 MHz, CDCl₃) δ 8.15-8.06 (m, 1H), 7.52 (dt, J=1.0, 9.0, 1H), 7.26 (d, J=5.1, 1H), 7.11 (ddd, J=1.3, 6.7, 9.0, 1H), 6.94 (d, J=5.1, 1H), 6.77 (td, J=1.1, 6.8, 1H), 3.82-3.25 (m, 1H), 3.22-2.92 (m, 1H), 2.43 (s, 4H), 1.88-1.56 (m, 5H), 1.55-1.31 (m, 4H).

¹³C NMR (50 MHz, CDCl₃) δ 141.36, 135.77, 130.47, 129.73, 126.57, 124.33, 124.21, 123.50, 122.49, 117.47, 111.46, 59.35, 33.32, 23.50.

HRMS (ESI): m/z 298.1383 (M+H)⁺; calc. for $C_{17}H_{20}N_3S$: 298.1378.

159 SM20 N-cyclopentyl-2-cyclopropylimidazo[1,2-a]pyridin-3-amine

¹H NMR (200 MHz, CDCl₃) δ 8.01 (d, J=6.7, 1H), 7.40 (d, J=8.9, 1H), 7.21-6.91 (m, 1H), 6.91-6.47 (m, 1H), 3.85-3.53 (m, 1H), 3.14-2.48 (m, 1H), 2.21-1.69 (m, 4H), 1.69-1.40 (m, 4H), 1.23-0.79 (m, 5H).

¹³C NMR (50 MHz, CDCl₃) δ 141.47, 140.87, 138.47, 123.06, 122.12, 116.94, 111.17, 60.15, 33.82, 23.86, 8.45, 8.00.

HRMS (ESI): m/z 242.1659 (M+H)⁺; calc. for $C_{15}H_{20}N_3$: 242.1657.

160 SM21 2-sec-butyl-N-cyclopentylimidazo[1,2-a]pyridin-3-amine

¹H NMR (200 MHz, CDCl₃) δ 8.13-7.98 (m, 1H), 7.57-7.42 (m, 1H), 7.14-6.98 (m, 1H), 6.85-6.59 (m, 1H), 4.55-3.84 (m, 1H), 3.61 (m, 1H), 2.86 (m, 1H), 2.11-1.40 (m, 11H), 1.34 (d, J=6.9, 3H), 0.85 (t, J=7.4, 2H).

¹³C NMR (50 MHz, CDCl₃) δ 143.56, 141.42, 124.80, 122.89, 122.29, 116.86, 110.94, 59.92, 33.54, 33.51, 29.84, 23.58, 20.73, 12.61.

HRMS (ESI): m/z 258.1970 (M+H)⁺; calc. for $C_{16}H_{24}N_3$: 258.1970.

161 SM24 2-sec-butyl-N-cyclohexylimidazo[1,2-a]pyridin-3-amine

¹H NMR (200 MHz, CDCl₃) δ 8.14-7.93 (m, 1H), 7.48 (m, 1H), 7.04 (ddd, J=1.2, 6.7, 8.8, 1H), 6.71 (td, J=1.1, 6.9, 1H), 3.10-2.63 (m, 2H), 2.12-1.48 (m, 8H), 1.48-1.06 (m, 8H), 0.85 (t, J=7.3, 3H).

¹³C NMR (50 MHz, CDCl₃) δ 143.77, 141.75, 124.39, 123.01, 122.71, 117.13, 111.12, 57.58, 34.55, 33.63, 30.16, 26.09, 25.23, 21.07, 12.87.

HRMS (ESI): m/z 272.2127 (M+H)⁺; calc. for $C_{17}H_{26}N_3$: 272.2127.

162 SM26 6-bromo-2-(2-chlorophenyl)-N-cyclohexyl-7-methylimidazo[1,2-a]pyridin-3-amine ¹H NMR (200 MHz, CDCl₃) δ 8.30 (s, 1H), 7.71-7.54 (m, 1H), 7.52-7.12 (m, 4H), 3.22 (d, J=5.6, 1H), 2.78-2.51 (m, 1H), 2.45 (s, 3H), 1.87-1.33 (m, 5H), 1.23-0.78 (m, 5H).

¹³C NMR (50 MHz, CDCl₃) δ 140.87, 135.76, 134.14, 133.78, 132.60, 132.42, 129.45, 129.16, 126.86, 125.74, 122.98, 116.60, 110.69, 56.52, 33.79, 25.64, 24.56, 22.53.

HRMS (ESI): m/z 418.0686 (M+H)⁺; calc. for $C_{20}H_{22}N_3ClBr$: 418.0686.

163 SM27 2-(2-chlorophenyl)-N-cyclohexyl-6-methylimidazo[1,2-a]pyridin-3-amine ¹H NMR (200 MHz, CDCl₃) δ 7.91 (s, 1H), 7.74-7.54 (m, 1H), 7.52-7.40 (m, 2H), 7.40-7.18 (m, 2H), 6.98 (dd, J=1.7, 9.2, 1H), 3.40-3.07 (m, 1H), 2.82-2.51 (m, 1H), 2.35 (s, 3H), 1.91-1.31 (m, 5H), 1.23-0.80 (m, 5H).

¹³C NMR (50 MHz, CDCl₃) δ 140.71, 135.00, 134.20, 132.48, 129.31, 128.86, 126.74, 125.92, 121.02, 120.30, 116.84, 56.26, 33.80, 25.64, 24.55, 18.37.

HRMS (ESI): m/z 340.1582 (M+H)⁺; calc. for $C_{20}H_{23}N_3Cl$: 340.1581.

164 SM28 2-(2-chlorophenyl)-N-cyclohexyl-7-methylimidazo[1,2-a]pyridin-3-amine ¹H NMR (200 MHz, CDCl₃) δ 8.11 (d, 1H), 7.72-7.68 (m, 1H), 7.53-7.26 (m, 4H), 6.72 (dd, 1H), 3.24 (s, 1H), 2.78 (s, 1H), 2.45 (s, 3H), 1.80-1.42 (m, 5H), 1.23-0.97 (m, 5H).

¹³C NMR (50 MHz, CDCl₃) δ 142.4, 135.2, 134.4, 134.7, 133.9, 130.2, 129.3, 127.7, 126.2 123.3, 116.6, 115.3, 57.4, 34.7, 26.4, 25.2, 21.8.

HRMS (ESI): m/z 340.1581 (M+H)⁺; calc. for $C_{20}H_{23}N_3Cl$: 340.1581.

165 SM29 2-(2-chlorophenyl)-N-cyclohexyl-8-methylimidazo[1,2-a]pyridin-3-amine ¹H NMR (200 MHz, CDCl₃) δ 7.92 (s, 1H), 7.73-7.67 (m, 1H), 7.58-7.22 (m, 4H), 7.03-6.92 (dd, 1H), 3.37 (s, 1H), 2.72 (s, 1H), 2.38 (s, 3H), 1.85-1.42 (m, 5H), 1.22-1.08 (m, 5H).

¹³C NMR (50 MHz, CDCl₃) δ 146.1, 142.8, 141.3, 139.5, 135.9, 133.3, 130.2, 129.6, 127.2, 122.7, 121.3, 118.6, 57.0, 34.2, 26.5, 25.9, 19.5.

HRMS (ESI): m/z 340.1581 (M+H)$^+$; calc. for C$_{20}$H$_{23}$N$_3$Cl: 340.1581.

166 SM30 2-(2-chlorophenyl)-N-cyclohexyl-5-methylimidazo[1,2-a]pyridin-3-amine $^1$H NMR (200 MHz, CDCl$_3$) δ 7.71-7.68 (m, 1H), 7.52-7.26 (m, 4H), 7.12-7.08 (m, 1H), 6.53-6.46 (d, 1H), 3.25-3.18 (m, 1H), 3.03 (s, 3H), 2.65 (s, 1H), 1.80-1.45 (m, 5H), 1.26-0.81 (m, 5H).
$^{13}$C NMR (50 MHz, CDCl$_3$) δ 143.15, 137.29, 136.64, 134.56, 132.65, 132.48, 129.22, 128.87, 128.05, 126.71, 123.78, 115.74, 113.16, 58.72, 33.39, 25.67, 24.95, 19.84.
HRMS (ESI): m/z 340.1581 (M+H)$^+$; calc. for C$_{20}$H$_{23}$N$_3$Cl: 340.1581.

167 SM32 6-bromo-2-(2-chlorophenyl)-N-cyclopentyl-7-methylimidazo[1,2-a]pyridin-3-amine $^1$H NMR (200 MHz, CDCl$_3$) δ 8.31 (s, 1H), 7.65 (dd, J=2.5, 6.9, 1H), 7.53-7.11 (m, 4H), 3.50-3.25 (m, 1H), 3.24-3.07 (m, 1H), 2.44 (s, 3H), 1.77-1.04 (m, 8H).
$^{13}$C NMR (50 MHz, CDCl$_3$) δ 140.72, 135.51, 134.08, 133.66, 132.60, 132.36, 129.39, 129.15, 126.81, 126.38, 122.80, 116.51, 110.69, 59.33, 33.13, 23.20, 22.47.
HRMS (ESI): m/z 404.0528 (M+H)$^+$; calc. for C$_{19}$H$_{20}$N$_3$ClBr: 404.0529.

168 SM33 2-(2-chlorophenyl)-N-cyclopentyl-6-methylimidazo[1,2-a]pyridin-3-amine $^1$H NMR (200 MHz, CDCl$_3$) δ 7.98-7.90 (m, 1H), 7.67 (dd, J=2.2, 7.2, 1H), 7.52-7.38 (m, 2H), 7.38-7.28 (m, 2H), 7.00 (dd, J=1.8, 9.2, 1H), 3.49-2.94 (m, 2H), 2.36 (s, 3H), 1.73-0.94 (m, 8H).
$^{13}$C NMR (50 MHz, CDCl$_3$) δ 142.02, 135.00, 134.23, 132.63, 132.55, 129.39, 128.97, 126.87, 126.82, 121.16, 120.27, 116.94, 108.37, 59.32, 33.22, 23.28, 18.24
HRMS (ESI): m/z 326.1422 (M+H)$^+$; calc. for C$_{19}$H$_{21}$N$_3$Cl: 326.1424.

169 SM34 2-(2-chlorophenyl)-N-cyclopentyl-7-methylimidazo[1,2-a]pyridin-3-amine $^1$H NMR (200 MHz, CDCl$_3$) δ 8.05 (d, J=6.9, 1H), 7.75-7.60 (m, 1H), 7.46 (dd, J=2.1, 7.2, 1H), 7.41-7.16 (m, 3H), 6.64 (dd, J=1.5, 7.0, 1H), 3.49-3.01 (m, 2H), 2.40 (s, 3H), 1.72-1.10 (m, 8H).
$^{13}$C NMR (50 MHz, CDCl$_3$) δ 142.19, 138.27, 134.80, 134.49, 132.88, 132.79, 129.65, 129.28, 129.20, 127.06, 122.22, 116.13, 114.50, 59.76, 33.45, 23.54, 21.56.
HRMS (ESI): m/z 326.1422 (M+H)$^+$; calc. for C$_{19}$H$_{21}$N$_3$Cl: 326.1424.

170 SM35 2-(2-chlorophenyl)-N-cyclopentyl-8-methylimidazo[1,2-a]pyridin-3-amine $^1$H NMR (200 MHz, CDCl$_3$) δ 8.03 (ddd, J=0.5, 1.0, 2.4, 1H), 7.74-7.64 (m, 1H), 7.50-7.42 (m, 1H), 7.41-7.26 (m, 2H), 6.94 (d, J=6.7, 1H), 6.72 (t, J=6.7, 1H), 3.47-3.25 (m, 1H), 3.26-3.00 (m, 1H), 2.62 (s, 3H), 1.71-1.41 (m, 6H), 1.41-1.01 (m, 3H).
$^{13}$C NMR (50 MHz, CDCl$_3$) δ 141.93, 138.20, 134.64, 134.32, 132.84, 132.75, 129.35, 129.00, 127.31, 126.90, 122.49, 120.58, 111.62, 59.43, 33.26, 23.29, 16.71.
HRMS (ESI): m/z 326.1424 (M+H)$^+$; calc. for C$_{19}$H$_{21}$N$_3$Cl: 326.1424.

171 SM36 2-(2-chlorophenyl)-N-cyclopentyl-5-methylimidazo[1,2-a]pyridin-3-amine $^1$H NMR (200 MHz, CDCl$_3$) δ 7.76-7.61 (m, 1H), 7.56-7.21 (m, 4H), 7.01 (dd, J=6.9, 8.9, 1H), 6.49 (d, J=8.6, 1H), 3.37-3.00 (m, 2H), 2.97 (s, 3H), 1.71-1.28 (m, 6H), 1.28-0.93 (m, 2H).
$^{13}$C NMR (50 MHz, CDCl$_3$) δ 143.47, 138.45, 137.04, 134.89, 133.05, 132.97, 132.86, 129.60, 129.29, 127.11, 124.22, 116.12, 113.55, 62.36, 32.95, 23.56, 20.16.
HRMS (ESI): m/z 326.1426 (M+H)$^+$; calc. for C$_{19}$H$_{21}$N$_3$Cl: 326.1424.

172 SM38 6-bromo-N-cyclopentyl-2-isopropyl-7-methylimidazo[1,2-a]pyridin-3-amine $^1$H NMR (200 MHz, CDCl$_3$) δ 8.18 (s, 1H), 7.33 (s, 1H), 3.69-3.44 (m, 1H), 3.27-2.96 (m, 1H), 2.88-2.53 (m, 1H), 2.41 (s, 3H), 1.97-1.38 (m, 8H), 1.34 (d, J=6.8, 6H).
$^{13}$C NMR (50 MHz, CDCl$_3$) δ 145.57, 133.02, 123.33, 122.61, 116.30, 109.91, 109.74, 59.91, 33.56, 26.32, 23.61, 22.73, 22.44.
HRMS (ESI): m/z 336.1077 (M+H)$^+$; calc. for C$_{16}$H$_{23}$N$_3$Br: 336.1075.

173 SM39 N-cyclopentyl-2-isopropyl-6-methylimidazo[1,2-a]pyridin-3-amine $^1$H NMR (200 MHz, CDCl$_3$) δ 7.86-7.74 (m, 1H), 7.39 (d, J=9.1, 1H), 6.90 (dd, J=1.8, 9.1, 1H), 3.71-3.41 (m, 1H), 3.29-3.00 (m, 1H), 2.31 (s, 3H), 1.91-1.41 (m, 8H), 1.36 (d, J=6.9, 6H).
$^{13}$C NMR (50 MHz, CDCl$_3$) δ 144.70, 140.54, 125.88, 123.17, 120.44, 120.04, 116.42, 59.75, 33.55, 26.23, 23.64, 22.85, 18.37.
HRMS (ESI): m/z 258.1972 (M+H)$^+$; calc. for C$_{16}$H$_{24}$N$_3$: 258.1970.

174 SM40 N-cyclopentyl-2-isopropyl-7-methylimidazo[1,2-a]pyridin-3-amine $^1$H NMR (200 MHz, CDCl$_3$) δ 7.91 (d, J=7.1, 1H), 7.24 (s, 1H), 6.54 (dd, J=1.4, 7.1, 1H), 3.68-3.46 (m, 1H), 3.24-2.99 (m, 1H), 2.35 (s, 3H), 1.90-1.40 (m, 8H), 1.36 (d, J=6.9, 6H).
$^{13}$C NMR (50 MHz, CDCl$_3$) δ 144.35, 141.78, 133.46, 121.96, 121.53, 115.42, 113.42, 59.85, 33.41, 26.15, 23.52, 22.71, 21.09.
HRMS (ESI): m/z 258.1969 (M+H)$^+$; calc. for C$_{16}$H$_{24}$N$_3$: 258.1970.

175 SM41 N-cyclopentyl-2-isopropyl-8-methylimidazo[1,2-a]pyridin-3-amine $^1$H NMR (200 MHz, CDCl$_3$) δ 8.00-7.82 (m, 1H), 6.97-6.75 (m, 1H), 6.62 (t, J=6.8, 1H), 3.72-3.43 (m, 1H), 3.33-2.99 (m, 1H), 2.58 (s, 3H), 1.93-1.67 (m, 4H), 1.67-1.43 (m, 4H), 1.39 (d, J=6.9, 6H).
$^{13}$C NMR (50 MHz, CDCl$_3$) δ 144.27, 141.65, 126.67, 124.17, 121.68, 120.23, 110.86, 59.99, 33.59, 26.71, 23.65, 22.82, 16.87.
HRMS (ESI): m/z 258.1969 (M+H)$^+$; calc. for C$_{16}$H$_{24}$N$_3$: 258.1970.

176 SM42 N-cyclopentyl-2-isopropyl-5-methylimidazo[1,2-a]pyridin-3-amine $^1$H NMR (200 MHz, CDCl$_3$) δ 7.35 (d, J=8.9, 1H), 6.91 (dd, J=6.8, 9.0, 1H), 6.39-6.30 (m, 1H), 3.63-3.38 (m, 1H), 3.15 (q, J=6.8, 1H), 2.96-2.76 (m, 3H), 1.93-1.67 (m, 4H), 1.67-1.41 (m, 4H), 1.41-1.26 (m, 6H).

$^{13}$C NMR (50 MHz, CDCl$_3$) δ 146.39, 143.09, 135.91, 123.02, 115.29, 115.29, 112.63, 62.55, 32.91, 25.88, 23.65, 22.75, 19.68.

HRMS (ESI): m/z 258.1971 (M+H)$^+$; calc. for C$_{16}$H$_{24}$N$_3$: 258.1970.

177 SM44 6-bromo-N-cyclohexyl-2-isopropyl-7-methylimidazo[1,2-a]pyridin-3-amine $^1$H NMR (200 MHz, CDCl$_3$) δ 8.17 (s, 1H), 7.33 (s, 1H), 3.08 (q, J=6.7, 1H), 2.96-2.59 (m, 2H), 2.41 (s, 3H), 2.02-1.46 (m, 6H), 1.34 (d, J=6.9, 6H), 1.29-1.07 (m, 4H).

$^{13}$C NMR (50 MHz, CDCl$_3$) δ 145.76, 138.45, 133.21, 122.96, 116.48, 110.14, 100.21, 57.62, 34.47, 26.54, 26.07, 25.16, 22.97, 22.68.

HRMS (ESI): m/z 350.1236 (M+H)$^+$; calc. for C$_{17}$H$_{25}$N$_3$Br: 350.1232.

178 SM45 N-cyclohexyl-2-isopropyl-6-methylimidazo[1,2-a]pyridin-3-amine $^1$H NMR (200 MHz, CDCl$_3$) δ 7.78 (s, 1H), 7.38 (d, J=9.2, 1H), 6.89 (dd, J=1.7, 9.1, 1H), 3.23-3.00 (m, 1H), 2.97-2.74 (m, 1H), 2.31 (s, 3H), 1.98-1.47 (m, 5H), 1.35 (d, J=6.9, 6H), 1.22-1.09 (m, 5H).

$^{13}$C NMR (50 MHz, CDCl$_3$) δ 144.63, 140.56, 138.22, 125.82, 120.41, 120.14, 116.41, 57.17, 34.30, 26.22, 25.89, 24.98, 22.86, 18.39.

HRMS (ESI): m/z 272.2126 (M+H)$^+$; calc. for C$_{17}$H$_{26}$N$_3$: 272.2127.

179 SM46 N-cyclohexyl-2-isopropyl-7-methylimidazo[1,2-a]pyridin-3-amine $^1$H NMR (200 MHz, CDCl$_3$) δ 8.00-7.79 (m, 1H), 7.26 (s, 1H), 6.55 (dd, J=1.5, 7.0, 1H), 3.23-2.93 (m, 2H), 2.93-2.73 (m, 1H), 2.35 (s, 3H), 1.99-1.44 (m, 5H), 1.35 (d, J=6.9, 6H), 1.30-0.99 (m, 5H).

$^{13}$C NMR (50 MHz, CDCl$_3$) δ 144.44, 142.08, 139.90, 133.86, 122.00, 115.73, 113.81, 57.62, 34.51, 26.47, 26.14, 25.20, 23.03, 21.47.

HRMS (ESI): m/z 272.2126 (M+H)$^+$; calc. for C$_{17}$H$_{26}$N$_3$: 272.2127.

180 SM47 N-cyclohexyl-2-isopropyl-8-methylimidazo[1,2-a]pyridin-3-amine $^1$H NMR (200 MHz, CDCl$_3$) δ 7.89 (d, J=6.8, 1H), 7.02-6.73 (m, 1H), 6.61 (t, J=6.7, 1H), 3.28-3.04 (m, 1H), 2.98-2.66 (m, 2H), 2.57 (s, 3H), 1.97-1.50 (m, 5H), 1.38 (d, J=6.9, 6H), 1.31-1.04 (m, 5H).

$^{13}$C NMR (50 MHz, CDCl$_3$) δ 153.93, 144.41, 141.95, 126.89, 121.84, 120.62, 111.05, 57.61, 34.57, 26.94, 26.14, 25.24, 23.08, 17.13.

HRMS (ESI): m/z 272.2123 (M+H)$^+$; calc. for C$_{17}$H$_{26}$N$_3$: 272.2127.

181 SM48 N-cyclohexyl-2-isopropyl-5-methylimidazo[1,2-a]pyridin-3-amine $^1$H NMR (200 MHz, CDCl$_3$) δ 7.36 (d, J=8.8, 1H), 6.92 (dd, J=6.7, 8.9, 1H), 6.42-6.29 (m, 1H), 3.24-3.00 (m, 1H), 2.89 (s, 3H), 1.97-1.51 (m, 5H), 1.35 (d, J=6.9, 6H), 1.31-0.97 (m, 5H).

$^{13}$C NMR (50 MHz, CDCl$_3$) δ 144.26, 141.87; 139.92, 138.47, 123.30, 115.64, 112.96, 59.90, 33.82, 26.27, 26.23, 25.46, 23.01, 20.09.

HRMS (ESI): m/z 272.2128 (M+H)$^+$; calc. for C$_{17}$H$_{26}$N$_3$: 272.2127.

182 SM81 N,2-bis(2-chlorophenyl)-5-methylimidazo[1,2-a]pyridin-3-amine $^1$H NMR (200 MHz, CDCl$_3$) δ 7.68-7.49 (m, 2H), 7.49-7.34 (m, 1H), 7.34-7.20 (m, 2H), 7.14 (dd, J=6.8, 9.1, 1H), 7.03-6.84 (m, 1H), 6.65 (td, J=1.2, 7.6, 1H), 6.52 (d, J=6.7, 1H), 6.19 (s, 1H), 6.09 (dd, J=1.1, 8.3, 1H), 2.67 (s, 3H).

$^{13}$C NMR (50 MHz, CDCl$_3$) δ 144.65, 143.60, 140.64, 138.21, 136.14, 133.24, 132.70, 131.97, 129.61, 129.48, 129.38, 127.82, 126.70, 125.31, 119.47, 118.64, 116.22, 113.90, 113.60, 18.59.

HRMS (ESI): m/z 368.0733 (M+H)$^+$; calc. for C$_{20}$H$_{16}$N$_3$Cl$_2$: 368.0721.

183 SM83 2-(2-chlorophenyl)-N-cyclohexyl-5,7-dimethylimidazo[1,2-a]pyridin-3-amine $^1$H NMR (200 MHz, CDCl$_3$) δ 7.71-7.53 (m, 1H), 7.52-7.39 (m, 1H), 7.39-7.20 (m, 2H), 7.14 (s, 1H), 6.29 (s, 1H), 2.91 (s, 3H), 2.54 (m, 1H), 2.31 (s, 3H), 1.58 (m, 5H), 1.11-0.68 (m, 5H).

$^{13}$C NMR (50 MHz, CDCl$_3$) δ 143.77, 138.20, 135.88, 134.77, 134.58, 132.74, 132.57, 129.31, 128.86, 127.69, 126.79, 116.02, 114.18, 58.77, 33.16, 25.80, 24.76, 20.87, 19.72.

HRMS (ESI): m/z 354.1715 (M+H)$^+$; calc. for C$_{21}$H$_{25}$N$_3$Cl: 354.1737.

184 SM92 2-(2-chlorophenyl)-N-cyclohexyl-5-phenoxyimidazo[1,2-a]pyridin-3-amine $^1$H NMR (200 MHz, CDCl$_3$) δ 7.68-7.61 (m, 1H), 7.56-7.41 (m, 3H), 7.39-7.28 (m, 3H), 7.28-7.19 (m, 3H), 7.08-6.89 (m, 1H), 5.91 (d, J=7.2, 1H), 2.89-2.80 (m, 1H), 1.78-1.41 (m, 6H), 1.11-0.81 (m, 5H).

$^{13}$C NMR (50 MHz, CDCl$_3$) δ 156.34, 149.94, 143.46, 138.28, 134.05, 133.85, 131.01, 129.96, 129.24, 128.01, 127.34, 124.91, 120.04, 113.84, 97.02, 57.96, 33.95, 25.74, 25.07.

HRMS (ESI): m/z 418.1635 (M+H)$^+$; calc. for C$_{25}$H$_{25}$N$_3$OCl: 418.1686.

185 SM93 2-(2-chlorophenyl)-N-cyclohexyl-5-ethoxyimidazo[1,2-a]pyridin-3-amine $^1$H NMR (200 MHz, CDCl$_3$) δ 7.57 (dd, J=3.3, 6.0, 1H), 7.51-7.39 (m, 1H), 7.38-7.19 (m, 2H), 7.13 (d, J=8.9, 1H), 7.04-6.88 (m, 1H), 5.89 (d, J=7.3, 1H), 4.26 (q, J=7.0, 2H), 4.11 (s, 1H), 2.74 (s, 1H), 1.83-1.63 (m, 2H), 1.63-1.31 (m, 6H), 1.21-0.75 (m, 5H).

$^{13}$C NMR (50 MHz, CDCl$_3$) δ 150.94, 142.66, 134.48, 134.05, 132.58, 129.41, 128.73, 128.48, 126.29, 123.89, 110.70, 88.54, 65.45, 57.15, 33.42, 25.88, 24.57, 14.46.

HRMS (ESI): m/z 370.1658 (M+H)$^+$; calc. for C$_{21}$H$_{25}$N$_3$OCl: 370.1686.

186 DG402-49720 4-(3-(cyclohexylamino)imidazo[1,2-a]pyridin-2-yl)benzonitrile $^1$H NMR (400 MHz, CDCl$_3$) δ 8.24 (dd, J=1.7, 8.5, 2H), 8.05 (dt, J=1.0, 6.9, 1H), 7.69 (dd, J=1.7, 8.5, 2H), 7.53 (dt, J=1.0, 9.1, 1H), 7.17 (ddd, J=1.2, 6.7, 9.1, 1H), 6.81 (td, J=1.0, 6.8, 1H), 3.06 (d, J=4.9, 1H), 2.95 (ddd, J=4.6, 10.0, 14.4, 1H), 1.87-1.76 (m, 2H), 1.76-1.64 (m, 2H), 1.64-1.51 (m, 1H), 1.33-1.03 (m, 5H).

$^{13}$C NMR (101 MHz, CDCl$_3$) δ 141.94, 139.17, 134.70, 132.16, 127.17, 126.06, 124.61, 122.63, 119.18, 117.75, 112.04, 110.20, 56.96, 34.22, 25.59, 24.77.

HRMS (ESI): m/z 317.1765 (M+H)$^+$; calc. for C$_{20}$H$_{21}$N$_4$: 317.1766.

187 DG402-49722 3-(3-(cyclohexylamino)imidazo[1,2-a]pyridin-2-yl)benzonitrile $^1$H NMR (400 MHz, CDCl$_3$) δ 8.48 (t, J=1.6, 1H), 8.37 (dt, J=1.5, 7.6, 1H), 8.14-7.94 (m, 1H), 7.62-7.45 (m, 3H), 7.16 (ddd, J=1.1, 6.7, 9.0, 1H), 6.81 (td, J=1.0, 6.8, 1H), 3.04 (d, J=4.7, 1H), 2.94 (ddd, J=4.4, 10.0, 14.3, 1H), 1.88-1.75 (m, 2H), 1.75-1.63 (m, 2H), 1.63-1.49 (m, 1H), 1.42-0.92 (m, 5H).

$^{13}$C NMR (101 MHz, CDCl$_3$) δ 141.85, 135.91, 134.59, 130.95, 130.44, 130.33, 129.11, 125.29, 124.46, 122.58, 118.98, 117.64, 112.48, 111.96, 56.91, 34.21, 25.58, 24.76.

HRMS (ESI): m/z 317.1775 (M+H)$^+$; calc. for C$_{20}$H$_{21}$N$_4$: 317.1766.

188 DG402-49744 7-chloro-2-(2-chlorophenyl)-N-cyclohexylimidazo[1,2-a]pyridin-3-amine $^1$H NMR (400 MHz, CDCl$_3$) δ 8.07 (d, J=7.3, 1H), 7.64 (d, J=5.5, 1H), 7.52 (s, 1H), 7.47 (d, J=6.3, 1H), 7.35 (dd, J=7.1, 12.4, 2H), 6.79 (d, J=7.2, 1H), 3.26 (s, 1H), 2.64 (s, 1H), 1.75-1.61 (m, 2H), 1.56 (s, 2H), 1.47 (s, 1H), 1.15-0.91 (m, 5H).

$^{13}$C NMR (101 MHz, CDCl$_3$) δ 141.08, 135.68, 133.40, 132.41, 132.35, 130.20, 129.44, 129.28, 126.93, 126.56, 123.19, 116.16, 113.23, 56.41, 33.71, 25.49, 24.46.

189 CW23828a 2-(2-chlorophenyl)-N-cyclohexyl-6-(4-methoxyphenyl)imidazo[1,2-a]pyridin-3-amine $^1$H NMR (400 MHz, CDCl$_3$) δ 8.25 (s, 1H), 7.70 (dd, J=1.9, 7.5, 1H), 7.60 (dd, J=0.7, 9.3, 1H), 7.54 (d, J=8.8, 2H), 7.48 (dd, J=1.5, 7.7, 1H), 7.43-7.29 (m, 3H), 7.03 (d, J=8.8, 2H), 3.86 (s, 3H), 3.31 (d, J=6.8, 1H), 2.80-2.59 (m, 1H), 1.78-1.63 (m, 2H), 1.63-1.51 (m, 2H), 1.51-1.40 (m, 1H), 1.17-0.89 (m, 5H).

$^{13}$C NMR (101 MHz, CDCl$_3$) δ 159.32, 140.83, 135.58, 133.97, 132.48, 130.28, 129.41, 129.07, 127.99, 126.88, 126.56, 125.70, 124.48, 119.32, 117.26, 114.43, 56.42, 55.32, 33.79, 25.55, 24.53.

190 CW23828b 2-(2-chlorophenyl)-N-cyclohexyl-5-(4-methoxyphenyl)imidazo[1,2-a]pyridin-3-amine $^1$H NMR (400 MHz, CDCl$_3$) δ 7.62 (dd, J=2.1, 7.3, 1H), 7.60-7.53 (m, 1H), 7.46 (d+m, J=8.7, 3H), 7.37-7.26 (m, 2H), 7.14 (dd, J=6.8, 8.9, 1H), 6.98 (d, J=8.6, 2H), 6.61 (dd, J=1.0, 6.8, 1H), 3.88 (s, 3H), 2.64 (s, 1H), 2.00 (m, 1H), 0.82 (m, 8H), 0.37 (m, 2H).

$^{13}$C NMR (101 MHz, CDCl$_3$) δ 159.88, 142.70, 138.01, 135.45, 134.19, 133.32, 132.69, 130.78, 129.40, 128.92, 127.99, 127.08, 126.62, 122.99, 116.73, 115.26, 112.64, 56.36, 55.50, 32.47, 25.59, 24.34.

191 CW23825 2-(2-chlorophenyl)-N-cyclohexyl-5-o-tolylimidazo[1,2-a]pyridin-3-amine

192 CW23828c 2-(2-chlorophenyl)-N-cyclohexyl-6-o-tolylimidazo[1,2-a]pyridin-3-amine $^1$H NMR (400 MHz, CDCl$_3$) δ 7.65-7.60 (m, 1H), 7.58 (dd, J=1.2, 9.0, 1H), 7.46-7.19 (m, 7H), 7.15 (dd, J=6.8, 9.0, 1H), 6.57 (dd, J=1.2, 6.8, 1H), 2.45 (d, J=7.8, 1H), 2.07 (s, 3H), 2.01 (ddd, J=3.6, 8.5, 10.1, 1H), 1.41-0.98 (m, 5H), 0.89-0.65 (m, 2H), 0.58 (d, J=12.4, 1H), 0.41-0.27 (m, 1H), 0.27-0.11 (m, 1H).

$^{13}$C NMR (101 MHz, CDCl$_3$) δ 142.26, 138.77, 137.87, 134.92, 134.19, 133.22, 132.68, 129.34, 129.24, 129.00, 128.97, 128.94, 128.53, 127.75, 127.34, 126.66, 125.06, 122.97, 116.94, 114.82, 56.76, 32.63, 32.50, 25.55, 19.77.

193 DG402-49750 2-(2-chlorophenyl)-N-cyclohexylimidazo[1,2-a]pyrimidin-3-amine $^1$H NMR (400 MHz, CDCl$_3$) δ 8.53 (dd, J=2.1, 4.1, 1H), 8.46 (dd, J=2.1, 6.8, 1H), 7.81-7.70 (m, 1H), 7.55-7.43 (m, 1H), 7.38 (dqd, J=1.8, 7.4, 14.8, 2H), 6.90 (dd, J=4.1, 6.8, 1H) 3.34 (d, J=6.9, 1H), 2.64 (dd, J=3.4, 6.7, 1H), 1.73-1.61 (m, 2H), 1.61-1.52 (m, 2H), 1.47 (s, 1H), 1.19-0.91 (m, 5H).

$^{13}$C NMR (101 MHz, CDCl$_3$) δ 149.13, 144.56, 136.60, 133.27, 132.79, 132.24, 130.42, 129.45, 129.42, 127.01, 124.75, 108.09, 56.60, 33.72, 25.47, 24.46.

HRMS (ESI): m/z 327.1380 (M+H)$^+$; calc. for C$_{18}$H$_{20}$N$_4$Cl: 327.1376.

194 DG 402-49752 2-(2-chlorophenyl)-N-cyclohexylimidazo[2,1-a]isoquinolin-3-amine $^1$H NMR (400 MHz, CDCl$_3$) δ 8.66 (d, J=8.0, 1H), 8.00 (d, J=7.3, 1H), 7.75 (dd, J=1.6, 7.5, 1H), 7.71 (d, J=7.0, 1H), 7.62-7.57 (m, 1H), 7.57-7.51 (m, 1H), 7.48 (dd, J=1.2, 7.9, 1H), 7.39 (td, J=1.4, 7.5, 1H), 7.36-7.30 (m, 1H), 7.07 (d, J=7.2, 1H), 3.29 (d, J=7.1, 1H), 2.78-2.62 (m, 1H), 1.77-1.66 (m, 2H), 1.63-1.51 (m, 2H), 1.51-1.44 (m, 1H), 1.16-0.98 (m, 5H).

$^{13}$C NMR (101 MHz, CDCl$_3$) δ 139.07, 134.03, 132.69, 132.61, 129.61, 129.43, 129.38, 128.97, 128.12, 127.88, 127.78, 127.05, 126.89, 123.95, 122.72, 120.44, 112.30, 56.93, 33.80, 25.62, 24.60.

HRMS (ESI): m/z 376.1587 (M+H)$^+$; calc. for C$_{23}$H$_{23}$N$_3$Cl: 376.1581.

Biological Activity

Table 1 gives selected results for the compounds of the invention against HIV-1 reverse transcriptase in an enzymatic assay and/or whole cell anti-HIV assay.

TABLE 1
IC$_{50}$ values obtained for compounds against HIV-1 reverse transcriptase enzymatic assay and whole cell anti-HIV assay.
| Compound | Enzymatic Assay IC$_{50}$ (μM) | % enzyme activity at 50 μM inhibitor concentration | Whole cell MAGI anti-HIV IC$_{50}$ (μM) |
| --- | --- | --- | --- |
| 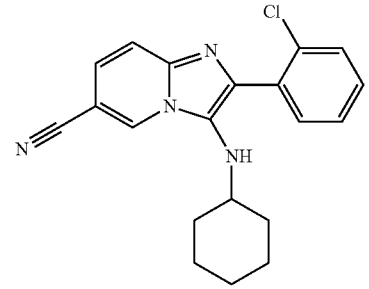 96 | 6.60 | 11.8 | 0.63 (MAGI) |
| 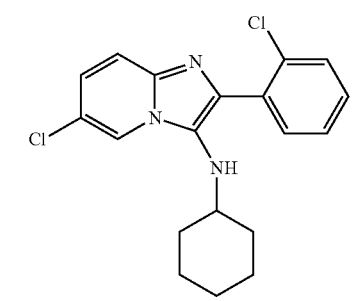 82 | 14.47 | 20 | 0.84 (MAGI) |
| 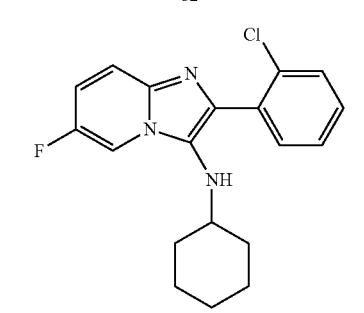 81 | 11.28 | 17 | 1.88 (MAGI) |
| 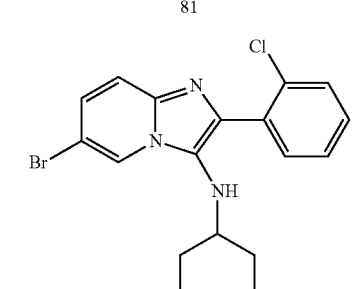 99 | 12.20 | 20 | 2.19 (MAGI) |
| 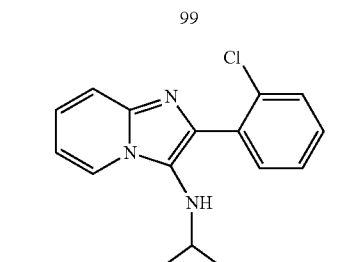 | 18.1 | | 2.19 (MAGI) |

Enzymatic Method for Determining Activity Against Reverse Transcriptase

The assay is based on a sandwich-ELISA protocol employing the ROCHE colorimetric reverse transcriptase kit (cat#11468120910). Biotin and DIG-labelled nucleotides are incorporated into cDNA strands polymerized on an RNA template by the action of HIV-1 reverse transcriptase. The cDNA products are bound to streptavidin-coated wells of 96-well plate inserts, and their associated DIG-moieties detected by incubation with anti-DIG antibodies conjugated to horseradish peroxidase (HRP). The amount of bound antibody is quantitated by incubation with a colorimetric HRP substrate, followed by absorbance reading at 405 nm using a multiwell spectrophotometer.

To assess the inhibitory activity of test compounds, a single concentration screen (usually 50 µM) or $IC_{50}$ determination may be carried out. In the single concentration screen, compounds are incubated with HIV-1 reverse trancriptase and substrate and the residual enzyme activity expressed as a percentage relative to a control without inhibitor. For $IC_{50}$ determinations, 4-fold serial dilutions of the compounds are incubated with HIV-1 reverse trancriptase and substrate and the enzyme activity, expressed as a percentage relative to a control without inhibitor, plotted against inhibitor concentration to derive the concentration at which 50% enzyme inhibition ($IC_{50}$) is obtained.

Cellular Methods for Determining Anti-HIV Activity
PBMC

Fresh human PBMCs, seronegative for HIV and HBV, were isolated from screened donors (Interstate Blood Bank, Inc. Memphis, Tenn.). Cells were pelleted/washed 2-3 times by low speed centrifugation and re-suspension in PBS to remove contaminating platelets. The Leukophoresed blood was then diluted 1:1 with Dulbecco's Phosphate Buffered Saline (DPBS) and layered over 14 mL of Lymphocyte Separation Medium (LSM; Cellgro® by Mediatech, Inc.; density 1.078+/−0.002 g/ml; Cat.#85-072-CL) in a 50 mL centrifuge tube and then centrifuged for 30 minutes at 600×g. Banded PBMCs were gently aspirated from the resulting interface and subsequently washed 2× with PBS by low speed centrifugation. After the final wash, cells were enumerated by trypan blue exclusion and re-suspended at $1 \times 10^7$ cells/ml in RPMI 1640 supplemented with 15% Fetal Bovine Serum (FBS), and 2 mM L-glutamine, 4 µg/ml Phytohemagglutinin (PHA-P, Sigma). The cells were allowed to incubate for 48-72 hours at 37° C. After incubation, PBMCs were centrifuged and resuspended in RPMI 1640 with 15% FBS, 2 mM L-glutamine, 100 U/ml penicillin, 100 µg/ml streptomycin, 10 µg/ml gentamycin, and 20 U/ml recombinant human IL-2 (R&D Systems, Inc). IL-2 is included in the culture medium to maintain the cell division initiated by the PHA mitogenic stimulation. PBMCs were maintained in this medium at a concentration of $1-2 \times 10^6$ cells/mL with biweekly medium changes until used in the assay protocol. Cells were kept in culture for a maximum of two weeks before being deemed too old for use in assays and discarded. Monocytes were depleted from the culture as the result of adherence to the tissue culture flask.

For the standard PBMC assay, PHA-P stimulated cells from at least two normal donors were pooled (mixed together), diluted in fresh medium to a final concentration of $1 \times 10^6$ cells/mL, and plated in the interior wells of a 96 well round bottom microplate at 50 µl/well ($5 \times 10^4$ cells/well) in a standard format developed by the Infectious Disease Research department of Southern Research Institute. Pooling (mixing) of mononuclear cells from more than one donor is used to minimize the variability observed between individual donors, which results from quantitative and qualitative differences in HIV infection and overall response to the PHA and IL-2 of primary lymphocyte populations. Each plate contains virus/cell control wells (cells plus virus), experimental wells (drug plus cells plus virus) and compound control wells (drug plus media without cells, necessary for MTS monitoring of cytotoxicity). Since HIV-1 is not cytopathic to PBMCs, this allows the use of the same assay plate for both antiviral activity and cytotoxicity measurements. Test drug dilutions were prepared at a 2× concentration in microtiter tubes and 100 µl of each concentration was placed in appropriate wells using the standard format. 50 µl of a predetermined dilution of virus stock was placed in each test well (final MOI≈0.1). The PBMC cultures were maintained for seven days following infection at 37° C., 5% $CO_2$. After this period, cell-free supernatant samples were collected for analysis of reverse transcriptase activity. Following removal of supernatant samples, compound cytotoxicity was measured by addition of MTS to the plates for determination of cell viability. Wells were also examined microscopically and any abnormalities were noted.

MAGI

MAGI-R5 cells naturally express the CXCR4 co-receptor and are engineered to express CD4 (HIV-1 cell surface receptor), the CCR5 co-receptor and also to contain an LTR-β-galactosidase reporter construct. The MAGI Antiviral Assay is designed to identify compounds that block HIV-1 replication via targets in the viral life cycle up to and including Tat transactivation (e.g. virus attachment/fusion/entry, uncoating, reverse transcription, nuclear import, integration, LTR transactivation). MAGI cells are treated with compound for 15 to 30 min prior to addition of virus. HIV-1 is then added to the cells/compounds and the cultures are incubated for 48 hours. If the virus is able to infect the cells it will proceed through reverse transcription and integration and begin transcription from the integrated provirus. One of the first virus proteins produced is HIV 1 Tat, which transactivates the HIV-1 LTR promoter driving expression of β-galactosidase. As a result, infected cells begin to overproduce the β-galactosidase enzyme. Forty-eight hours post infection, the cells are lysed and β-galactosidase enzyme activity is measured using a chemiluminescence detection method (Perkin Elmer Applied Biosystems). Compound toxicity is monitored on replicate plates using MTS dye reduction (CellTiter 96® Reagent, Promega, Madison, Wis.).

The invention accordingly shows that compounds of the general structure A and B inhibit the enzyme HIV-1 reverse transcriptase and thus have application as anti-HIV agents.

PCT/US2008/082531 claims the priority of U.S. Ser. No. 60/986,990. However, at the time of filing this application, the priority document was not available from the US Patent Office. If the priority date of any compounds disclosed in PCT/US2008/082531 is later than the priority date of the compounds disclosed in this specification it will be necessary to amend the provisos. The following has therefore been included in this specification to provide for this eventuality.

The invention also provides the use of a compound selected from compounds of the formula A and B in the manufacture of a medicament for the treatment of a subject infected with HIV, a composition for use in treating a subject who has been infected with HIV, the composition including a compound selected from compounds of formula A or B, for use in the treatment of a subject suffering from an HIV infection, a method of treating a subject suffering from an HIV infection by administration of a compound selected from compounds of formula A or B and compounds of formula A or B in which, for formula A
R is selected from alkyl, branched alkyl, cycloalkyl, aryl, substituted aryl, naphthyl, benzyl and bicycloalkyl, R¹ is selected from alkyl, cycloalkyl, substituted alkyl, branched alkyl, phenyl, heteroaryl, oxacycloalkyl, bicycloalkyl, furyl, substituted furyl, thienyl and substituted thienyl R²-R⁵ are independently selected from H, halogen, cyano, alkyl and substituted alkyl, or R² and R³ together form a carbocyclic ring or, independently, R⁴ and R⁵ together form a carbocyclic ring, R⁶ is H, alkyl or alkanoyl, and in which for formula B, R is cycloalkyl and R¹ is substituted aryl provided that compounds disclosed in U.S. Ser. No. 60/986,990 are excluded.

The invention claimed is:

1. A compound which is selected from the group consisting of

N-cyclohexyl-2-cyclopropylimidazo[1,2-a]pyridin-3-amine;
N-cyclohexyl-2-(2-(methylthio)ethyl)imidazo[1,2-a]pyridin-3-amine;
2-sec-butyl-N-cyclohexylimidazo[1,2-a]pyridin-3-amine;
N-cyclohexyl-2-(5-methylisoxazol-3-yl)imidazo[1,2-a]pyridin-3-amine;
N-butyl-2-isopropylimidazo[1,2-a]pyridin-3-amine;
2-(2-chlorophenyl)-N-cyclohexylimidazo[1,2-a]pyridin-3-amine;
2-isopropyl-N-pentylimidazo[1,2-a]pyridin-3-amine;
4-(3-(cyclohexylamino)imidazo[1,2-a]pyridin-2-yl)-2-ethoxyphenol;
2-cyclopropyl-5,7-dimethyl-N-(naphthalen-2-yl)imidazo[1,2-a]pyridin-3-amine;
N-cyclohexyl-5,7-dimethyl-2-propylimidazo[1,2-a]pyridin-3-amine;
N,2-bis(4-methoxyphenyl)imidazo[1,2-a]pyridin-3-amine;
N-cyclohexyl-2-cyclopentylimidazo[1,2-a]pyridin-3-amine;
2-isopropyl-N-(naphthalen-2-yl)imidazo[1,2-a]pyridin-3-amine;
N-cyclohexyl-2-(2,5-dimethoxytetrahydrofuran-3-yl)imidazo[1,2-a]pyridin-3-amine;
N-cyclohexyl-6-fluoro-2-isopropylimidazo[1,2-a]pyridin-3-amine;
N-cyclohexyl-2-isopropyl-5,7-dimethylimidazo[1,2-a]pyridin-3-amine;
2-cyclopropyl-N-pentylimidazo[1,2-a]pyridin-3-amine;
2-(4-methoxyphenyl)-N-(naphthalen-2-yl)imidazo[1,2-a]pyridin-3-amine;
N-cyclohexyl-2-((1R,5S)-6,6-dimethylbicyclo[3.1.1]hept-2-en-2-yl)imidazo[1,2-a]pyridin-3-amine;
N-butyl-2-cyclopropylimidazo[1,2-a]pyridin-3-amine;
N-cyclohexyl-2-octylimidazo[1,2-a]pyridin-3-amine;
(5-(3-(cyclohexylamino)imidazo[1,2-a]pyridin-2-yl)furan-2-yl)methanol;
6-chloro-N-cyclohexyl-2-cyclopropylimidazo[1,2-a]pyridin-3-amine;
N-cyclohexyl-2-(pentan-2-yl)imidazo[1,2-a]pyridin-3-amine;
N-cyclohexyl-2-(2,4-dimethoxyphenyl)imidazo[1,2-a]pyridin-3-amine;
N-cyclohexyl-2-neopentylimidazo[1,2-a]pyridin-3-amine;
5-bromo-2-(2-chlorophenyl)-N-cyclohexylimidazo[1,2-a]pyridin-3-amine;
2-(2-chlorophenyl)-N-pentylimidazo[1,2-a]pyridin-3-amine;
2-(4-methoxyphenyl)-N-pentylimidazo[1,2-a]pyridin-3-amine;
N-cyclopropyl-2-(4-methoxyphenyl)imidazo[1,2-a]pyridin-3-amine;
5-chloro-2-(2-chlorophenyl)-N-cyclopentylimidazo[1,2-a]pyridin-3-amine;
N-butyl-6-chloro-2-(5-methylisoxazol-3-yl)imidazo[1,2-a]pyridin-3-amine;
N-benzyl-6-chloro-2-(5-methylisoxazol-3-yl)imidazo[1,2-a]pyridin-3-amine;
N-butyl-5,7-dimethyl-2-(5-methylisoxazol-3-yl)imidazo[1,2-a]pyridin-3-amine;
N-benzyl-2-cyclopropylimidazo[1,2-a]pyridin-3-amine;
4-(3-(cyclohexylamino)imidazo[1,2-a]pyridin-2-yl)-2,6-dimethoxyphenol;
2-(4-(benzyloxy)benzyl)-N-cyclohexylimidazo[1,2-a]pyridin-3-amine;
N-cyclohexyl-2-(pentan-3-yl)imidazo[1,2-a]pyridin-3-amine;
N-cyclohexyl-2-(4-nitrophenyl)imidazo[1,2-a]pyridin-3-amine;
2-tert-butyl-N-cyclohexylimidazo[1,2-a]pyridin-3-amine;
N-(4-(3,4-dichlorophenoxy)butyl)-2-(furan-2-yl)imidazo[1,2-a]pyridin-3-amine;
N-(4-(3,4-dichlorophenoxy)butyl)-2-isopropylimidazo[1,2-a]pyridin-3-amine;
N-(4-chlorobenzyl)-2-isopropylimidazo[1,2-a]pyridin-3-amine;
2-(5-chlorofuran-2-yl)-N-cyclohexylimidazo[1,2-a]pyridin-3-amine;
N-cyclohexyl-2-(5-ethylthiophen-2-yl)imidazo[1,2-a]pyridin-3-amine;
2-(6-chloro-2-fluoro-3-methylphenyl)-N-cyclohexylimidazo[1,2-a]pyridin-3-amine;
2-(4-chloro-3-fluorophenyl)-N-cyclohexylimidazo[1,2-a]pyridin-3-amine;
2-(4-bromophenyl)-N-cyclohexylimidazo[1,2-a]pyridin-3-amine;
2-(2-chlorophenyl)-N-(pentan-2-yl)imidazo[1,2-a]pyridin-3-amine;
2-isopropyl-N-(pentan-2-yl)imidazo[1,2-a]pyridin-3-amine;
6,8-dichloro-2-(2-chlorophenyl)-N-cyclohexylimidazo[1,2-a]pyridin-3-amine;
2-(4-bromophenyl)-N-cyclopentylimidazo[1,2-a]pyridin-3-amine;
2-(4-chloro-3-fluorophenyl)-N-cyclopentylimidazo[1,2-a]pyridin-3-amine;
2-(6-chloro-2-fluoro-3-methylphenyl)-N-cyclopentylimidazo[1,2-a]pyridin-3-amine;
N-cyclopentyl-2-(4-(trifluoromethyl)phenyl)imidazo[1,2-a]pyridin-3-amine;
N-(1-adamantyl)-2-(2-chlorophenyl)imidazo[1,2-a]pyridin-3-amine;
N-(1-adamantyl)-2-(5-methylisoxazol-3-yl)imidazo[1,2-a]pyridin-3-amine;
N-(1-adamantyl)-2-(3-methylthiophen-2-yl)imidazo[1,2-a]pyridin-3-amine;
2-(2-chlorophenyl)-N-(1-adamantyl)imidazo[2,1-a]isoquinolin-3-amine;
6-bromo-2-(2-chlorophenyl)-N-cyclohexyl-5-methylimidazo[1,2-a]pyridin-3-amine;
2-(2-chlorophenyl)-3-(cyclohexylamino)imidazo[1,2-a]pyridine-6-carbonitrile;
2-(2-chlorophenyl)-N-cyclohexylimidazo[1,2-a]quinolin-1-amine;

6-bromo-2-(2-chlorophenyl)-N-cyclohexyl-8-methylimidazo[1,2-a]pyridin-3-amine;
N-(1-adamantyl)-2-octylimidazo[1,2-a]pyridin-3-amine;
N-(1-adamantyl)-2-cyclopropylimidazo[1,2-a]pyridin-3-amine;
5-chloro-2-(2-chlorophenyl)-N-cyclohexylimidazo[1,2-a]pyridin-3-amine;
2-(2-bromophenyl)-N-cyclohexylimidazo[2,1-a]isoquinolin-3-amine;
N-cyclohexyl-2-(2,5-dichlorophenyl)imidazo[1,2-a]pyridin-3-amine;
N-cyclohexyl-2-(2-fluorophenyl)imidazo[2,1-a]isoquinolin-3-amine;
N-(2-chloro-6-methylphenyl)-2-cyclopropylimidazo[1,2-a]pyridin-3-amine;
2-(3-chlorophenyl)-N-cyclopentylimidazo[1,2-a]pyridin-3-amine;
2-(2-chlorophenyl)-3-(cyclohexylamino)imidazo[1,2-a]pyridine-5-carbonitrile;
N-(3-chlorophenyl)-2-isopropylimidazo[1,2-a]pyridin-3-amine;
N-(2-chloro-6-methylphenyl)-2-isopropylimidazo[1,2-a]pyridin-3-amine;
N-(2-chloro-6-methylphenyl)-2-ethylimidazo[1,2-a]pyridin-3-amine;
N-cyclopentyl-2-(2,5-dichlorophenyl)imidazo[1,2-a]pyridin-3-amine;
N-cyclohexyl-2-(2,4,5-trifluorophenyl)imidazo[1,2-a]pyridin-3-amine;
N,2-dicyclohexyl-8-methylimidazo[1,2-a]pyridin-3-amine;
N,2-dicyclohexyl-5-methylimidazo[1,2-a]pyridin-3-amine;
2-cyclohexyl-N-cyclopentylimidazo[1,2-a]pyridin-3-amine;
2-cyclohexyl-N-cyclopentyl-8-methylimidazo[1,2-a]pyridin-3-amine;
2-cyclohexyl-N-cyclopentyl-7-methylimidazo[1,2-a]pyridin-3-amine;
2-cyclohexyl-N-cyclopentyl-6-methylimidazo[1,2-a]pyridin-3-amine;
2-cyclohexyl-N-cyclopentyl-5-methylimidazo[1,2-a]pyridin-3-amine;
N-cyclohexyl-8-methyl-2-(1-phenylethyl)imidazo[1,2-a]pyridin-3-amine;
N-cyclohexyl-7-methyl-2-(1-phenylethyl)imidazo[1,2-a]pyridin-3-amine;
N-cyclohexyl-5-methyl-2-(1-phenylethyl)imidazo[1,2-a]pyridin-3-amine;
N-cyclopentyl-2-(1-phenylethyl)imidazo[1,2-a]pyridin-3-amine;
N-cyclopentyl-8-methyl-2-(1-phenylethyl)imidazo[1,2-a]pyridin-3-amine;
N-cyclopentyl-7-methyl-2-(1-phenylethyl)imidazo[1,2-a]pyridin-3-amine;
N-cyclopentyl-6-methyl-2-(1-phenylethyl)imidazo[1,2-a]pyridin-3-amine;
N-cyclopentyl-5-methyl-2-(1-phenylethyl)imidazo[1,2-a]pyridin-3-amine;
N-cyclohexyl-2-(2,3,6-trichlorophenyl)imidazo[1,2-a]pyridin-3-amine;
N-cyclohexyl-2-(2-fluoro-3-methoxyphenyl)imidazo[1,2-a]pyridin-3-amine;
2-(3-chloro-2-fluorophenyl)-N-cyclohexylimidazo[1,2-a]pyridin-3-amine;
N-cyclopentyl-2-octylimidazo[1,2-a]pyridin-3-amine;
N-cyclopentyl-2-(2,3,6-trichlorophenyl)imidazo[1,2-a]pyridin-3-amine;
N-cyclopentyl-2-(2-fluoro-3-methoxyphenyl)imidazo[1,2-a]pyridin-3-amine;
2-(3-chloro-2-fluorophenyl)-N-cyclopentylimidazo[1,2-a]pyridin-3-amine;
N-cyclopentyl-2-(pentan-3-yl)imidazo[1,2-a]pyridin-3-amine;
N-cyclopentyl-2-(3-methylthiophen-2-yl)imidazo[1,2-a]pyridin-3-amine;
N-cyclopentyl-2-cyclopropylimidazo[1,2-a]pyridin-3-amine;
2-sec-butyl-N-cyclopentylimidazo[1,2-a]pyridin-3-amine;
6-bromo-2-(2-chlorophenyl)-N-cyclohexyl-7-methylimidazo[1,2-a]pyridin-3-amine;
6-bromo-2-(2-chlorophenyl)-N-cyclopentyl-7-methylimidazo[1,2-a]pyridin-3-amine;
6-bromo-N-cyclopentyl-2-isopropyl-7-methylimidazo[1,2-a]pyridin-3-amine;
N-cyclopentyl-2-isopropyl-8-methylimidazo[1,2-a]pyridin-3-amine;
6-bromo-N-cyclohexyl-2-isopropyl-7-methylimidazo[1,2-a]pyridin-3-amine;
N,2-bis(2-chlorophenyl)-5-methylimidazo[1,2-a]pyridin-3-amine;
2-(2-chlorophenyl)-N-cyclohexyl-5-phenoxyimidazo[1,2-a]pyridin-3-amine;
2-(2-chlorophenyl)-N-cyclohexyl-5-ethoxyimidazo[1,2-a]pyridin-3-amine;
4-(3-(cyclohexylamino)imidazo[1,2-a]pyridin-2-yl)benzonitrile;
3-(3-(cyclohexylamino)imidazo[1,2-a]pyridin-2-yl)benzonitrile;
7-chloro-2-(2-chlorophenyl)-N-cyclohexylimidazo[1,2-a]pyridin-3-amine;
2-(2-chlorophenyl)-N-cyclohexyl-6-(4-methoxyphenyl)imidazo[1,2-a]pyridin-3-amine;
2-(2-chlorophenyl)-N-cyclohexyl-5-(4-methoxyphenyl)imidazo[1,2-a]pyridin-3-amine;
2-(2-chlorophenyl)-N-cyclohexyl-5-o-tolylimidazo[1,2-a]pyridin-3-amine;
2-(2-chlorophenyl)-N-cyclohexyl-6-o-tolylimidazo[1,2-a]pyridin-3-amine;
2-(2-chlorophenyl)-N-cyclohexylimidazo[1,2-a]pyrimidin-3-amine;
2-(2-chlorophenyl)-N-cyclohexylimidazo[2,1-a]isoquinolin-3-amine.

2. A compound as claimed in claim 1, which is selected from the group consisting of
2-(2-chlorophenyl)-N-cyclohexylimidazo[1,2-a]pyridin-3-amine;
5-bromo-2-(2-chlorophenyl)-N-cyclohexylimidazo[1,2-a]pyridin-3-amine;
5-chloro-2-(2-chlorophenyl)-N-cyclopentylimidazo[1,2-a]pyridin-3-amine;
6,8-dichloro-2-(2-chlorophenyl)-N-cyclohexylimidazo[1,2-a]pyridin-3-amine;
2-(2-chlorophenyl)-3-(cyclohexylamino)imidazo[1,2-a]pyridine-6-carbonitrile;
2-(2-chlorophenyl)-N-cyclohexylimidazo[1,2-a]quinolin-1-amine;
5-chloro-2-(2-chlorophenyl)-N-cyclohexylimidazo[1,2-a]pyridin-3-amine;
2-(2-chlorophenyl)-3-(cyclohexylamino)imidazo[1,2-a]pyridine-5-carbonitrile;

6-bromo-2-(2-chlorophenyl)-N-cyclohexyl-7-methylimidazo[1,2-a]pyridin-3-amine;

2-(2-chlorophenyl)-N-cyclohexyl-5-phenoxyimidazo[1,2-a]pyridin-3-amine; and

N-cyclohexyl-2-(2,4,5-trifluorophenyl)imidazo[1,2-a]pyridin-3-amine.

3. A compound as claimed in claim 2, which is selected from the group consisting of 5-chloro-2-(2-chlorophenyl)-N-cyclopentylimidazo[1,2-a]pyridin-3-amine;

5-chloro-2-(2-chlorophenyl)-N-cyclohexylimidazo[1,2-a]pyridin-3-amine;

2-(2-chlorophenyl)-3-(cyclohexylamino)imidazo[1,2-a]pyridine-5-carbonitrile.

4. A compound as claimed in claim 3, which is 5-chloro-2-(2-chlorophenyl)-N-cyclopentylimidazo[1,2-a]pyridin-3-amine.

5. A compound as claimed in claim 3, which is 5-chloro-2-(2-chlorophenyl)-N-cyclohexylimidazo[1,2-a]pyridin-3-amine.

6. A compound as claimed in claim 3, which is 2-(2-chlorophenyl)-3-(cyclohexylamino)imidazo[1,2-a]pyridine-5-carbonitrile.

7. A pharmaceutical composition for treating a subject infected with HIV, the composition including a compound as claimed in claim 1.

8. A method of treating a subject who has been infected by HIV, the method comprising administering to a subject in need thereof a compound of claim 1.

* * * * *

UNITED STATES PATENT AND TRADEMARK OFFICE
CERTIFICATE OF CORRECTION

PATENT NO.       : 8,501,767 B2
APPLICATION NO.  : 13/119431
DATED            : August 6, 2013
INVENTOR(S)      : Bode et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 170 days.

Signed and Sealed this
Fifteenth Day of September, 2015

Michelle K. Lee
*Director of the United States Patent and Trademark Office*